US006168568B1

United States Patent
Gavriely

(10) Patent No.: US 6,168,568 B1
(45) Date of Patent: Jan. 2, 2001

(54) PHONOPNEUMOGRAPH SYSTEM

(75) Inventor: Noam Gavriely, Haifa (IL)

(73) Assignee: Karmel Medical Acoustic Technologies Ltd., Yokneam Ilit (IL)

( * ) Notice: Under 35 U.S.C. 154(b), the term of this patent shall be extended for 0 days.

(21) Appl. No.: 08/729,651

(22) Filed: Oct. 4, 1996

(51) Int. Cl.[7] .................................................. A61B 5/103
(52) U.S. Cl. ............................ 600/529; 600/538; 600/586
(58) Field of Search ................................... 600/300, 528, 600/529, 532, 544, 484, 301, 586; 128/204.23, 204.21

(56) References Cited

U.S. PATENT DOCUMENTS

| 4,982,738 | * | 1/1991 | Griebel | 600/529 |
| 5,010,889 | * | 4/1991 | Bredesen et al. | 600/528 |
| 5,058,600 | * | 10/1991 | Schechter et al. | 600/533 |
| 5,134,995 | * | 8/1992 | Gruenke et al. | 128/204.23 |
| 5,213,108 | | 5/1993 | Bredesen et al. . | |
| 5,259,373 | * | 11/1993 | Gruenke et al. | 128/204.23 |
| 5,309,922 | * | 5/1994 | Schechter et al. | 600/534 |
| 5,549,106 | * | 8/1996 | Gruenke et al. | 128/204.23 |
| 5,553,609 | * | 9/1996 | Chen et al. | 600/301 |

FOREIGN PATENT DOCUMENTS

| 2 240 392 | 7/1991 | (GB) . |
| PCT/US90/05120 | 4/1991 | (WO) . |
| WO 91 03981 | 4/1991 | (WO) . |
| WO 96 19142 | 6/1996 | (WO) . |

OTHER PUBLICATIONS

T. Rosqvist, et al : "Tool kit for lung sound analysis" Medical and Biological Engineering & Computing, vol. 33, No. 2 Mar. 1995, pp. 190–195. See attached international search for pertinent pages.

A. Cohen, et al: "Analysis and Automatic Classification of Breath Sounds" IEEE Transactions on Biomedical Engineering, vol. 31, No. 9, Sep. 1984, NY, USA pp. 585–590. See attached international search for pertinent pages.

A. Cohen: "Signal Processing Methods for Upper Airway andPpulmonaryDysfunction Diagnosis" IEEE Engineering in Medicine & Biology, vol. 9, No. 1, Mar. 1990, NY USA, pp. 72–75. See attached international search for pertinent pages.

* cited by examiner

Primary Examiner—Robert L. Nasser
(74) Attorney, Agent, or Firm—Fenster & Company Patent Attorneys, Ltd.

(57) ABSTRACT

A phonopneumograph system for analyzing breath sounds includes a plurality of breath related sensors placed around the respiratory system of a patient for measuring breath related activity and a breath analyzer. The breath analyzer matches the breath sound data produced by the breath related sensors to a plurality of breath sound templates each of which parametrize one type of breath sound and determines the presence of regular and/or adventitious breath sounds only when the breath sound data matches, within predetermined goodness of fit criteria, one or more of the breath sound templates.

90 Claims, 30 Drawing Sheets

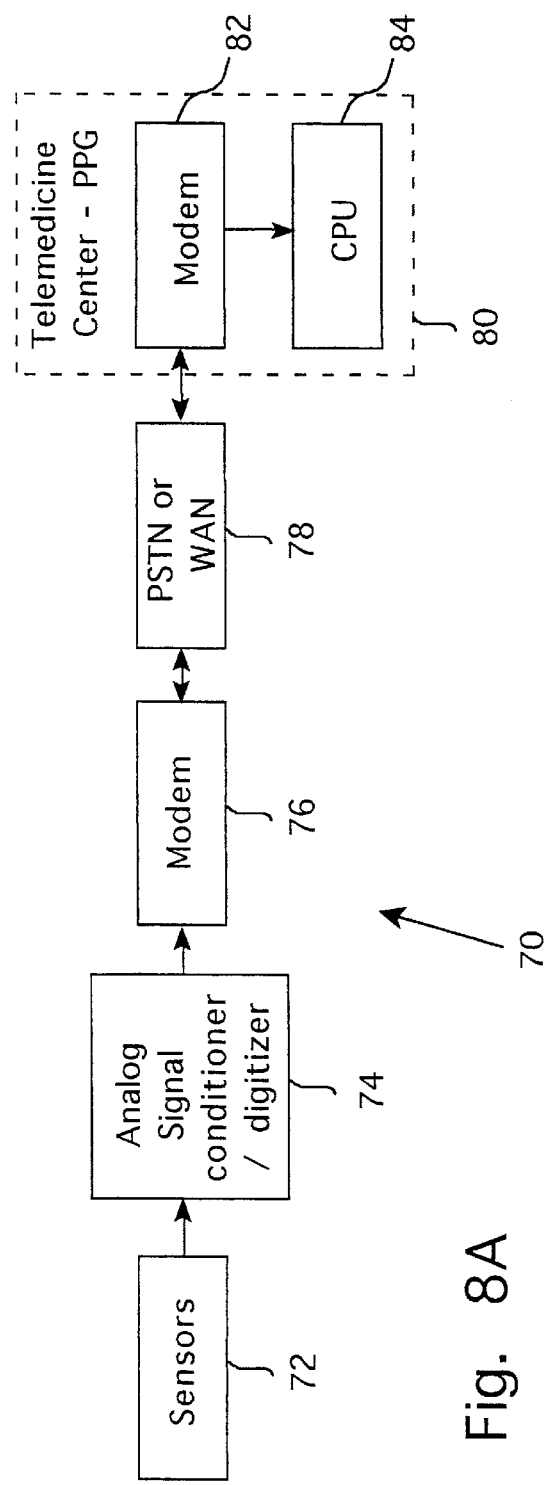
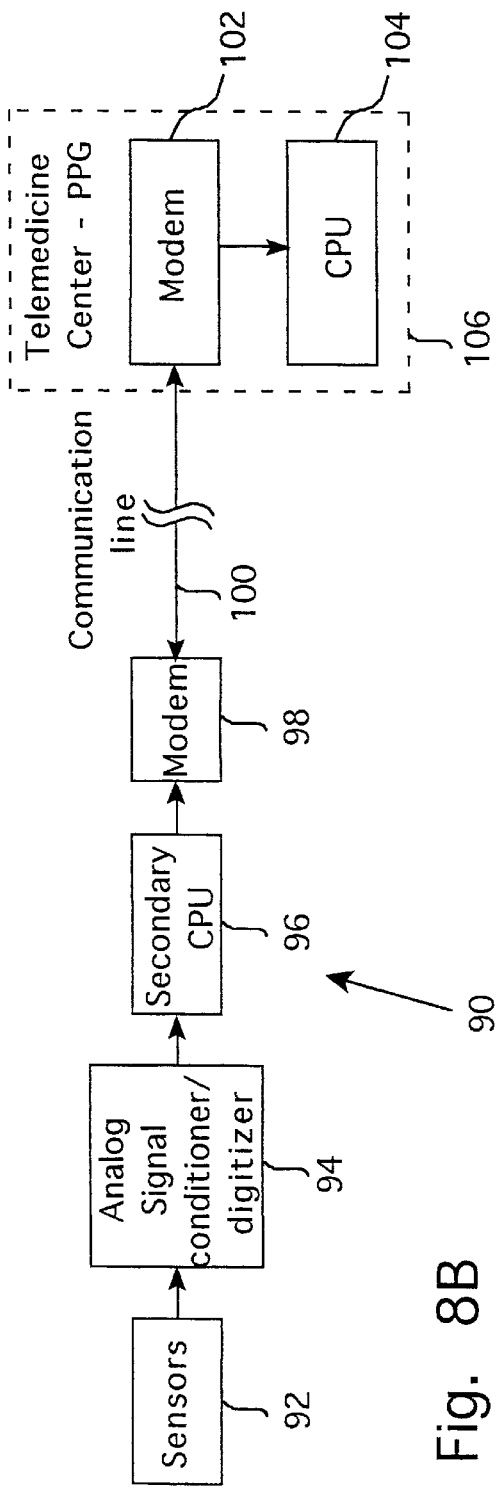
Fig. 8A
Fig. 8B

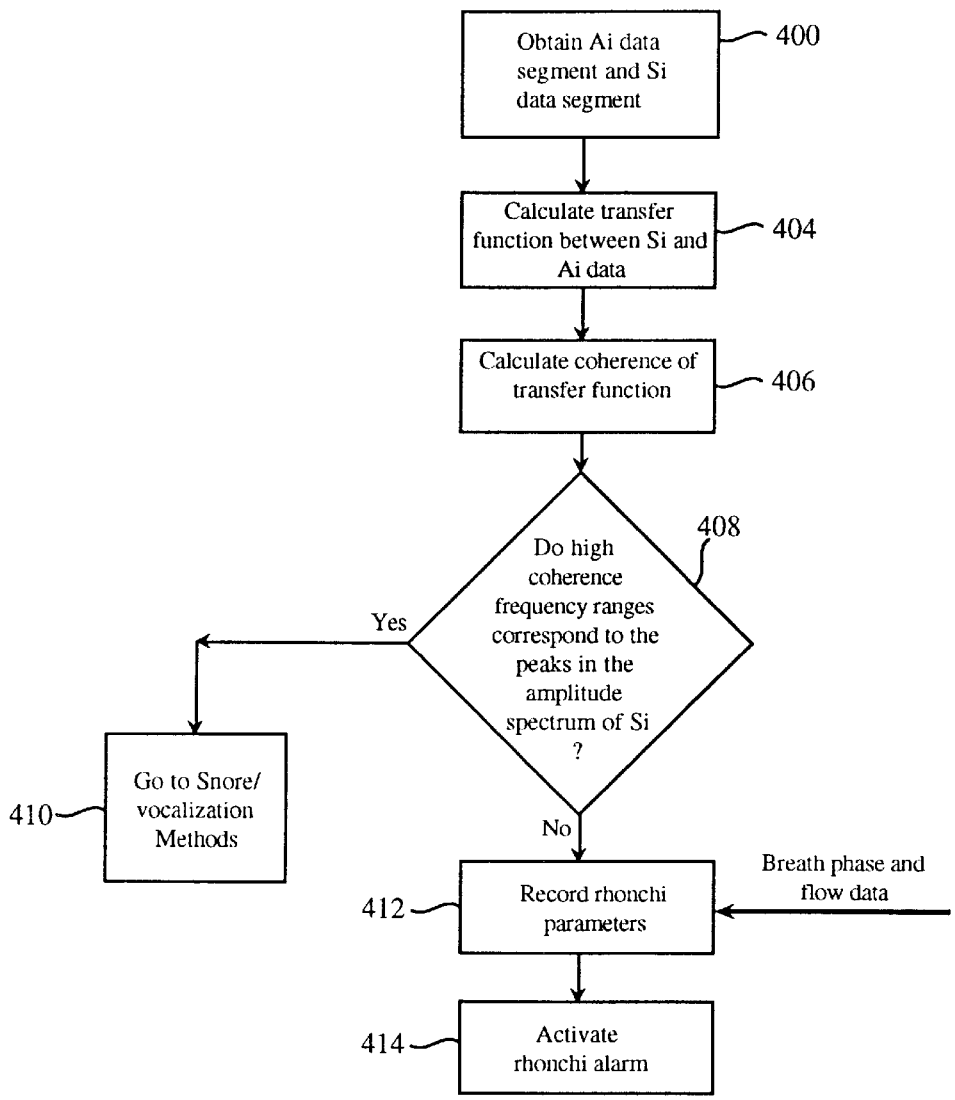

PHONOPNEUMOGRAPH SYSTEM

FIELD OF THE INVENTION

The present invention relates to a method, system and apparatus for the detection and analysis of body sounds in general and to a method, system and apparatus for the automatic detection and analysis of breath sounds in particular.

BACKGROUND OF THE INVENTION

The art of listening to body sounds, or auscultation, has been used by physicians for thousands of years, for diagnosing various diseases.

Auscultation was initially performed by placing the physician's ear directly on the skin of the patient. At the beginning of the 19th century, R. T. Laënnec introduced a tool, the stethoscope, for transmitting of body sounds to the ear.

Currently used stethoscopes include a "chest piece" brought into contact with the patient's skin, and two flexible tubes, terminating in the physician's ears. Pulmonary sounds are typically classified into normal breath sounds and adventitious (abnormal) breath sounds. The type of adventitious breath sounds, their temporal location relative to the inspiration and expiration phases of the respiratory cycle and their rate of occurrence are used to diagnose the nature and severity of pulmonary diseases.

Adventitious breath sounds are usually divided into continuous and discontinuous sounds depending on their duration. Continuous sounds are further subdivided into wheezes, which are higher pitched musical sounds indicating the presence of airway narrowing and rhonchi, which are low-pitched, grinding sounds. Discontinuous adventitious breath sounds are similarly divided into coarse crackles, which are short intermittent explosive sounds having a lower pitch, and fine crackles, which are less loud, shorter in duration, and higher in pitch. Crackles are usually indicative of obstructive airway diseases or restrictive lung diseases (depending on their timing in the respiratory cycle).

The use of various sensors which transform the acoustic signals of the body into electrical voltages is well known in the art. Various types of transducers have been used in implementing body sound sensors, including both air coupled and contact microphones or accelerometers. An improved contact sensor for body sounds has been disclosed by the present inventor in U.S. patent application Ser. No. 08/654,643 filed on May 29, 1996 and entitled "A Contact Sensor for Body Sounds".

The introduction of computerized signal processing methods has facilitated quantitative and objective analysis of breath sounds. Methods have been developed which transform the acoustic signals to the frequency domain, characterize the signals' temporal and spectral patterns, and extract features that distinguish the various classes of normal and abnormal breath sounds, as described in the book, *Breath Sounds Methodology* by Noam Gavriely, CRC Press Inc, 1995.

U.S. Pat. No. 5,213,108 to Bredesen and Schmerler discloses a visual display stethoscope which enables the visual display of acoustic data including breath sounds and manual measurement of certain parameters of the acoustic waveform. Methods involving the manual analysis of visually displayed digitized waveforms are time consuming, require the analysis to be performed by an expert and lack objective and uniform criteria for quantitative identification of adventitious sounds.

Published PCT Application WO 91/03981 to Murphy discloses a system and method for automatically detecting and identifying certain adventitious sounds. The method of crackle identification is based on two primary parameters, the amplitude and duration of the crackle wave (half cycle), and on one secondary parameter, the slope of one of the waves.

Crackle detection methods based on wave amplitude analysis as a primary detection criterion have an inherent disadvantage due to the fact that the amplitude of crackles is often similar to or even smaller than the amplitude of the underlying breath sounds. A simple threshold crossing criterion will miss the majority of crackles, thus rendering the rest of the analysis useless.

Nocturnal respiratory symptoms are common, yet difficult to assess. They include nighttime dyspnoea caused by cardiac, gastrointestinal, and pulmonary disease processes. Paroxysmal nocturnal dyspnoea (PND) is a symptom of congestive heart failure (CHF) where water accumulates in the lung of the supine patient and interferes with alveolar gas exchange. This process leads to a sudden onset of breathlessness, usually during the third part of the night, which is relieved by shifting to an upright posture. Gastroesophageal reflux of acidic content from the stomach in supine patients is often associated with aspiration of the acid into the airways that causes an acute onset of cough, wheezing and dyspnoea. A nighttime onset of asthma attacks is common in children. It is often suspected by the physician after hearing a description of the course of events by a parent, but an objective diagnosis is difficult. Especially since at least some of these children have normal physical examination and spirometry during the day. Another class of nocturnal breathing disorders is the obstructive sleep-apnea (OSA) syndrome and its related conditions (hypopnea, snoring). In these conditions, the patient's upper airway collapses or becomes narrowed or flutter develops, leading to a complete or partial interruption of the flow. OSA causes interference with the normal pattern of sleep, multiple (some time as many as hundreds) arousals during the night and reduced oxygenation.

Each of these clinical conditions have distinct breath sound features. Progressive pulmonary water overload is initially associated with the generation of inspiratory crackles, with an increasing range of chest wall distribution, and eventually, the emerging of expiratory crackles and wheezes. In addition, there is a gradual increase in the respiratory rate (tachypnea). An acute onset of cough, wheezing and secretion sounds (rhonchi and expiratory crackles) is a marker of aspiration. Finally, a gradual onset of wheezing with or without coughing is associated with bronchial asthma.

A disadvantage of the prior art of manual auscultation is that it cannot provide a reliable objective and continuous detection and documentation of the occurrence of nocturnal adventitious breath sounds with respect to time, and while the patient is sleeping. Thus, prior art auscultation methods do not provide a reliable objective method for accurately diagnosing and documenting respiratory symptoms.

SUMMARY OF THE PRESENT INVENTION

There is therefore provided, in accordance with a preferred embodiment of the present invention, a phonopneumograph system for analyzing breath sounds, the phonopneumograph system includes a plurality of breath related sensors placed around the respiratory system of a patient for measuring breath related activity, a breath analyzer for matching the breath sound data produced by the breath related sensors to a plurality of breath sound templates each of which parametrize one type of breath sound and for determining the presence of regular and/or adventitious breath sounds only when the breath sound data matches, within predetermined goodness of fit criteria, one or more of the breath sound templates.

Additionally, in accordance with a preferred embodiment of the present invention, the sensors include at least one of the following type of sensors: chest expansion sensors, breath sounds sensors, tracheal sound sensors, flow meters and spirometers.

Moreover, in accordance with a preferred embodiment of the present invention, the plurality of breath sound templates parametrize at least one of the following sounds: regular chest wall breath sound, regular tracheal breath sound, a wheeze, a cough, a rhonchus, a snore and a crackle.

Additionally, in accordance with a preferred embodiment of the present invention, the phonopneumograph system also includes an ambient noise microphone for measuring ambient noise data from the space in which a patient is.

Further, in accordance with a preferred embodiment of the present invention, the template for regular chest wall breath sound is the curve in the frequency domain of the breath sound data of a low pass filter, wherein the parameters stored are the amplitude, cutoff frequency and slope of the low pass filter.

Yet, in accordance with a preferred embodiment of the present invention, the template for regular tracheal breath sound is a curve in the frequency domain of the breath sound data of an ensemble of second order systems wherein the parameters stored are a set of amplitude coefficients, a set of damping coefficients and a set of resonance frequencies.

Still further, in accordance with a preferred embodiment of the present invention, the template for a wheeze is a narrow peak in the frequency domain of the breath sound data whose width at half height spreads less than 32 Hz to either side of the frequency of the narrow peak. In addition, the peak has less than three harmonics and occurs within at least three 50 ms segments. The frequency of the narrow peak varies less than 10% within the segments and the breath sound data is not significantly correlated with the ambient noise data.

Additionally, in accordance with a preferred embodiment of the present invention, the template for a rhonchus is a repetitive sound in the breath sound data having generally evenly spaced peaks in the time and frequency domains. The repetitive sound is not significantly found in the ambient noise data.

According to a preferred embodiment of the present invention, the template for a snore is a repetitive sound in the breath sound data having generally evenly spaced sound structures in the time domain and evenly spaced peaks in the frequency domain, whose average spacing between sound structures in the time domain is generally equivalent to the inverse of the average spacing between peaks in the frequency domain and wherein the breath sound data is significantly correlated with the ambient noise data.

Additionally, in accordance with a preferred embodiment of the present invention the template for a cough is a sound occurring during expiration which endures 0.2–3 seconds. The template for a cough has a double hump envelope in the time domain. In addition the template for a cough has a relatively flat spectrum and the cough sound is significantly correlated with the ambient noise data.

Still further, in accordance with a preferred embodiment of the present invention, the template for a crackle is a curve, whose onset point begins as an abrupt change in the breath sound data. The curve generally matches the following function: $y = A \cdot B(t) \cdot C(t)$ where y is the breath sound data beginning at the onset point, t begins at the onset point, A is an amplitude parameter, $B(t)$ is an envelope function and $C(t)$ is an oscillatory function.

Yet further, in accordance with a preferred embodiment of the present invention, the phonopneumograph system includes a stethoscope converter. The stethoscope, includes at least a channel selector and at least one speaker. The stethoscope receives the breath sound data and provides the data to the ears of an operator.

Additionally, in accordance with a preferred embodiment of the present invention, the phonopneumograph system includes a timing analyzer for determining the timing of breathing activity and the relative timing and duration of at least one of the regular and adventitious breath sounds.

There is also provided, in accordance with a preferred embodiment of the present invention, a phonopneumograph system for analyzing breath sounds. The phonopneumograph system includes a plurality of breath related sensors placed around the respiratory system of a patient. The phonopneumograph measures breath related activity and produces therefrom breath sound data. The phonopneumograph system also includes a breath analyzer for determining regular breathing activity and for identifying whether or not any of the following adventitious breath sounds: a wheeze, a cough, a rhonchus, a snore and a crackle, are present within the breath sound data.

There is additionally provided, in accordance with a preferred embodiment of the present invention, a further phonopneumograph system for analyzing breath sounds. The phonopneumograph system includes a plurality of breath related sensors placed around the respiratory system of a patient for measuring breath sound data. The phonopneumograph system also includes an ambient noise microphone placed near the patient for measuring ambient noise data. The phonopneumograph system further includes an ambient noise level detector utilizing the ambient noise data to quantify the level of noise in the presence of the sensors. The phonopneumograph system also includes a loud noise analyzer which detects the presence of snores and coughs in the breath sound data when the ambient noise level detector detects loud noise in the ambient noise data. The phonopneumograph system also includes a breath analyzer which determines regular breathing activity and detects adventitious breath sounds in the breath sound data when the ambient noise level detector detects a low level of noise.

There is also provided, a breath sounds monitor, in accordance with still another preferred embodiment of the present invention. The breath sounds monitor includes a plurality of breath related sensors placed around the respiratory system of a patient. The breath related sensors measure breath sound data. The breath sounds monitor also includes a breath analyzer which continuously analyzes the breath sound data and determines the presence of breathing. In addition, the breath analyzer detects adventitious breath sounds in the breath sound data and provides alert indications whenever abnormal breath sounds or adventitious breath sounds are present.

Further, in accordance with yet another preferred embodiment of the present invention, the breath analyzer of the breath sounds monitor includes a symmetry monitor which detects asymmetry and imbalance in the breath sound data output from those of the breath related sensors placed on the lateral sides of the chest and provides an alert when such asymmetry and imbalance are detected.

Additionally, in accordance with another preferred embodiment of the present invention, the breath sounds monitor also includes a display which indicates the breathing. In addition, the display indicates when and to what extent each of the adventitious breath sounds occurred and produces an alert whenever dangerous adventitious breath sounds are present.

Further, in accordance with another preferred embodiment of the present invention, the breath analyzer also includes a log unit. The log unit logs template parameters of the detected adventitious sounds. The log unit can also log parameters of the breath sounds.

Additionally, in accordance with another preferred embodiment of the present invention, the log unit includes a report unit. The report unit reports the template parameters and analyzes and presents trends of the detected adventitious sounds.

Still further, in accordance with a preferred embodiment of the present invention, the breath analyzer includes an apnea monitor. The apnea monitor monitors the lengthy absence of breathing and provides an alert indication whenever such absence occurs.

Additionally, in accordance with a preferred embodiment of the present invention, the breath analyzer includes a training unit. The training unit defines an initial state of breathing of a patient. The breath analyzer further includes a change unit. The change unit provides an alert whenever the current state of breathing is significantly different from the initial state of breathing.

Furthermore, in accordance with a preferred embodiment of the present invention, the phonopneumograph system additionally includes a raw data recorder unit for recording the breath sound data. The raw data recorder is activated in one of the following ways: via an operator, whenever adventitious breath sounds are detected and at regular intervals.

There is also provided, in accordance with a preferred embodiment of the present invention, an apnea monitor. The apnea monitor includes at least one breath related sensor placed around the respiratory system of a patient for measuring breath sound data. The apnea monitor also includes a breath analyzer. The breath analyzer continuously matches the breath sound data produced by at least one of the breath related sensors to at least one regular breath sound template and determines the presence of breathing. The breath analyzer also provides an alert indication whenever no breathing is present.

There is also provided, in accordance with a preferred embodiment of the present invention, a breath sounds meter. The breath sounds meter includes a plurality of breath related sensors placed around the respiratory system of a patient. The breath sound meter measures breath sound data during a single session. The breath sounds meter also includes an ambient noise microphone placed near the patient for measuring ambient noise data. The breath sounds meter also includes an ambient noise level detector which utilizes the ambient noise data to quantify the level of noise in the presence of the sensors. The breath sounds meter also includes a loud noise analyzer for detecting the presence of coughs in the breath sound data when the ambient noise level detector detects loud noise in the ambient noise data. The breath sounds meter further includes a breath analyzer for determining regular breath sounds and for detecting adventitious breath sounds in the breath sound data when the ambient noise level detector detects a low level of noise. The breath sounds meter additionally includes a display. The display indicates at least the regular breathing. The display additionally indicates when, in the respiratory cycle, each of the adventitious breath sounds occurred.

Additionally, in accordance with a preferred embodiment of the present invention, the display can display graphical, textual and parametric descriptions of the regular breathing and the adventitious breath sounds.

Yet further, in accordance with a preferred embodiment of the present invention, the breath sounds meter also includes a communication unit. The communication unit transmits breath information to an external physician unit.

Still further, in accordance with a preferred embodiment of the present invention, the breath information communicated by the breath sounds meter is any one of the following: the raw breath sound data, the parameters of the regular breathing and the detected adventitious breath sounds and a report of the state of breathing over a predetermined period of time.

There is also provided, in accordance with a preferred embodiment of the present invention, a breath sounds recorder. The breath sounds recorder includes a plurality of breath related sensors placed around the respiratory system of a patient. The breath related sensors continuously measure breath sound data during a relatively long period. The breath sounds recorder also includes a breath analyzer for matching the breath sound data produced by the breath related sensors to a plurality of breath sound templates each of which parametrize one type of breath sound and for determining the presence of regular and/or adventitious breath sounds only when the breath sound data matches, within predetermined goodness of fit criteria, one or more of the breath sound templates. The breath sounds recorder also includes a storing unit for storing at least the parameters of detected adventitious breath sounds and the times at which they occurred.

Additionally, in accordance with a preferred embodiment of the present invention, the storage unit of the breath sounds recorder also stores a small portion of the raw breath sound data.

Further, in accordance with a preferred embodiment of the present invention, the raw breath sound data is selected in one of the following ways: whenever adventitious breath sounds are detected and at regular intervals.

Additionally, in accordance with a preferred embodiment of the present invention, the breath analyzer includes a trends analyzer for analyzing trends in the breath sound data over a relatively long period.

There is also provided, in accordance with a preferred embodiment of the present invention, an additional phonopneumograph system. The phonopneumograph system includes a plurality of piezoelectric sensors placed around the respiratory system of a patient. The piezoelectric sensors measure breath related activity. The phonopneumograph system also includes a verification unit connected to the sensors. The verification unit individually activates each sensor to produce a sound and, for each sound produced, measures the sound with the non-activated ones of the sensors. In a verification mode, the verification unit compares the measured sounds with those received during a training mode.

Further, in accordance with a preferred embodiment of the present invention, the breath sounds analyzer includes a template matcher. The template matcher matches the breath sound data produced by the breath related sensors to a plurality of breath sound templates each of which parametrize one type of breath sound and determines the presence of regular and/or adventitious breath sounds only when the breath sound data matches, within predetermined goodness of fit criteria, one or more of the breath sound templates.

There is also provided, in accordance with a preferred embodiment of the present invention, a hardware verification method for a system having a plurality of piezoelectric sensors placed around an object. In a training mode, the hardware verification method includes the steps of: 1) individually activating each sensor to produce a sound, 2) for each sound produced, measuring the sound with the non-activated ones of the sensors and 3) storing the measured sounds. In a verification mode, the hardware verification method includes the steps of: 1) individually activating each sensor to produce a sound, 2) for each sound produced, measuring the sound with the non-activated ones of the sensors and 3) identifying malfunctioning sensors by comparing the measured sounds with those received during the training mode.

There is also provided, in accordance with a preferred embodiment of the present invention, a method for detecting a wheeze in breath sound data. The method includes the steps of: 1) segmenting the breath sound data into segments 2) a series of per segment operations and 3) a series of per group of segments operations.

The series of per segment operations are: a) generating the spectrum of the breath sound segment, b) removing noise and regular breath sound spectrum patterns from the breath sound spectrum, thereby to produce a non-regular breath sound spectrum and c) detecting narrow peaks within the non-regular breath sound spectrum.

The series of per group of segments operations are: d) defining a potential wheeze if narrow peaks exist in consecutive segments and if the narrow peaks are located within a predetermined small frequency range across the consecutive segments, e) defining a wheeze if the narrow peaks of the potential wheeze have less than three harmonics each.

Further, in accordance with a preferred embodiment of the present invention, the small group of segments spans at least 150 ms of breath data.

Additionally, in accordance with a preferred embodiment of the present invention, the small frequency range is not greater then 64 Hz around the frequency of the narrow peak at half height of the narrow peak.

There is also provided, in accordance with a preferred embodiment of the present invention, a method of detecting a rhonchus in breath sound data. The method includes the steps of: 1) segmenting the breath sound data into segments, 2) per each segment, detecting narrow peaks within a spectrum of the segment, 3) per a small group of segments performing the following steps: a) defining a potential rhonchus if narrow peaks exist in consecutive segments and if the narrow peaks are located within a predetermined small frequency range across the consecutive segments, b) if there are more than two harmonics in each segment, performing the following steps: c) generating a transfer function in the frequency domain between the breath sound data and measured ambient noise of the space where the breath sound data was gathered d) determining a coherence graph of the transfer function; e) defining each narrow peak as a rhonchus if the frequency range of high coherence of the coherence graph does not correspond to the frequency range of the narrow peaks.

There is also provided, in accordance with a preferred embodiment of the present invention, a method of detecting a cough in breath sound data. The method includes the steps of: 1) generating the amplitude spectrum of the breath sound data and of ambient noise data, 2) generating a transfer function between the amplitude spectra of the breath sound and ambient noise data, 3) determining a coherence graph of the transfer function, 4) finding peaks in the breath sound and ambient noise data, 5) generating an envelope of the breath sound data and determining the duration of the envelope and 6) reviewing the breath sound and ambient noise data and identifying a cough if the breath sound and ambient noise data fulfill the entirety of the following conditions: a) the breath sound is an expiration sound, b) the peaks of the breath sound data generally coincide with the peaks of the ambient noise data, c) the coherence graph has a significant portion which has a high coherence level, d) the envelope of the breath sound data has a double hump shape, e) the duration of the envelope is of a predetermined length of time.

Further, in accordance with a preferred embodiment of the present invention, the predetermined length of time of the method for detecting a cough, is 0.2–3.0 seconds.

Additionally, in accordance with a preferred embodiment of the present invention, the high coherence level of step c of the method for detecting a cough is 0.7 or greater.

There is also provided, in accordance with a preferred embodiment of the present invention, a method of detecting crackles in breath sound data. The method includes the steps of: 1) finding the locations of abrupt changes in the breath sound data, 2) for each abrupt change performing the following steps: a) finding a beginning point of the onset of the abrupt change b) attempting to match the breath sound data following the beginning point to the following curve: $y=A \cdot B(t) \cdot C(t)$, where y is the breath sound data from the beginning point, t begins at the onset point, A is an amplitude parameter, $B(t)$ is an envelope function and $C(t)$ is an oscillatory function c) identifying the presence of a crackle if the breath sound data matches the curve.

There is also provided, in accordance with a preferred embodiment of the present invention, a method of determining the state of breathing of a patient. The method includes the steps of: 1) determining the inspiration/expiration phase of a breath from chest movement data and defining a breath phase variable therefrom, 2) if the tracheal breath sound data are significant and if the external noise is low performing the following steps: a) determining if the tracheal breath sound data has a generally normal shape and if so b) generating breath flow data from the tracheal breath sound data and from the breath phase variable, otherwise c) determining if the lack of flow indicates the presence of apnea and, if so, setting an apnea alarm.

Further, in accordance with a preferred embodiment of the present invention, the method of determining the state of breathing of a patient includes the step of generating a loud noise indication if a) the ambient noise is high, b) the breath shape is not normal or c) the tracheal sound is too high.

Still further, in accordance with a preferred embodiment of the present invention, the breath flow data of the method of determining the state of breathing of a patient is defined as the tracheal sound data to a power in the range of 0.45–0.67 and the direction of the flow is defined by the breath phase variable.

There is also provided, in accordance with a preferred embodiment of the present invention, a method for analyzing breath data. The method includes the steps of: 1) generating the spectrum of the current segment, 2) determining if the current segment of data is a background segment, representing background noise, or a breath segment representing breath sounds, 3) averaging the spectra of the segments of each type to produce an average background spectrum and an average breath sound spectrum, 4) for the average breath sound spectrum, subtracting the average background spectrum therefrom to produce a relatively noiseless breath spectrum, 5) fitting the relatively noiseless breath spectrum to a predetermined normal curve and determining the quality of the fit and 6) activating an irregular breath sounds detector if the quality of fit is poor.

Further, in accordance with a preferred embodiment of the present invention, the predetermined normal spectrum is selected from a plurality of predetermined normal spectra defined by the group to which the patient belongs, wherein the group is one of the following: male, female and child.

There is also provided, in accordance with a preferred embodiment of the present invention, a method of detecting a snore in segments of breath sound data which includes the steps of: 1) determining that the current segment is an inspiratory segment, 2) generating the power spectrum of the inspiratory segment, 3) identifying peaks in the inspiratory segment and determining the average peak-to-peak time delta_t, 4) identifying at least three peaks in the power spectrum which are significantly large and determining the average peak-to-peak frequency delta_f, 5) generating a transfer function in the frequency domain between the breath sound data and measured ambient noise of the space where the breath sound data was gathered, 6) determining a coherence graph of the transfer function and 7) identifying a snore if delta_t is close to the inverse of delta_f and if the frequency range of high coherence of the coherence graph corresponds to the frequency range of the narrow peaks.

Additionally, in accordance with a preferred embodiment of the present invention, the first step of identifying includes the steps of: 1) calculating the inverse Fourier transform of the power spectrum and generating thereby cleaned data, 2) searching for a first peak in the cleaned data beginning between 5 to 25 ms from the start of the segment and 3) searching for peaks following the first peak.

Further, in accordance with a preferred embodiment of the present invention, the second step of identifying includes the steps of: 1) calculating the histogram of the power spectrum, 2) determining the variance of the histogram and 3) defining as peaks those points having values which are at k variance or higher, where k is at least three.

BRIEF DESCRIPTION OF THE DRAWINGS

The present invention will be understood and appreciated more fully from the following detailed description taken in conjunction with the drawings in which:

FIGS. 8A and 8B are schematic block diagrams illustrating two additional configurations of the PPG System of FIG. 2 in accordance with two additional preferred embodiments of the present invention;

FIG. 15 is a flow chart illustrating the steps of the rhonchi detection method in accordance with a preferred embodiment of the present invention;

DETAILED DESCRIPTION OF A PREFERRED EMBODIMENT

The Phonopneumocraph System

Figure 1:
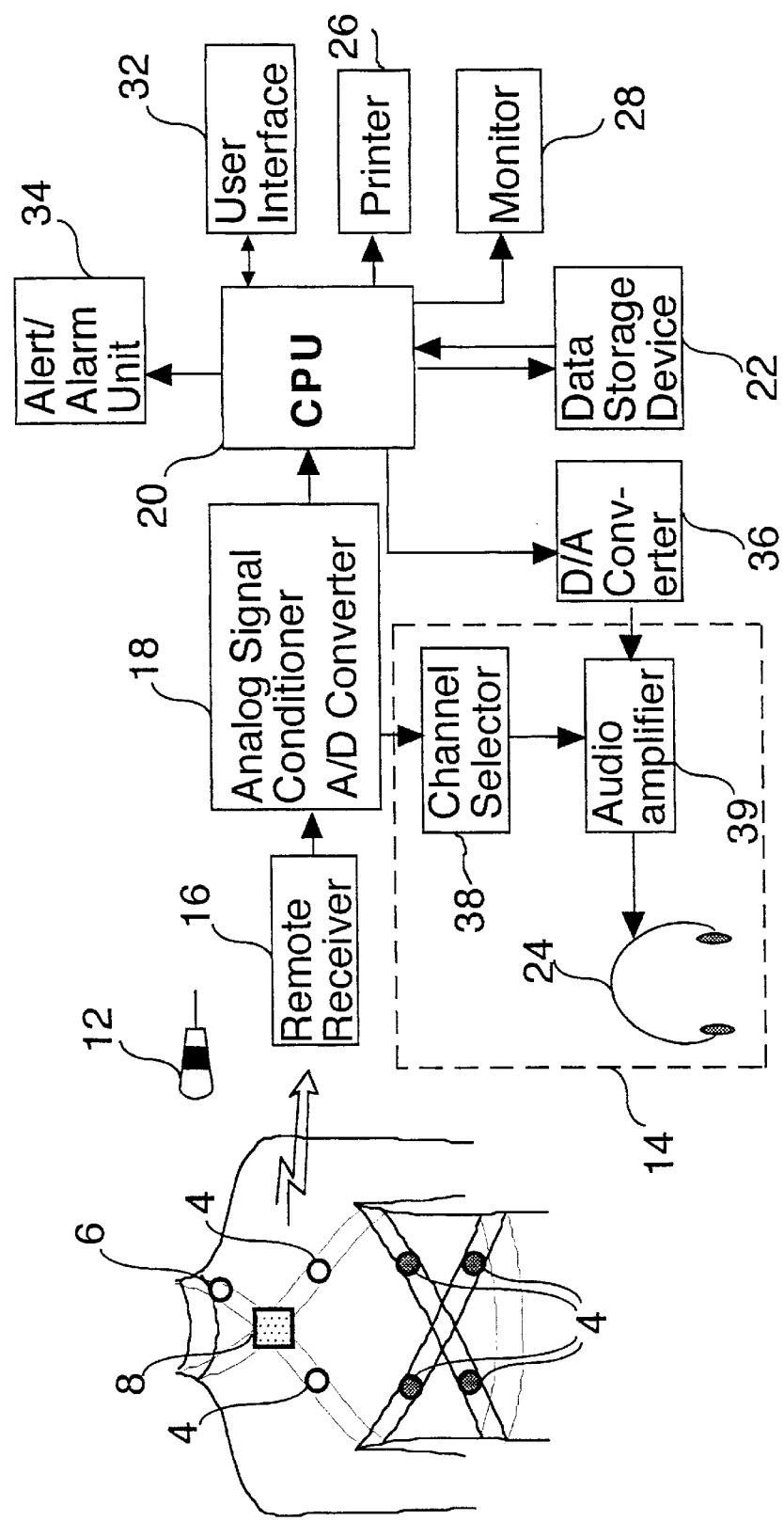
FIG. 1 is a schematic diagram illustrating a Phonopneumograph (PPG) system in accordance with a preferred embodiment of the present invention.

Reference is now made to FIG. 1 which is a schematic illustration of a Phonopneumograph (PPG) system constructed and operative for detecting, analyzing, and monitoring normal and adventitious breath sounds, documenting the results of the breath sounds analysis and recording selected portions of breath sounds in accordance with a preferred embodiment of the present invention.

The PPG system includes a plurality of wireless, chest, breath sound (BS) sensors 4, placed in contact with the patient's skin at standard back and chest positions, for picking up breath sounds. The PPG system also includes a wireless tracheal BS sensor 6, placed at a standard tracheal position, for picking up tracheal breath sounds. The PPG system further includes a wireless chest expansion (CE) sensor 8, such as a chest impedance plethysmograph sensor, suitably attached to the patient's chest for picking up chest expansion.

The PPG system also includes a wireless ambient noise microphone 12, such as a suitable air coupled microphone, placed near the patient for picking up ambient acoustic noise.

The sounds picked up by the BS sensors 4 and 6, the CE sensor 8 and the ambient noise microphone 12 are transmitted to a remote receiver 16 by any suitable means for wireless transmission, such as radio, ultrasonic or infrared transmission. The PPG system also includes an analog signal conditioner 18 connected to remote receiver 16 for amplifying, filtering and digitizing the sensors' analog signal.

The PPG system further includes a central processing unit (CPU) 20 suitably connected to analog signal conditioner 18 and to a data storage device 22 for processing the digitized sensors' signals, using a method for analysis of breath sounds as described in detail hereinbelow. It is noted that the CPU 20 can be a CPU of a commercially available personal computer or any other suitable, commercially available CPU.

The PPG system further includes a display 28 connected to the CPU 20 for on-line or off-line displaying of the results of the breath sound analysis, an alert/alarm unit 34 suitably connected to CPU 20 for generating of audible or visible alert and alarm signals and a user interface 32.

The user interface 32 receives input from an operator and can be any suitable type of interface such as a keyboard, a mouse, a touch sensitive screen a control panel or any combination thereof.

The PPG system additionally includes an electronic stethoscope 14 suitably connected to analog signal conditioner 18 and to a D/A converter 36 for enabling the PPG operator to listen to the breath sounds picked up by any BS sensor selectable from the plurality of BS sensors. The electronic stethoscope 14 includes a channel selector 38 connected between analog signal conditioner 18 and an audio amplifier 39 which, together, select the desired sensor out of the plurality of BS sensors. The audio amplifier 39 is connected to earphones 24 or a loudspeaker (not shown) for listening to the breath sounds picked up by the selected BS sensor. The operator can use the user interface 32 to select between a first mode, in which he can listen in real time to the sounds picked up by a selected BS sensor, and a second mode, in which he can listen to selected, previously digitized and recorded sounds from any selected BS sensor which are stored in a digital data storage device 22.

This latter feature is useful for simultaneous auscultation and visual monitoring of the breath sounds of a selected sensor. Additionally, this feature is useful for teaching and training purposes where it might be desirable for a student or trainee to simultaneously follow both the audible sound from a sensor and the analyzed features of breath sounds on the monitor.

It is noted that, in situations where the patient is acoustically isolated from the PPG system, for example when they are positioned in separate rooms or in situations using the capability of playback of stored data, it is also possible to connect the audio output through a suitable amplifier to a speaker system, thus enabling a group of people to listen to the amplified sound while simultaneously following the monitor data display.

The data storage device 22 can be used for storing certain selected segments of digitally recorded sensor data as well as the results of the breath sound analysis. It is noted that the digital storage device 22 can be any type of suitable digital data storage device such as a magnetic, optical, or magneto-optical digital data storage device.

The PPG system also includes a printer 26 for generating a hard-copy printout of the data output of the breath sound analysis such as graphs, tables and statistics of the results of the breath sound analysis. The hard-copy printout can be used as a condensed or detailed report for the physician, for comparison with previously generated reports and for archival purposes. Additionally, the storage device may be of the removable medium type providing a further type of permanent archival of data.

It is noted that BS sensors 4 and 6, CE sensor 8 and ambient noise microphone 12 can be any suitable type of breath sound sensor, chest expansion sensor or microphone, respectively, having a suitable frequency response. In an exemplary embodiment of the present invention, the BS sensors are contact sensors having a generally flat frequency response in the range 75–2000 Hz (±3 dB), the CE sensor 8 is an impedance chest expansion sensor having a generally flat frequency response of 0–3 Hz (±3 dB), and the ambient noise microphone 12 is an air coupled microphone having a generally flat frequency response of 50–5000 Hz (±3 dB).

Preferably, the BS sensors are of the wireless contact sensor type as shown in FIG. 1 and disclosed by the present inventor in U.S. patent application Ser. No. 08/654,643 filed on May 29, 1996 and entitled "A Contact Sensor for Body Sounds". The CE sensor 8 and ambient noise microphone 12 are also preferably wireless. However, any other type of wireless or wired BS sensor, CE sensor or ambient noise microphone, having a suitable frequency response characteristics and a suitable signal to noise ratio (S/N), can be used.

Preferably, the output of the BS sensors is independent of the magnitude of the contact force exerted by the patient's skin on the sensor.

It is noted that, in accordance with another preferred embodiment of the present invention, the BS sensors 4, the CE sensor 8 and the ambient noise microphone 12 can be electrically connected directly to the analog signal conditioner 18 by suitable wires. In this preferred embodiment, the remote receiver 16 is not included. It is noted that, if wired sensors are used, caution should be exercised to avoid introduction of artifactual noise due to friction and motion of the wires.

Figure 2:
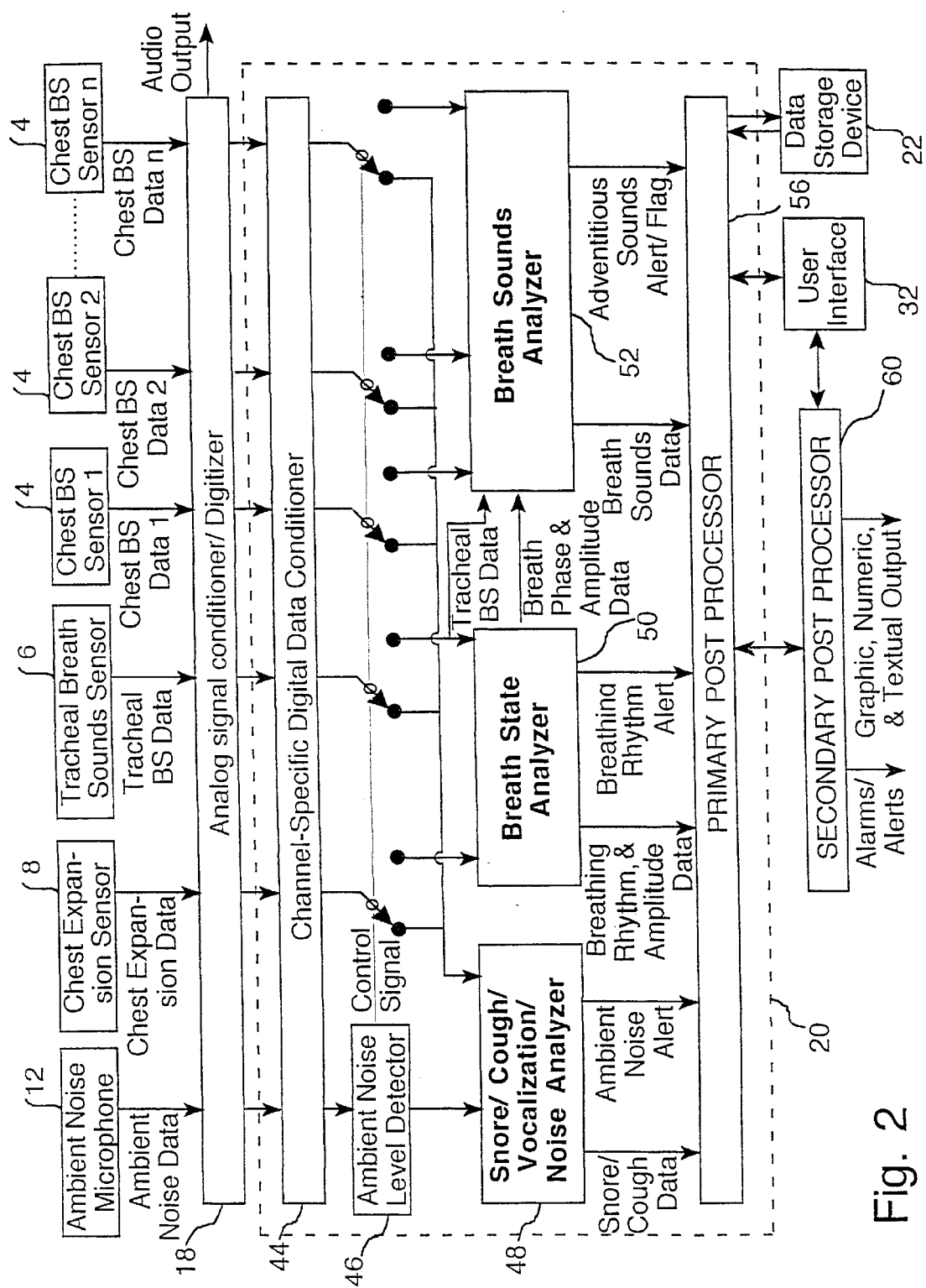
FIG. 2 is a schematic block diagram illustrating the PPG system of FIG. 1 in detail.

Reference is now made to FIG. 2 which illustrates a general schematic functional block diagram of the PPG system of FIG. 1. It is noted that the following description is a general functional description of the mode of operation of the PPG system, while the method of operation of the PPG system is separately described and illustrated in the figures hereinafter.

The signals of the BS sensors 4 and 6, CE sensor 8 and the ambient noise microphone 12 are wirelessly transmitted to the remote receiver 16 (not shown for the sake of clarity of illustration) and sent to the analog signal conditioner/digitizer 18, where they are filtered, amplified and digitized. The sensors' signals are amplified, preferably at a fixed gain of X1,000–X10,000 or with an automatic gain control, band-pass filtered, preferably with a bandwidth of approximately 75–2500 Hz, 18 dB/octave and digitized by an A/D converter for example a 12–16 bit ADC at 5,500–11,000 samples per channel per second.

Consecutive digitized data segments from all the sensors are sent to the CPU 20 for processing. The duration of the data segment can vary depending on the specific detection method used for detection of specific types of breath sounds. An exemplary data segment is 50 ms but it can vary in the range of 25–500 ms. For example the snore detection method uses a segment duration of 250±50 ms. Thus, the segment duration is preferably optimized to suit each specific adventitious sound detection method depending on the type of mathematical analysis which is used by the method for detecting specific breath sounds and on the duration and frequency content of the analyzed breath sound.

The data segments are sent to a channel specific digital data conditioner 44 where the data segments from the different sensors and the ambient noise microphone are differently processed as described in detail hereinafter. For the sake of clarity, the differently conditioned data segments of all the sensors and the ambient noise microphone are collectively referred to as the conditioned data segments hereinafter. The data segments are transferred to the memory (not shown) linked to the CPU 20 and can be also stored in the data storage device 22. A segment of the digitized data of the ambient noise microphone 12 is rectified and integrated by the channel specific digital data conditioner 44 and sent to an ambient noise level detector 46 for evaluation. The amplitude of the conditioned ambient noise data is compared to a preset or adaptive threshold.

If the amplitude of the conditioned ambient noise data is above the threshold, the system generates a control signal which diverts the conditioned data segment to a snore/cough/vocalization/noise analyzer 48 for evaluation of the acoustic characteristics of the noise and detection of snoring, cough and vocalization sounds that may be generated by the patient or by external non-patient generated noise.

The snore/cough/vocalization noise analyzer 48 receives the conditioned data segments from the tracheal BS sensor 6 and the ambient noise microphone 12. If a snore or cough are detected, the parameters of the snore or cough are calculated and sent to a primary post-processor 56 where the snore or cough count, timing and time distribution are updated and logged (by storing in data storage device 22). If no snore or cough is positively identified, the system suspends the analysis of all the conditioned data segments for as long as the noise level exceeds the threshold value. The system also records the noise duration. If the duration of the noise is longer than a user determined preset value, an "ambient noise alert" or an "ambient noise alarm" signal can be sent to the primary post-processor 56 and issued by the system (depending upon the specific system configuration).

If the ambient noise level is below threshold, the system proceeds with the analysis of the sensors' data segments.

The conditioned data segments of the CE sensor 8 and the tracheal BS sensor 6 are sent to a breath state analyzer 50. The breath state analyzer 50 receives the conditioned data segments from tracheal BS sensor 6 and the CE sensor 8 and determines the presence or absence of breathing for detection of periods of apnea (cessation of breathing). The breath state analyzer 50 also calculates the breathing rhythm (breathing rate), the breath duration and amplitude and the breathing regularity, and outputs the data to the primary post-processor 56 for further processing.

In the case of detected apnea, a breathing rhythm alert is also sent to the primary post-processor which may initiate the generation of an "apnea alarm". Additionally the breath stage analyzer determines the breath phase (inspiration or expiration), its duration and its timing which are subsequently used as references for determining the temporal relationship of detected adventitious sounds to the breathing cycle.

The breath phase and amplitude data of the breath stage analyzer are sent as input to a breath sounds analyzer 52. The breath sounds analyzer 52 also receives the conditioned data segments from the tracheal BS sensor 6 and the plurality of chest BS sensors 4. The breath sounds analyzer characterizes the normal and abnormal breath sounds, detects adventitious sounds (wheezes, crackles and rhonchi) in the data segments, calculates the parameters and timing of the various detected adventitious sounds and outputs these data and an adventitious sound alert or flag to the primary post-processor 56 for further processing and logging. The breath sounds analyzer 52 also analyzes the normal breath sounds as disclosed in detail hereinafter and outputs the analyzed breath sound data to the primary post-processor 56 for further processing and logging.

It is noted that the data segments of the various BS sensors 4 and 6 are separately conditioned by the channel specific digital data conditioner 44 and are also separately analyzed by the breath sounds analyzer 52.

The primary post-processor 56 receives the analyzed breath sound data of each of the BS sensors 4 and 6 and performs an analysis of channel inter-relationships, calculates the statistics of events and the adventitious sound distribution curves (histograms), performs a trend analysis of the various breath sound and adventitious sound data, and calculates three quality control parameters. The first quality control parameter defines the degree of matching of the normal breath sound power spectrum curve to a template. The second quality control parameter defines the degree of matching of a detected crackle sound to a crackle template. The third quality control parameter defines the degree of matching a detected wheezing sound to a wheeze template.

The primary post-processor 56 also further processes the various alarm, alert and flag conditions and sends instructions to a secondary post processor 60 for issuing the appropriate alarm or alert signals to the alarm/alert unit 34.

The secondary post-processor 60 receives data from the primary post-processor 56 and operator instructions from the user interface 32 and processes the data and the instructions to generate graphic, numerical and textual data.

The graphic, numerical and textual data generated by the secondary post-processor 60 can be sent as output to the display 28 for display, to the printer 26 for generating a hard copy report or as data files to be transferred electronically to another remote computer or telemedicine center, by modem or any other suitable means for electronic data transfer as described in detail hereinafter. Additionally, the data files created by the secondary post-processor 60 can be stored on any suitable means for data file storage, such as removable magnetic media, opto-magnetic media or other types for media, for later printing or archival purposes.

Figure 3:
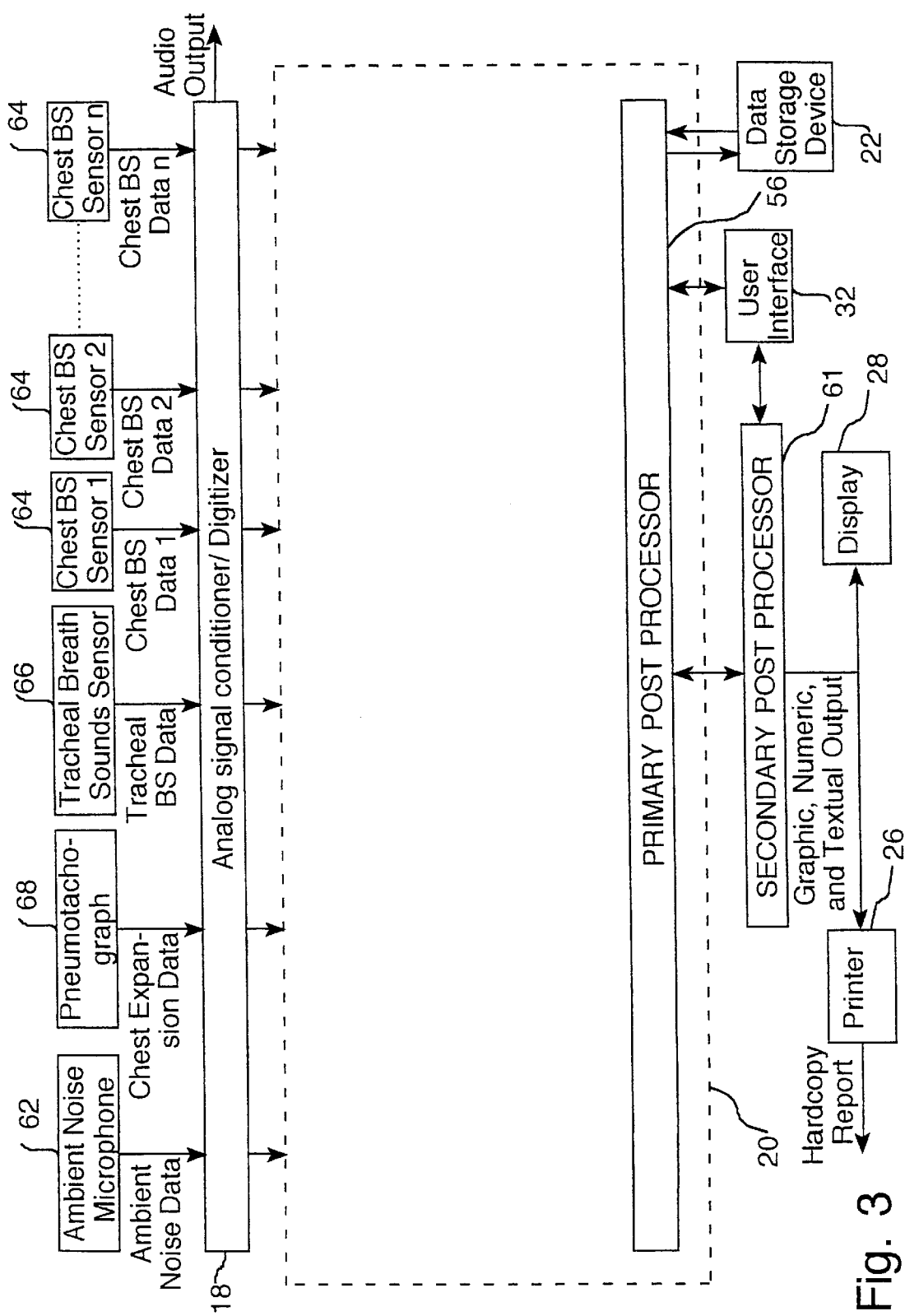
FIG. 3 is a schematic block diagram illustrating a PPG system configured as a PPG Meter in accordance with a preferred embodiment of the present invention.
Figure 4:
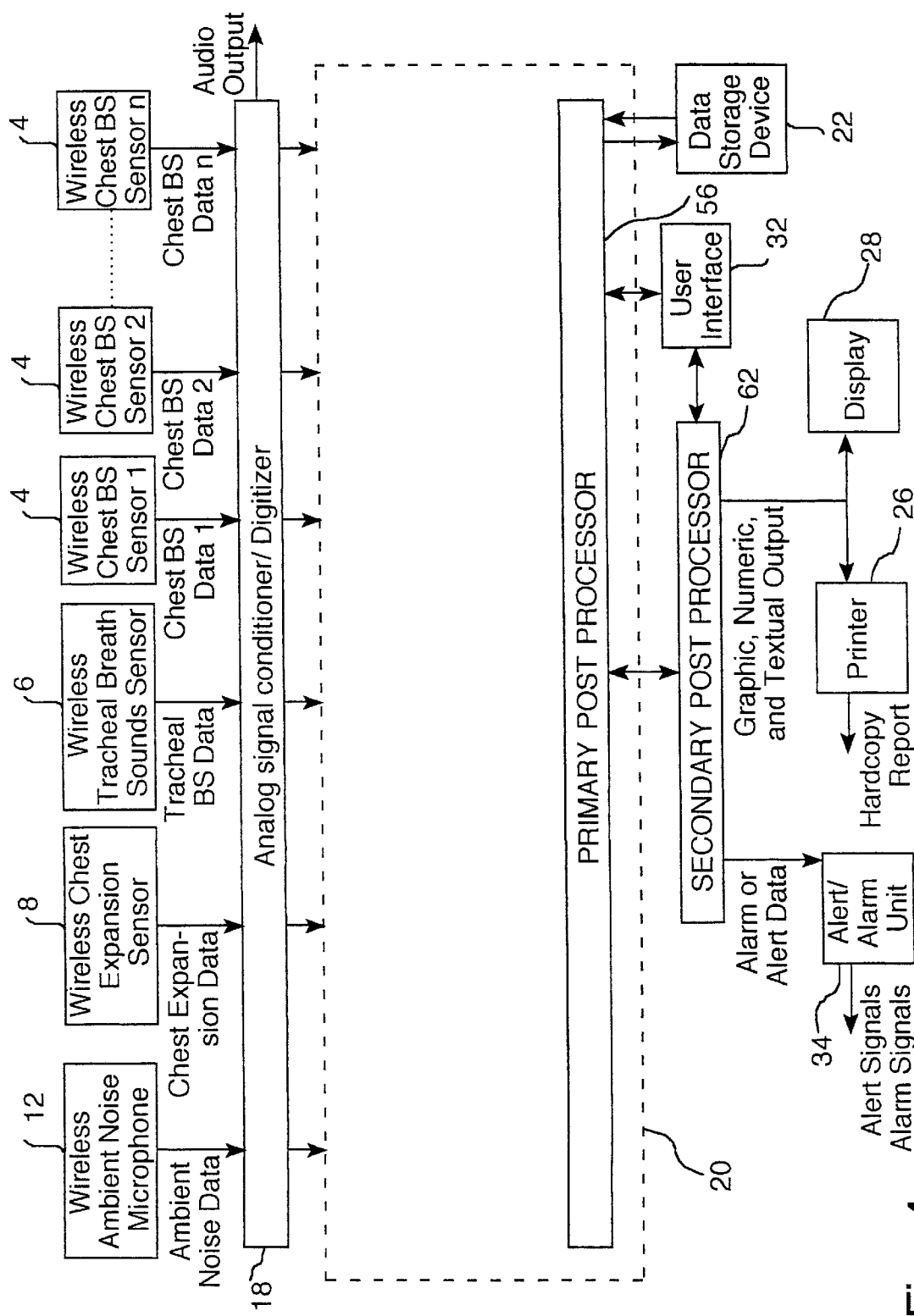
FIG. 4 is a schematic block diagram illustrating a PPG system configured as a PPG Monitor in accordance with a preferred embodiment of the present invention.
Figure 5:
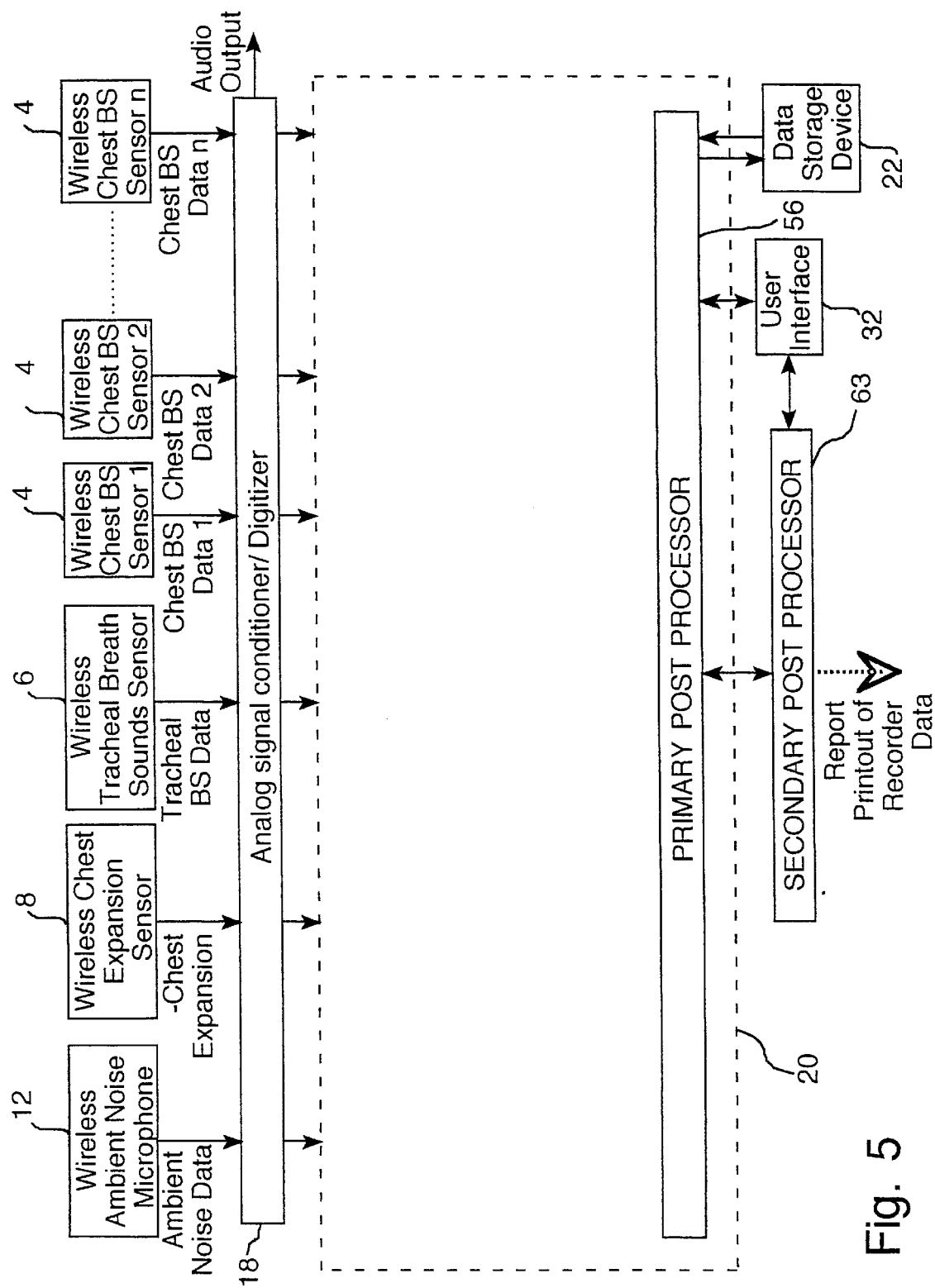
FIG. 5 is a sch ematic block diagram illustrating a PPG system configured as a PPG Recorder in accordance with a preferred embodiment of the present invention.

Reference is now made to FIGS. 3, 4 and 5 illustrating three different configurations of the PPG system of FIGS. 1 and 2. It is noted that, for a better understanding, like components are designated by like reference numerals throughout the various figures.

It is generally noted that, in the various configurations of the PPG system shown in FIGS. 3, 4 and 5 the data processing is similarly performed. The differences between the configurations are in the preferred type of sensors, the wired or wireless transmission of the sensors' signals, the secondary post-processor and the type of available output devices, such as the printer, display monitor and alarm/alert unit.

In accordance with a preferred embodiment of the present invention, selected breath sound data and parameters may be continuously displayed on display 28 (FIG. 1) as graphs or numerically, or printed out as part of a report, depending on the specific configuration of the PPG system.

The PPG Meter

FIG. 3 illustrates a PPG system configured as a PPG Meter in accordance with a preferred embodiment of the present invention. The PPG Meter includes a plurality of wired chest BS sensors 64, a wired tracheal BS sensor 66, a wired pneumotachograph 68 and a wired ambient noise microphone 62.

It is noted that, although the preferred embodiment of the PPG Meter uses the pneumotachograph 68 for flow measurement, any other sensor suitable for flow detection can be used, such as an impedance spirometry sensor or any other suitable chest expansion detecting sensor.

It is also noted that, although in the preferred embodiment of the PPG Meter of FIG. 3 the BS sensors 64 and 66, the ambient noise microphone 62 and the pneumotachograph 68 are all wired, other preferred embodiments of the PPG Meter may use wireless sensors, a wireless microphone or a wireless pneumotachograph, together with a suitable wireless receiver (FIG. 1) for receiving the respective signals thereof and sending them to the analog signal conditioner/digitizer 18.

The PPG Meter also includes the analog signal conditioner 18 (FIG. 1) which is connected to the CPU 20 (FIG. 1) and to the electronic stethoscope 14 (not shown for clarity of illustration). The CPU 20 operates as described hereinabove and is connected to a secondary post-processor 61 which is connected to the printer 26 and the display 28.

The secondary post-processor 61 further processes the data from the primary post-processor 56 and the operator input to generate graphic, textual and numeric output which is displayed on the screen of display 28 or can be printed as a hard copy report by the printer 26.

The PPG Meter is used to obtain a spot measure of the patient's breath sounds. A plurality of sensors are attached to the patient's chest and anterior neck and the pneumotachograph 68 (a flow detecting device) is activated. While the patient breathes, the system obtains and analyzes the sounds to provide an immediate output in the form of a hard copy report showing the features of the sounds in graphic and parametric notation.

The breath sounds are analyzed by the CPU 20 to determine the spectral pattern of the basic chest wall and tracheal sounds and to detect and characterize adventitious sounds. The parameters of the basic patterns are calculated and recorded by breath sounds analyzer 52. Any adventitious sounds detected are classified, the relevant quantitative parameters (e.g., wheeze duration, timing and frequency range, crackle timing, count, and parameters, etc.) are determined, presented and recorded using standard notations.

Figure 6:
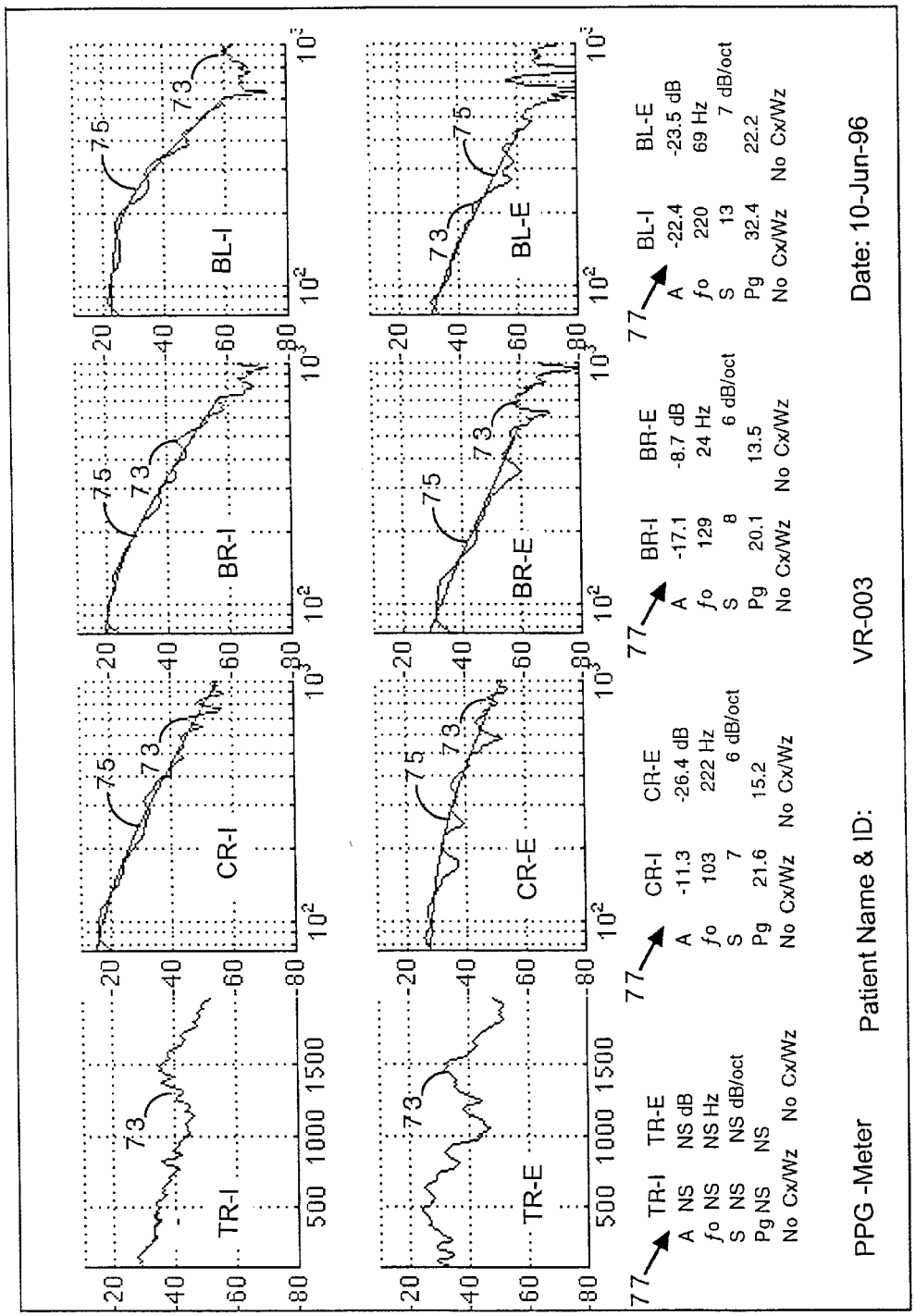
FIG. 6 illustrates an exemplary report generated by the PPG Meter of FIG. 3 in accordance with an exemplary embodiment of the present invention.

Reference is now made to FIG. 6 which illustrates an exemplary report generated by the PPG Meter of FIG. 3. The exemplary report includes eight graphs arranged in two rows. The top row of four graphs, labeled TR-I, CR-I, BR-I and BL-I, represents the averaged inspiratory breath sound (BS) power spectra of the operator selected tracheal, right anterior chest, right posterior lung base and left posterior lung base sensors, respectively. The lower row of four graphs, labeled TR-E, CR-E, BR-E and BL-E, represents the averaged expiratory breath sound (BS) power spectra of the same sensors as the top row, respectively. In all the eight graphs the vertical axes represent the log amplitude and the horizontal axes represent the log frequency. Each of the graphs includes a curve labeled 73 representing the calculated average power spectrum of the respiratory breath sound picked up by a selected sensor. If the calculated curve fit was significant, the graph also includes an additional curve labelled 75, representing the calculated fitted curve. The exemplary report of FIG. 6 also includes four numerical parameter reports, labeled 77, which include the numerical parameters fit to the spectra shown in the graphs. The parameters reported are A, $f_0$, S and Q described hereinafter. It is noted that the report can also include the number of detected crackles and their relative timing within the respiratory cycle, the parameters of detected wheezes and a textual description of the sounds.

The PPG Meter can be used to evaluate the pulmonary health status of patients of all age groups from neonates to the very elderly.

The PPG Meter can be used in primary care clinics to evaluate any patient who presents with respiratory symptoms. (An analogy may be the use of the electrocardiogram to evaluate any patient who presents cardiac-related symptoms).

The PPG Meter may also be used for follow-up of the conditions of patients with established pulmonary ailments, using their previous quantitative breath sound records as a baseline.

The PPG Meter can further be used for evaluating the effectiveness of a drug treatment on a specific individual or in a group of patients. The quantitative records of the PPG Meter allows a quantitative comparison of pre-treatment with post-treatment results. This is a considerable improvement over the prior art use of auscultation results for drug treatment evaluation since it allows the comparison of quantitatively determined breath sound parameters, thus eliminating possible bias of the results due to personal differences in the experience, training and hearing acuity of the evaluating physicians.

An additional advantage of the PPG Meter over the prior art is the fact that the records of the PPG Meter can be used as documentation and evidence when legal issues arise.

The PPG Monitor

FIG. 4 illustrates a PPG system configured as a PPG Monitor in accordance with another preferred embodiment of the present invention. The PPG Monitor includes the same components as described for the PPG system hereinabove and illustrated in FIG. 2 except that a secondary post-processor 62 replaces the secondary post-processor 60 of FIG. 2 and that the PPG Monitor additionally includes the display 28, the printer 26 and the alarm/alert unit 34 of FIG. 1.

It is noted that, in accordance with a preferred embodiment of the present invention, the plurality of sensors of the PPG Monitor may also include an esophageal sensor (not shown). For example, in cases of anaesthetized and artificially ventilated patients with endotracheal intubation, an esophageal sensor may be used.

It is also noted that the CE sensor 8 of the PPG Monitor of FIG. 4 may be any suitable chest expansion or flow measuring sensor, such as a piezoelectric chest expansion sensor, a strain gauge chest expansion sensor, an electric impedance plethysmograph sensor, a bellows with a pressure transducer, a magnetometer or an inductive plethysmograph.

The PPG Monitor is a respiratory acoustic monitor. It allows on-line, breath-by-breath monitoring and determination of the health and integrity of the respiratory system. It is intended for use in situations where continuous monitoring of respiration is important. Examples include general anesthesia with endotracheal intubation; adult, pediatric, and neonatal critical care medicine; emergency medicine; pulmonary medicine where bronchial provocation tests are used, and in individuals (infants and adults) who are at increased risk for sudden death due to breathing irregularity. The PPG Monitor performs the analysis of breath sounds as generally described hereinabove for the PPG system and illustrated in FIG. 2.

An additional feature of the PPG Monitor is that it initially "learns" the features of the sounds of the specific patient. A catalog is generated which is subsequently used as a reference for evaluation of changes and trends. If abnormal sounds are detected during the initial period, generally referred to as the "training" period hereinafter, the PPG Monitor provides an alert signal during this stage by activating the alert/alarm unit 34. Following the initial "training" period, the PPG Monitor carries out a breath-by-breath analysis of the breath sounds.

The CPU 20 evaluates the intensity, timing, spectral content, and specific properties of the sounds from each sensor, with respect to the ambient noise and in comparison with the reference catalog. The PPG Monitor searches for specific events such as wheezes or crackles, breath sound intensity shifts (throughout all sensors or in one compared with others), breathing irregularities such as apnoea or periodic breathing, and the presence of rhonchi, cough, stridor, secretion sounds or snores. Once the onset of such an event is detected, the system generates an alarm signal and may also record information regarding the timing and frequency content of the event in a data log. The primary post-processor 56 calculates and presents the trends and statistical information of the respiratory rate, apnea duration distribution, relative duration of wheezes and the counts of crackles, cough, and snores.

The PPG Monitor screens for and parametrizes the following features of the breath sounds:
1. The presence, timing, intensity, and spectral content of ambient noises.
2. The presence of breath sounds.
3. The correlation between the sounds picked up by the chest, tracheal (and possibly the esophageal) sensors.
4. The matching of the spectral patterns of the breath sounds to those of the corresponding normal templates.
5. The matching of the spectral patterns to those of the corresponding templates identified during the most recent "training" period.
6. The presence of wheezes and their parameters.
7. The presence of crackles and their parameters.
8. The presence of secretion sounds (expiratory crackles, rhonchi).
9. An imbalance between the signals reaching the lateral chest wall sensors.
10. Temporal irregularity of the breathing sounds.
11. The presence of coughs.
12. The presence of snores.

The outcome of the screening procedures is a decision tree that determines whether the breath sounds have been altered in a clinically significant fashion that evokes the triggering of an alarm, as is described in detail hereinafter.

The PPG Monitor acquires data continuously from the BS sensors 4 and 6, the ambient noise microphone 12, and the CE sensor 8. The data are sampled in contiguous or partially overlapping segments. The signal processing of each segment is performed while the next segment is being acquired, so that there is a short delay, of a duration of less than one segment (approximately 50–100 ms), between the data acquisition and their presentation. Exceptions are the wheeze detection method and the snore detection method that compile data from more than one segment (approximately 3–5 segments) to verify the presence of the corresponding sounds.

Figure 7A:
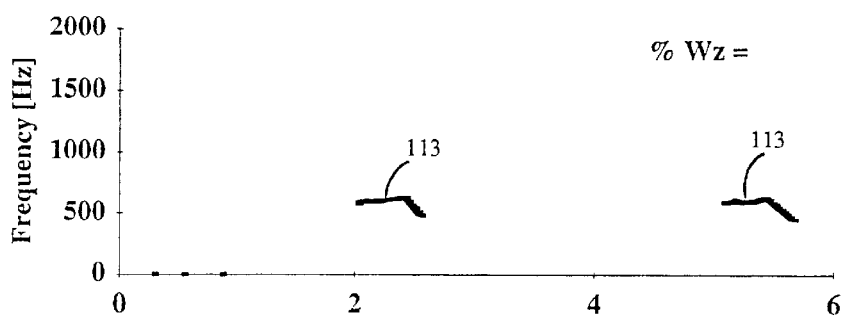
FIGS. 7A, 7B and 7C are graphs illustrating together an exemplary screen configuration of the PPG Monitor of FIG. 4.
Figure 7B:
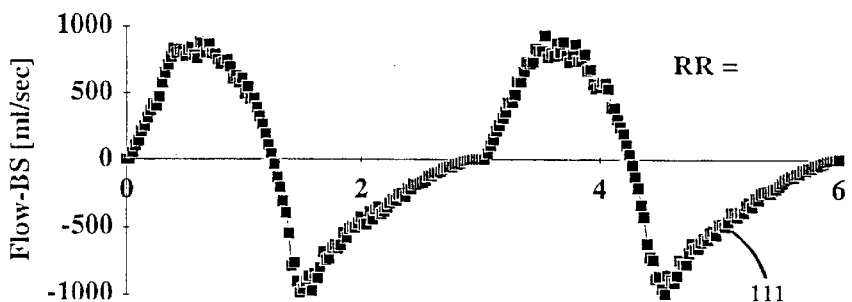
Figure 7C:
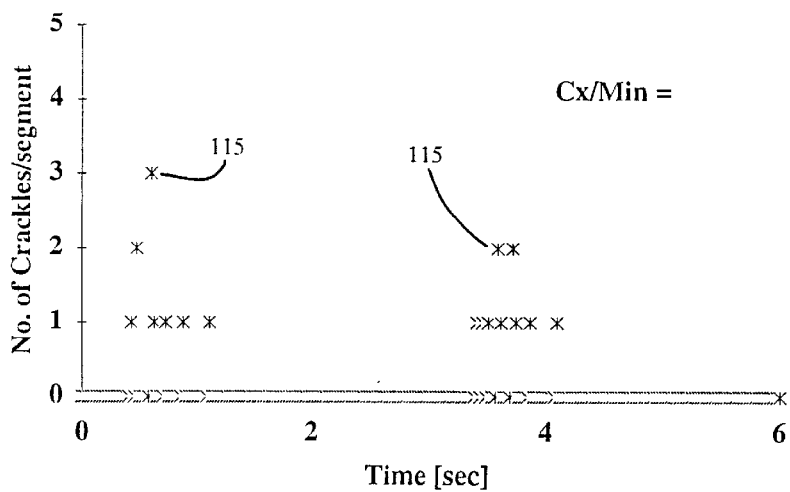

Reference is now made to FIGS. 7A, 7B and 7C which together illustrate an exemplary screen configuration of the PPG Monitor's display. Three graphs are shown simultaneously on the monitor's display in this exemplary screen configuration, the wheeze sonogram graph (FIG. 7A), the BS-based flow indicator graph (FIG. 7B) and the crackles per segment graph (FIG. 7C).

FIG. 7A illustrates the wheeze sonogram graph. The vertical axis represents the wheeze frequency and the horizontal axis represents time. The wheezes trace 113 indicates the presence of wheezes and shows the wheeze frequency as a function of time. The duration of wheezes compared with the total duration of active breathing (Twh/Ttot), labeled % Wz, is shown next to the wheeze sonogram traces 113. A color coding may be used to indicate the confidence level of the wheeze identification (which represents the degree of matching of the detected sound to the wheeze template). For example, a red color may represent absolute confidence, an orange color may represent "probable" wheeze detection, and a yellow color may represent "possible" wheeze detection.

FIG. 7B illustrates the flow indicator graph. The vertical axis represents the flow rate and the horizontal axis represents time. The flow indicator trace 111 shows the timing and regularity of breathing. When the breath state analyzer 50 is calibrated against a conventional flow-measuring device, such as a pneumotachograph, spirometer, or a mechanical ventilation apparatus, the PPG Monitor can also generate a quantitative measure of the flow amplitude. The respiratory rate, labeled RR, is given next to the flow indicator trace 111.

FIG. 7C illustrates the crackles per segment graph. The vertical axis represents the number of crackles per segment and the horizontal axis represents time. The graph displays the presence of crackles as vertically stacked marks 115, each mark representing the number of crackles detected in the segment. The number of crackles per minute, labeled Cx/Min, is shown next to the crackles per segment marks 115.

It is noted that the time axes of the three graphs of FIGS. 7A, 7B and 7C are synchronized on the display of the PPG Monitor so that the user can discern the timing of the crackles or wheezes that are detected within the respiratory cycle.

When excessive ambient noise is detected, the PPG Monitor indicates it by changing the background color of all the panels on the screen of display 28 and by not displaying the traces representing the detected breath sounds. The presence of a cough, rhonchi, or snores is indicated using specific icon notation on a separate strip displayed on the bottom of the breath detection (flow) panel (not shown).

Two types of alarm are used by the PPG Monitor, an absolute alarm signal and a relative alert signal.

An absolute alarm signal is generated when an apnea that is longer than a predetermined duration (approximately 6–10 seconds) is detected. A relative alert signal, which indicates a change in the sounds relative to the conditions during the most recent "training" period, is generated under the following circumstances:

a) Detection of wheezes that were not previously present.
b) A significant change (for example a 20% increase) in the duration of wheezes compared with their duration in the most recent "training" period.
c) Detection of crackles that were not previously present.
d) A significant change (for example a 20% increase) in the number of crackles per breath or per time unit compared with the most recent "training" period.
e) A significant change of the respiratory rate, for example a 20% increase or decrease.
f) The presence of secretion sounds (rhonchi or expiratory crackles).
g) Detection of an imbalance between the outputs of a plurality of sensors placed on the two opposite sides of the thorax. For example, an imbalance between the output of the left and right anterior chest sensors might be sensed.

Whenever an alarm or alert signal is issued, a specific explanatory text message is simultaneously displayed on the display 28.

According to a preferred embodiment of the present invention, the PPG Monitor, in addition to the evaluation of the data from each individual sensor as described hereinabove, includes a method by which an imbalance between sounds from different sites over the chest can be detected. In particular, detection of changes in the sounds detected on the left and right sides of the thorax in a patient who has been intubated by an endotracheal tube is important. Such changes may indicate a malposition of the tip of the tube to ventilate one of the lungs preferentially and not the other. To detect these changes, the PPG Monitor keeps a log of the parameters of the sounds from the two sides of the chest. Whenever an imbalance is suspected, the primary post-processor 56 (FIG. 2) calculates the transfer function of the sounds (magnitude, phase and coherence) between the two sites over the thorax and between the chest sites and the tracheal sensor.

Any significant change (increase or decrease) in the magnitude of the transfer function, phase or coherence relative to the "training" period is identified by the primary post-processor 56 and induces an alarm.

The spectral content of the basic breath sounds is continuously evaluated by the breath sounds analyzer 52 which performs a curve fit to a template equation and calculates a set of parameters from the best-fit equation disclosed in detail hereinafter. Any significant changes in the values of the parameters of the best-fit equation compared with their values obtained during the most recent "training" period are identified.

The PPG Recorder

We now return to FIG. 5 illustrating the PPG system of FIG. 2, configured as a PPG Recorder in accordance with a preferred embodiment of the present invention. The PPG Recorder includes the same BS sensors 4 and 6, the ambient noise microphone 12 and the CE sensor 8. Preferably, the BS sensors 4 and 6 are wireless contact sensors, the ambient noise microphone 12 is a wireless microphone and the CE sensor 8 is a wireless chest expansion sensor (FIG. 1) for reducing artifactual wire friction noises caused by patient movements during sleep.

The PPG Recorder also includes the remote receiver 16 of FIG. 1 (not shown in FIG. 5 for the sake of clarity of illustration) for receiving the signals from the sensors 4, 6 and 8 and the ambient noise microphone 12 and transmitting them to the analog signal conditioner/digitizer 18, where the signals are amplified, conditioned and digitized as described hereinabove. The data is then sent to the CPU 20 for on-line analysis as described hereinabove for the PPG System of FIG. 2.

The PPG Recorder can include the electronic stethoscope 14 of FIG. 1 for remote verification of sensor placement and adequate skin contact thereof.

The primary post-processor 56 receives the results of the data analysis for further processing and provides graphic presentations, parametric summaries, analyses of temporal trends, and histograms. The input parameters include information on each sound segment that include the following parameters, described in detail hereinafter, from each sound pick up location:

The time of day;

The environmental noise amplitude;

The amplitude of the tracheal sound signal;

Inspiratory, Expiratory, or Apnea segment designation [−/+/0];

Amplitude of the sound signal in this channel (RMS amplitude);

Parameters of the basic breath sound spectrum (Amplitude, $f_0$, slope);

Wheeze presence or absence in the segment;
If wheezes are present, Wheeze frequency (frequencies): $f_1$, $f_2$, $f_3$, . . . in segment;

Crackles presence or absence in the segment;
If crackles are present, number of crackles in segment;
If crackles are present, the parameters of best fit equation of each crackle;

Rhonchi presence or absence in segment;

Snore presence or absence in segment;
If snore is present in segment, the snore classification (simple/complex);

Cough presence in segment;

Transfer functions (if two or more sensors are used);

Magnitude, Coherence and phase.

The primary post processor 56 performs a short range, for example a minute-by-minute analysis, and a longer range analysis, for a selectable duration ranging from approximately 15 minutes to 24 hours. The short range analysis generates only numerical data on the last minute, for example, running minute, updated every 10 seconds. These analyses include the mean respiratory rate; the mean ratio of inspiratory and expiratory duration ($T_{insp}$; $T_{exp}$, respectively) to the total duration of active breathing ($T_{total}$) ($T_{insp}/T_{total}$ and $T_{exp/Ttotal}$, respectively); mean inspiratory and expiratory amplitudes ($A_{insp}$, $A_{exp}$, respectively); the total duration of wheezes (TWh) relative to the duration of active breathing ($T_{Wh}/T_{total}$); the duration of inspiratory wheezes to the active inspiratory duration ($T_{insp-Wh}/T_{insp}$);

the duration of expiratory wheezes to the active expiratory duration ($T_{exp\text{-}Wh}/T_{exp}$); the total number of crackles per minute ($N_{Cx}$); the number of inspiratory crackles per minute ($N_{insp\text{-}Cx}$); the number of expiratory crackles ($N_{exp\text{-}Cx}$); the duration of snores relative to the total duration ($T_{Snore}/T_{total}$); the number of coughs per minute ($N_{Cough}$); and an indication of ambient noise level. The primary post processor 56 also calculates inter-channel parameter relationships, frequency distribution (histograms) of the respiratory rate RR, the breathing amplitude VT and the minute ventilation $V_E$ and statistics of all the parameters, and sends the data to a data log stored in storage device 22. The primary postprocessor 56 is also connected to a secondary post-processor 63 for further processing of the data to the appropriate form for data logging and outputting in a suitable file format for creating a permanent record of the logged data on a removable data storage medium, such as a floppy diskette, a removable hard disk cartridge, a removable opto-magnetic disk or any other suitable removable data storage medium.

Additionally, the secondary post-processor controls the electronic transfer of data log files by receiving appropriate operator instructions through the user interface 32. The secondary post-processor also controls the printing of a PPG recorder report by a suitable printer.

The parameters of the analyzed breath sounds are stored as a data log in the data storage device 22.

The PPG Recorder can thus perform a continuous, quantitative evaluation of the breathing parameters and parameters of the adventitious sounds of sleeping patients with suspected nocturnal respiratory symptoms.

Reference is now made to FIGS. 8A and 8B illustrating two additional configurations of the PPG System of FIG. 2.

FIG. 8A illustrates a PPG System 70 constructed and operative in accordance with a preferred embodiment of the present invention. PPG System 70 includes a plurality of sensors 72 which are suitably attached to a patient's body as described hereinabove and illustrated in FIG. 1. The sensors 72 are suitably connected to an analog signal conditioner/digitizer 74 which amplifies, conditions and digitizes the sensors' signals as described hereinabove and sends the amplified and conditioned and digitized signals through a modem 76 to another remote modem 82. The modems 76 and 82 communicate either directly through the Public Switched Telephone Network (PSTN) or by using digital data packet switching protocols of a Wide Area Network (WAN).

The modem 82 is a part of a Telemedicine Center 80 and is connected to a CPU 84 which is a part of the Telemedicine Center's PPG System (the parts thereof are not shown for the sake of clarity of illustration). The CPU 84 performs the analysis of breath sounds as described hereinabove and illustrated in FIG. 2. Thus, the PPG system of the Telemedicine Center 80 can generate all the reports, alarms, alerts, and data-logging functions of any of the configurations of the PPG System of the present invention described hereinabove and illustrated in FIGS. 2–5.

FIG. 8B illustrates a PPG System 90 constructed and operative in accordance with an additional preferred embodiment of the present invention. The PPG System 90 includes a plurality of sensors 92 suitably connected to an analog signal conditioner/digitizer 94 for amplifying filtering and digitizing the signals of sensors 92. The PPG System 90 further includes a secondary CPU 96 suitably connected between the analog signal conditioner/digitizer 94 and a modem 98. The modem 98 communicates with a modem 102 through a suitable communication line 100. The modem 102 is also suitably connected to a primary CPU 104 which is a part of a Telemedicine Center 106. The secondary CP 96 performs a part of or all of the breath sound analysis as described hereinabove and illustrated in FIG. 2 and communicates the partially processed data or the completely processed data, respectively, to the primary CPU 104 of the Telemedicine center 106 where the data processing is completed and the data is logged or the completely processed data is logged, respectively.

It is noted that, in accordance with a preferred embodiment of the present invention, the analog breath sounds which are picked up by the sensors can be communicated using a telephone line to a telemedicine center where the received analog breath sounds are fed as input to a PPG system for further analysis.

It is further noted that either the primary CPU 104 or the secondary CPU 96 may be equipped with any of the combinations of the input or output devices described hereinabove and illustrated in FIGS. 1–5.

It is also noted that the sensors 72 and 92 of the PPG Systems 70 and 90, respectively, can be implemented as wired or wireless sensors in accordance with different preferred embodiments of the present invention.

It is still further noted that, in accordance with a preferred embodiment of the present invention, the data log recorded by the PPG recorder can be electronically transferred to a telemedicine center (FIG. 8B) by a modem using a direct modem-to-modem link or the digital data packet protocols of a wide area network (including the Internet). This feature has the advantage that the stored data log does not need to be physically transported on a removable storage medium and can be quickly available to a remotely located physician for immediate interpretation and use.

Breath Analysis Methods

Reference is now made to FIGS. 9, 11, 12, 15, 18 and 22, illustrating in detail the flow control and data processing steps of the breath analysis methods and the adventitious sound detection methods used by the PPG System in accordance with a preferred embodiment of the present invention.

The Breath Detection Method

The breath detection method accepts as input the signals picked up by the tracheal BS sensor 6 or 66, the ambient noise microphone 12 or 62 and the CE sensors 4 or 64 of the PPG Systems of FIGS. 1–5 and processes the signals to yield as output the following parameters: the breath flow rate, the times of onset of the inspiration and expiration phases of breathing, the breathing rate (breaths/time unit), the breath amplitude, the breathing regularity and the timing and duration of apnoea.

The breathing regularity is defined as: $(\sigma_{RR}/RR)\text{-}100$, where $\sigma_{RR}$ is the variance of the breathing rate and RR is the breathing rate.

The breath detection method also outputs control signals sent to the alert/alarm unit 34 of FIG. 1 (if appropriate to the specific configuration) for initiating a variety of alarms or alerts. The breath detection method also determines whether adventitious sounds will be searched for.

FIGS. 9A–9F comprise a schematic flow chart which outlines the details of the Breath Detection method.

Figure 9A:
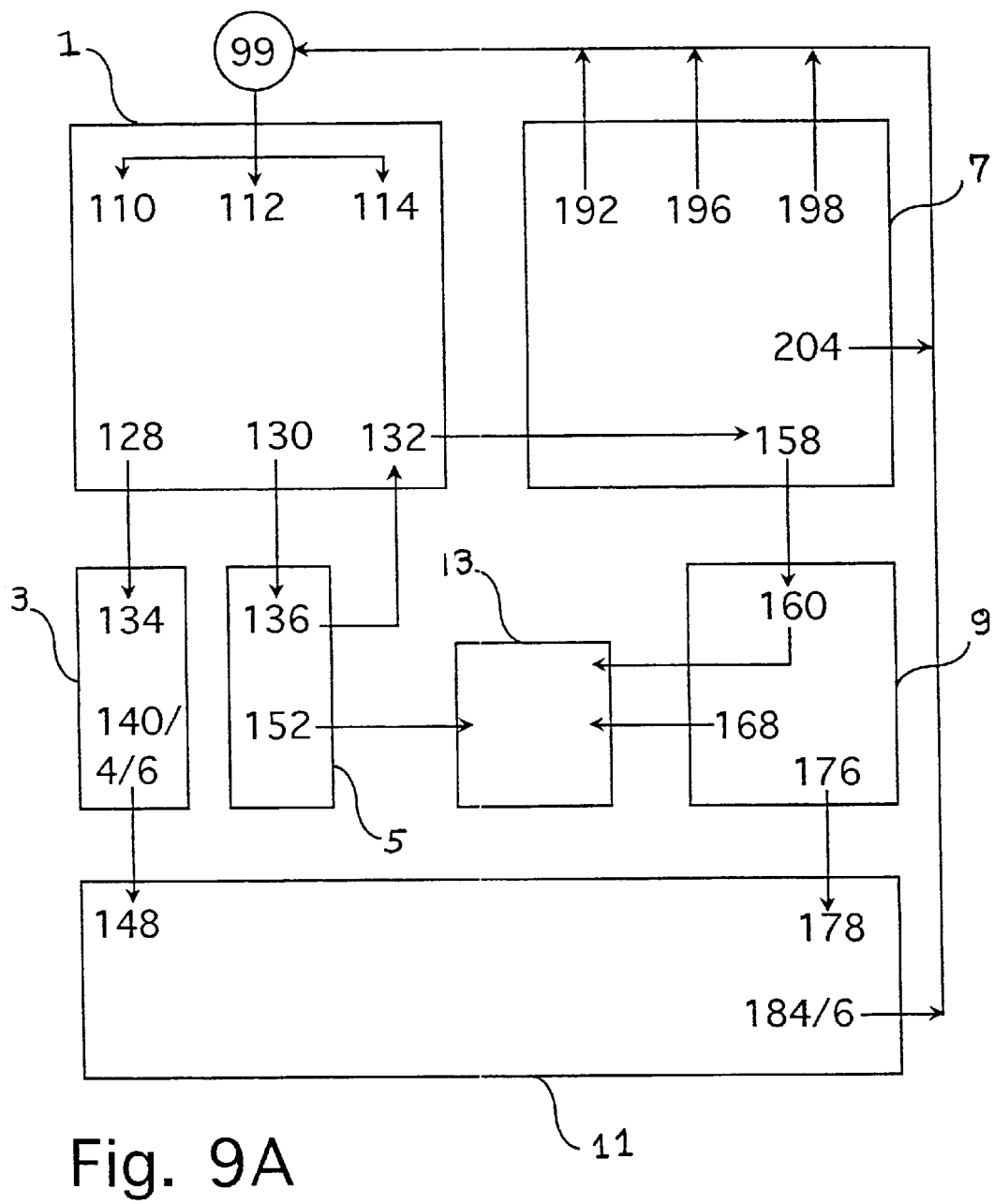
FIGS. 9A–9F comprise a flow chart which illustrates in detail the steps of a Breath Detection method in accordance with a preferred embodiment of the present invention.
Figure 9B:
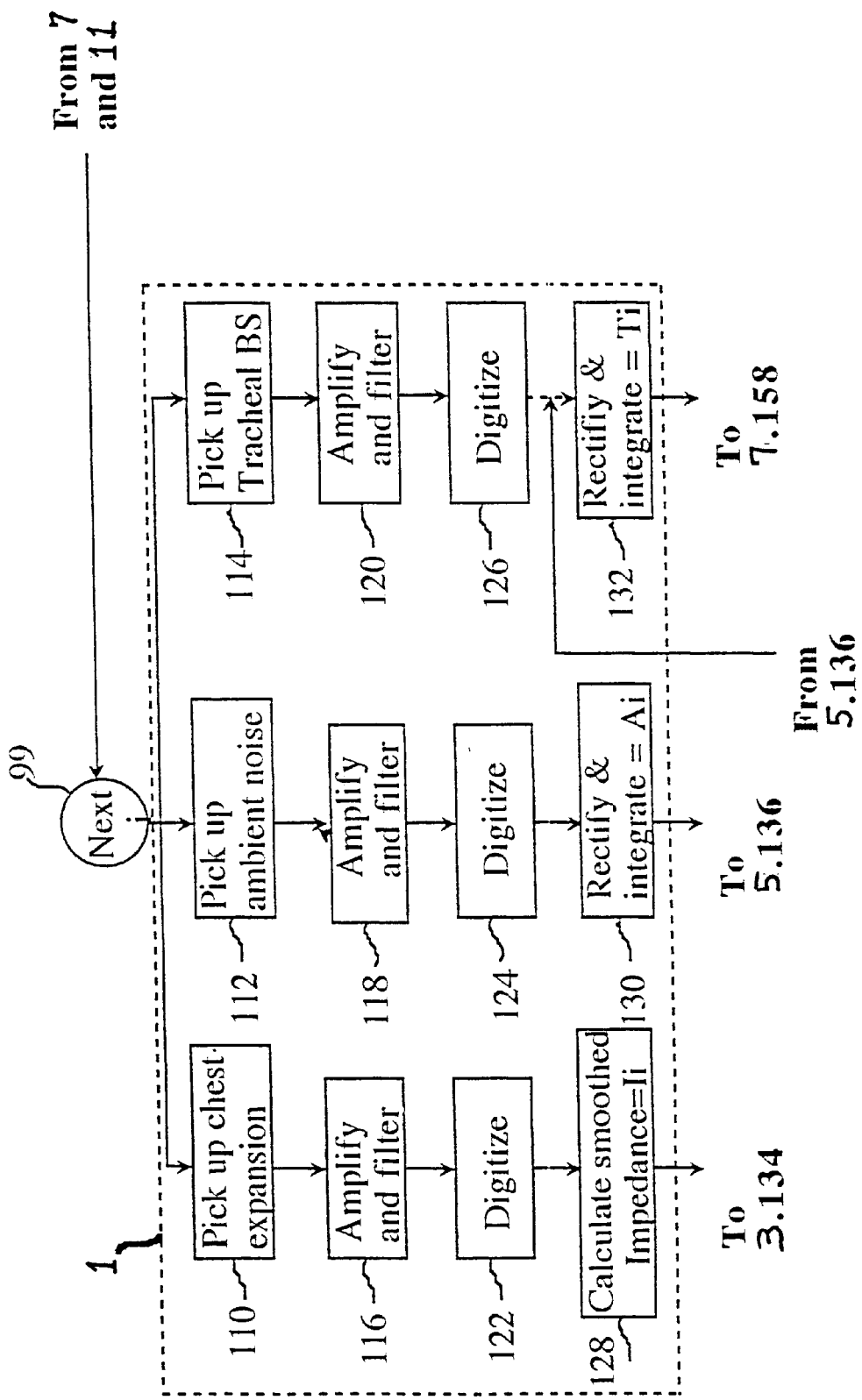
Figure 9C:
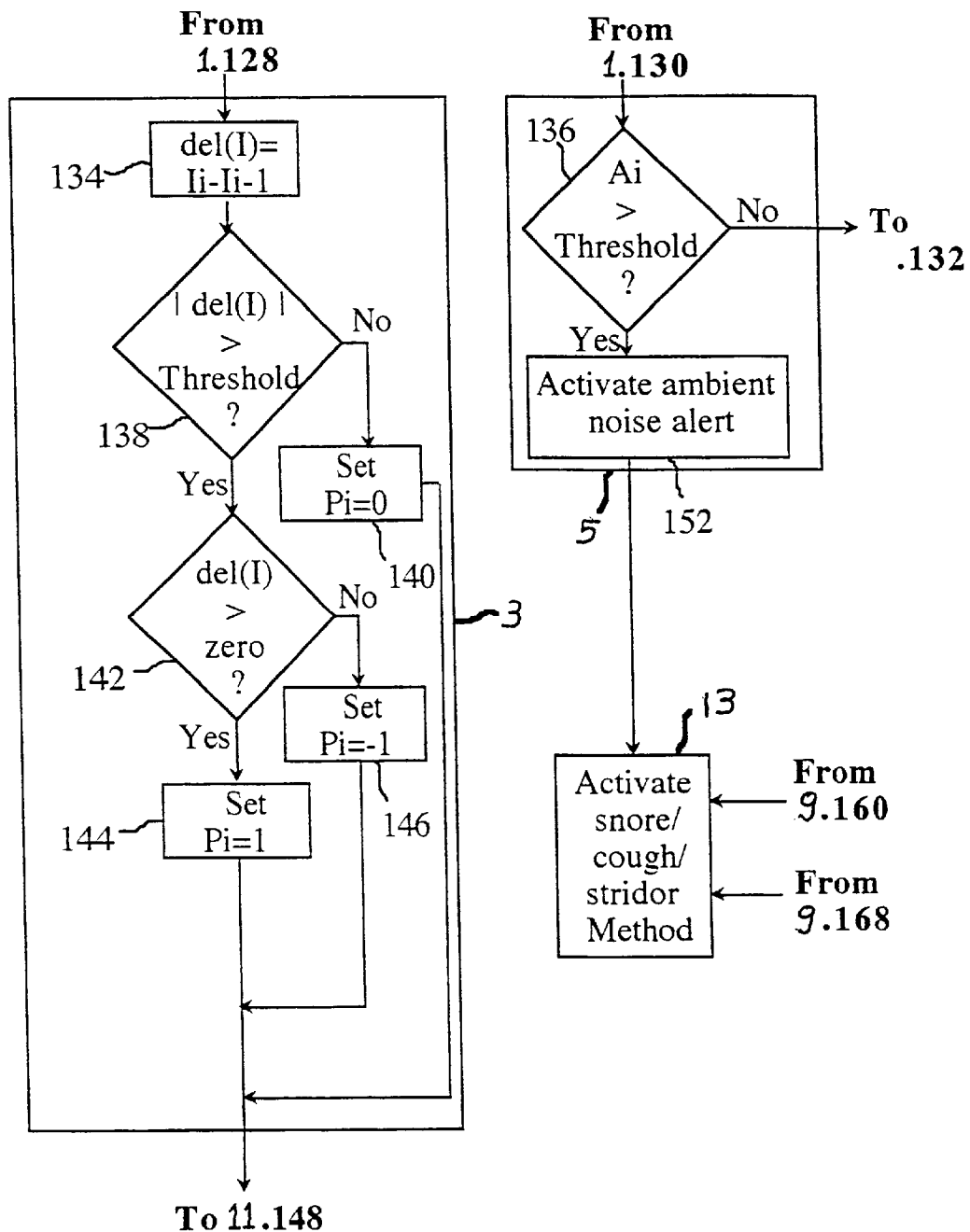
Figure 9D:
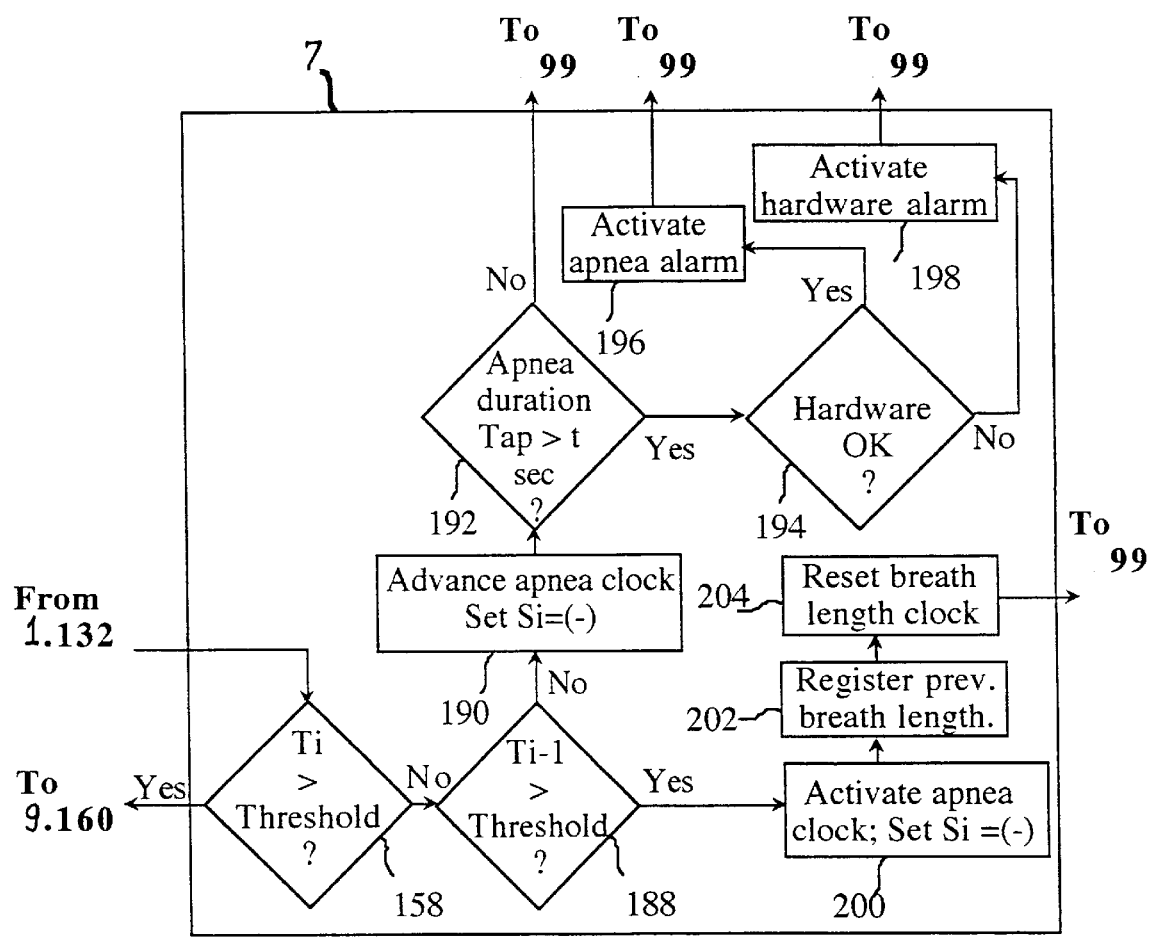
Figure 9E:
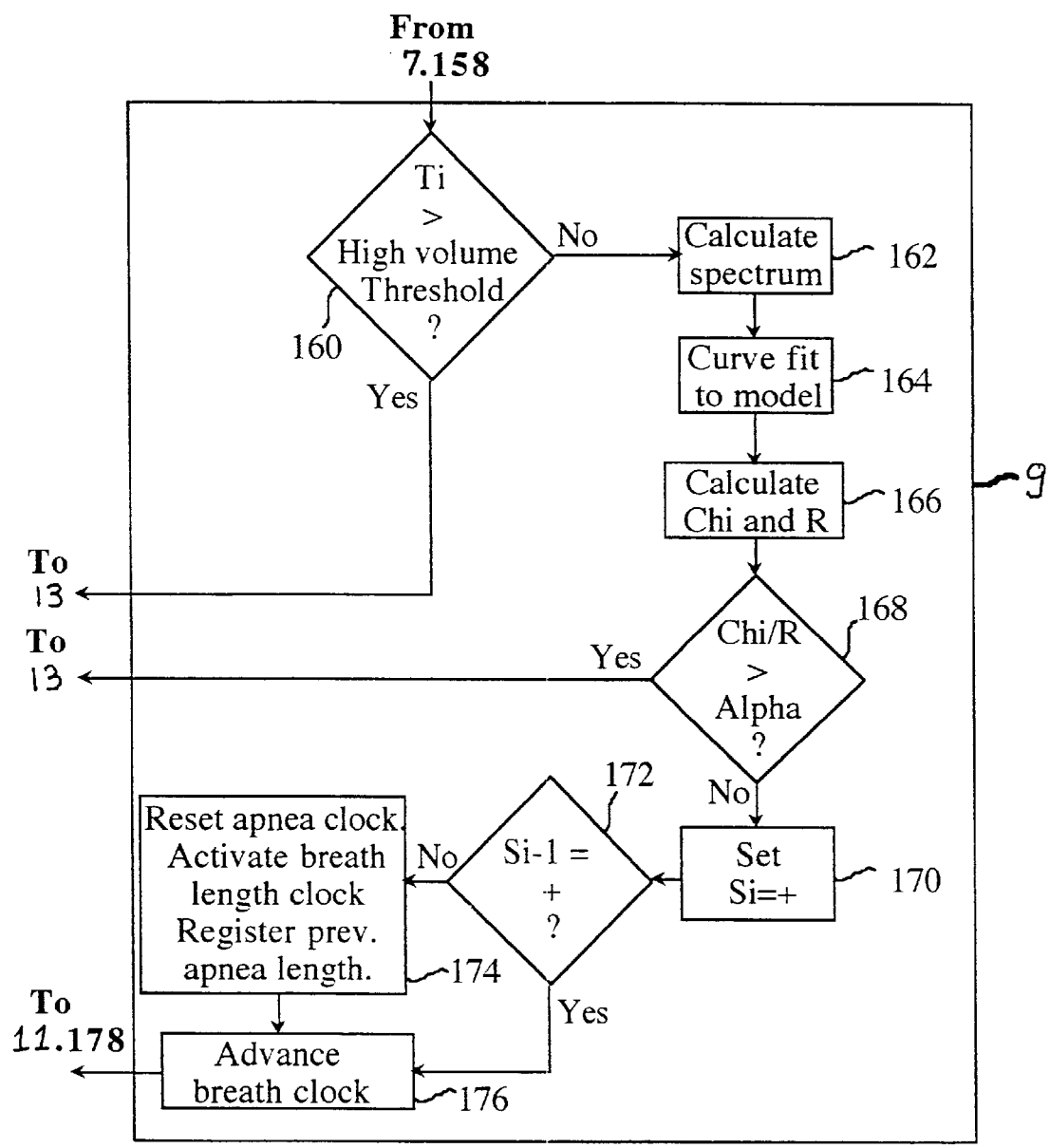
Figure 9F:
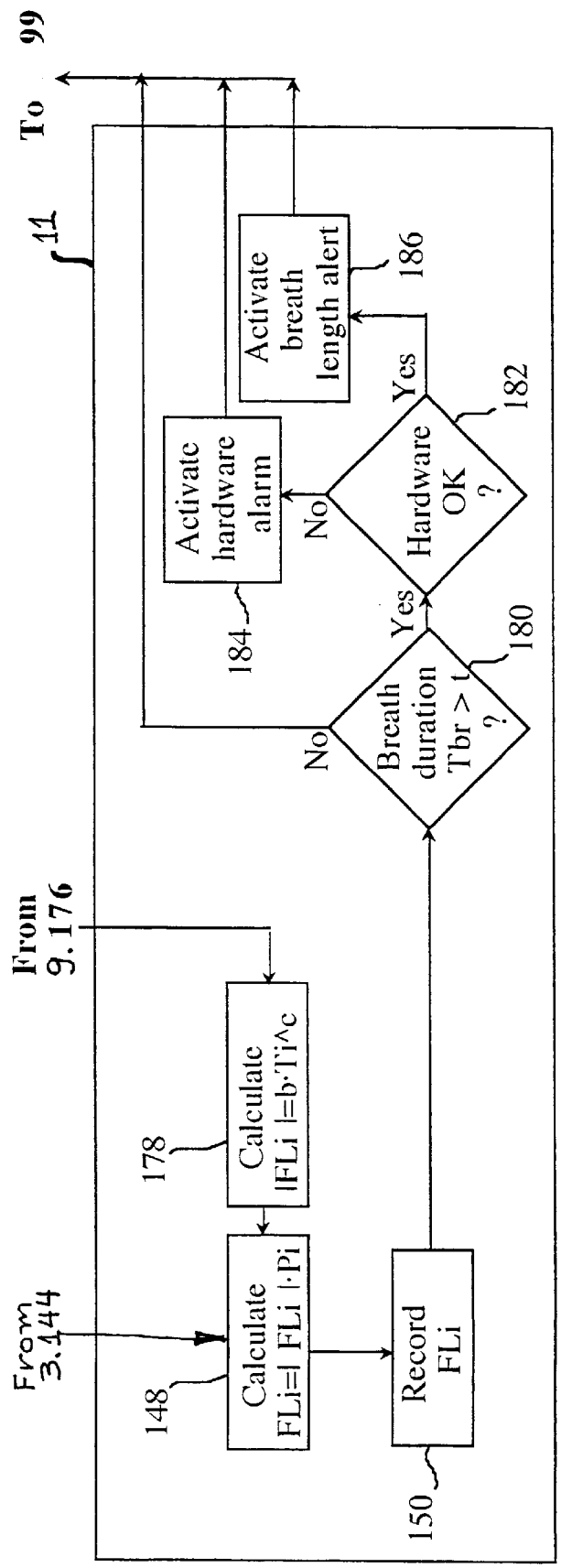

The Breath Detector method is divided into seven major blocks 1, 3, 5, 7, 9, 11 and 13. FIG. 9A shows the interrelation between these blocks, FIGS. 9B–9F show details of the blocks. Interconnections between the block are shown in FIG. 9A. Connections to other blocks, are shown in FIGS. 9B–9E using the code X.nm, where X is the block number and nm is the element number. The designation "FIG. 9", when used herein refers to the complex of FIGS. 9A–9F.

Block 1 picks up the analog signals of the BS and CE sensors and the ambient noise microphone, conditions and digitizes the signals and then performs channel specific conditioning operations on each of the individual digitized data segments.

The system picks up the chest expansion signal from the CE sensor 8 or 68 (step 110), amplifies the signal and band-pass filters it (step 116). The system then digitizes the signal (step 122) and integrates the signal for obtaining the integrated impedance parameter labeled $I_i$ (step 128) which is output to block 3.

It is noted that the chest expansion sensor can be any suitable CE sensor such as an electrical impedance sensor, an inductive plethysmograph, a magnetometer sensor, a flow sensor or a bellows sensor or any other sensor that can sense breathing movement.

The system also picks up the analog signal from the ambient noise microphone (step 112), amplifies the signal and band-pass filters it (step 118). The system then digitizes the signal (step 124) and rectifies and then integrates the signal for obtaining the rectified and integrated ambient noise parameter labeled $A_i$ (step 130) which is output to block 5.

The system also picks up the analog signal from the tracheal BS sensor (step 114), amplifies the signal and band-pass filters it (step 120). The system then digitizes the signal (step 126) and rectifies and then integrates the signal for obtaining the rectified and integrated tracheal breath sound amplitude parameter labeled $T_i$ (step 132) which is output to block 7.

Block 5 analyzes the noise level and controls the further processing of the data segments by the system.

Block 5 receives the parameter $A_i$ from step 130 and compares it to a preset or adaptive noise threshold value (step 136). If $A_i$ is larger than the noise threshold value, the system generates an ambient noise alert (step 152) and diverts control to block 13 which analyzes the ambient noise for acoustic characteristics of a snore, cough or stridor sound that may be generated by the patient. If $A_i$ is smaller or equal to the noise threshold value, the system proceeds with the analysis of the tracheal breath sounds by transferring control to step 132 of block 1.

In block 7, the system first compares the $T_i$ parameter to a preset or adaptive breath amplitude threshold (step 158). If $T_i$ is larger than the breath sound amplitude threshold, the segment is identified as a potential breath and control is transferred to block 9. If $T_i$ is not larger than the breath sound amplitude threshold, the segment is identified as an apnea segment. The system then checks whether this segment is the first segment in a sequence of apnea segments by comparing the value of the amplitude parameter $T_{i-1}$ of the previous segment to the breath amplitude threshold (step 188). If $T_{i-1}$ is larger than the breath sound amplitude threshold, this means that the current segment (segment i) is the first in a new sequence of apnea segments and the system activates the apnea clock (step 200), registers the previous breath length (step 202), resets the breath length clock (step 204) and returns to step 99 for sampling the next segment. If $T_{i-1}$ is not larger than the breath amplitude threshold, this means that the previous segment was also an apnea segment and the system advances the apnea clock (step 190). The system then checks the value of the apnea duration $T_{ap}$ (step 192). If $T_{ap}$ is not longer than a preset time threshold (operator determined with a preset default value), the system returns to step 99. If $T_{ap}$ is longer than the preset time threshold, the system runs a brief hardware verification (step 194) as described in detail hereinafter. If no hardware malfunction is detected, the system initiates an "apnea alarm" and returns to step 99. If the system detects a hardware failure, it initiates a "hardware alarm" (step 198) and returns to step 99.

Block 9 receives the $T_i$ value as input and checks its amplitude. In case of excessive amplitude it transfers control to block 13 for detection of possible snores, cough, stridor or vocalization. Otherwise, the block analyzes the segment's spectrum and determines whether the segment is to be identified as a valid tracheal breath sound segment.

Block 9 receives $T_i$ from step 158 and compares it to a preset or adaptive high-volume threshold (step 160). If $T_i$ is larger than the high-volume threshold, control is transferred to block 13 for further analyzing of a potential snore, cough, stridor or vocalization.

If $T_i$ is not higher than the high-volume threshold, the system continues to evaluate the segment by calculating the segment's spectral pattern (step 162).

Step 162 includes a determination of the spectral pattern calculated by fast Fourier transform (FFT) or from the autoregressive (AR) or autoregressive, moving average (ARMA) coefficients of the segment. The system then verifies that the spectral pattern of the segment corresponds to the known pattern of tracheal BS. This is done preferably by fitting the data to equation 1 (step 164):

$$y = \sum_{i=1}^{n} \frac{m_{1i} \cdot f}{\sqrt{m_{2i} \cdot f^2 + (m_{3i}^2 - f^2)^2}} \quad n = 3 \pm 1 \tag{1}$$

wherein $m_{1i}$ is a set of amplitude coefficients, f is the frequency, $m_{2i}$ is a set of damping coefficients, $M_{3i}$ is the set of resonance frequencies, i is the serial number of the resonance frequencies and n is the total number of resonance frequencies (n=3±1).

Alternatively, the system can verify that the spectral pattern of the segment corresponds to the known pattern of tracheal BS, by mapping the zeroes and poles of the actual segment relative to the known distribution for tracheal BS.

Figure 10:
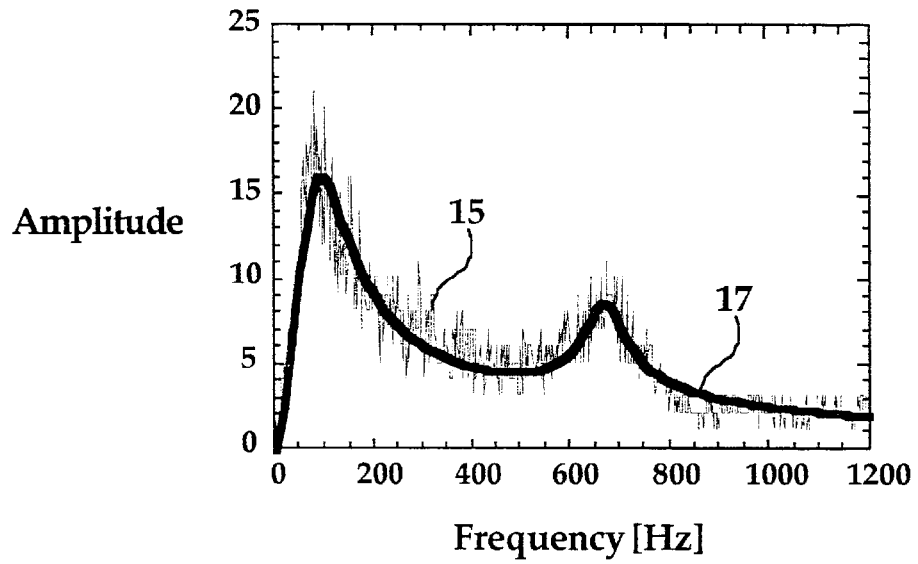
FIG. 10 which is an exemplary graph illustrating the results of curve fitting of the tracheal breath sound in accordance with a preferred embodiment of the present invention.

Reference is now made to FIG. 10 which is an exemplary graph illustrating the results of curve fitting of the tracheal breath sound. Curve 15 represents the spectrum of tracheal BS and curve 17, superimposed on curve 15, represents the best fit line 17, calculated from equation 1 for n=2. The horizontal axis represents the frequency and the vertical axis represents the amplitude. The system calculates goodness-of-fit coefficients–$Chi^2$ and regression coefficient R (step 166). The system evaluates the match of the signal to the model of equation 1 (step 168). If the match is below predetermined acceptability thresholds, for example if Chi/R>Alpha, where Alpha is a preset or adaptive goodness-of-fit threshold, for example Alpha=10, the system determines that this segment is not a tracheal breath sound segment and diverts control to block 13 for evaluating the acoustical characteristics of a possible snore, cough, stridor or vocalization. If the match is good, for example when Chi/R is not larger than Alpha, the system identifies the segment as representing tracheal breath sounds and assigns a logical (+) value to the segment parameter $S_i$ (step 170). The system checks if the current segment is the first in a sequence of breath-representing segments by checking the value of the previous segment parameter $S_{i-1}$. If $S_{i-1}$ is not a logical (+), the system records the duration of the apnea that just ended, resets the apnea duration clock and activates the breath length counter (step 174). The system then advances the breath duration clock (step 176) and transfers control to block 11. If the current segment is not the first in a sequence that represents breathing (e.g. the parameter $S_{i-1}$ is not a logical (+)), the system advances the breath duration clock (step 176) and transfers control to block 11.

Blocks 3 and 11 determine the respiratory phase and the flow amplitude, respectively. Block 3 receives the smoothed impedance parameter $I_i$ of the CE sensor (or any qualitative chest expansion or flow detector) from step 128. The system calculates the first derivative of the smoothed CE signal, for example by calculating the difference between the parameter $I_i$ of the current segment and of the parameter $I_{i-1}$ of the previous segment (step 134). The difference is calculated as $del(I)=I_i-I_{i-1}$. The system evaluates del(I) for its absolute magnitude |del(I)| and for its sign (step 138). If |del(I)| is smaller than a threshold value, which was determined during the "training" period, the chest is not moving and the segment is identified as a breath-hold and a breath phase parameter $P_i$ is set to zero (step 140). If |del(I)| is larger than the threshold, the segment represents breathing. If del(I) is positive the system designates the segment as expiratory and sets the value of $P_i$ to +1 (step 144). If del(I) is negative, the system designates the segment as inspiratory and sets $P_i$ to −1 (step 146).

Block 11 receives the values of $P_i$ and $T_i$ as input from blocks 3 and 9, respectively, and calculates the segment flow amplitude $FL_i$ by using the equation $|FL_i|=b \cdot T_i^c$, where $|FL_i|$ is the absolute value of the flow, b is a calibration factor and c is a calibration exponent determined during the "training" period (step 178). Exemplary values of the calibration factor and the calibration exponent are $b=10^{0.5}$ and $c=0.57$. The system then calculates the segment flow amplitude by using the equation $FL_i=|FL_i| \cdot P_i$ (step 148). The value of $FL_i$ is recorded for further use (step 150).

It is noted that the value of the calibration exponent c can be determined by a calibration procedure in which the patient breathes into a suitable quantitative flow measuring device, such as a pneumotachograph or a respirometer.

The system then performs an additional evaluation of the breath length parameter $T_{br}$ (step 180). If $T_{br}$ is longer than a pre-determined duration of t seconds, for example t equals three times the value of $T_{br}$ determined in the "training" period, the system performs a hardware check (step 182). If no hardware malfunction is detected, the system generates a breath duration alert (step 184) and transfers control to step 99. If a hardware malfunction is detected the system generates a hardware failure alarm (step 186) and the system transfers control to step 99 for the pick up and evaluation of a new segment.

It is noted that, in accordance with a preferred embodiment of the present invention, the system will use a "training period" to determine values for some of the parameters and indices stated above. In particular, the training period will be used to run the hardware testing procedure, to determine threshold values for $T_i$ and $A_i$, and to obtain reference values of breath and apnea durations. In addition, the system also evaluates the values of the tracheal sound resonance frequencies. The tracheal sound resonance frequencies are indicative of the respiratory system's integrity. For example, these frequencies might show a significant change in cases like pneumothorax or blockage of a major airway. The use of the "training" period has the advantage of improving the speed of calculation and the accuracy of detection of the system.

It is noted that the breath detector method is used by the PPG system of the present invention, including the PPG Monitor, Meter and Recorder, but can also be used as a "stand-alone" apnea monitor in clinically relevant situations (sleep apnea diagnosis and follow-up, servo information for nasal CPAP treatment or upper airway electrical stimulation, apnea monitoring of infants and senior citizens, and more). The breath detection method can also be used to detect breathing abnormalities in individuals who are involved in high risk occupations or environments, for example, undersea divers, astronauts, and miners.

The Breath Sound Analyzer Method

Figure 11D:
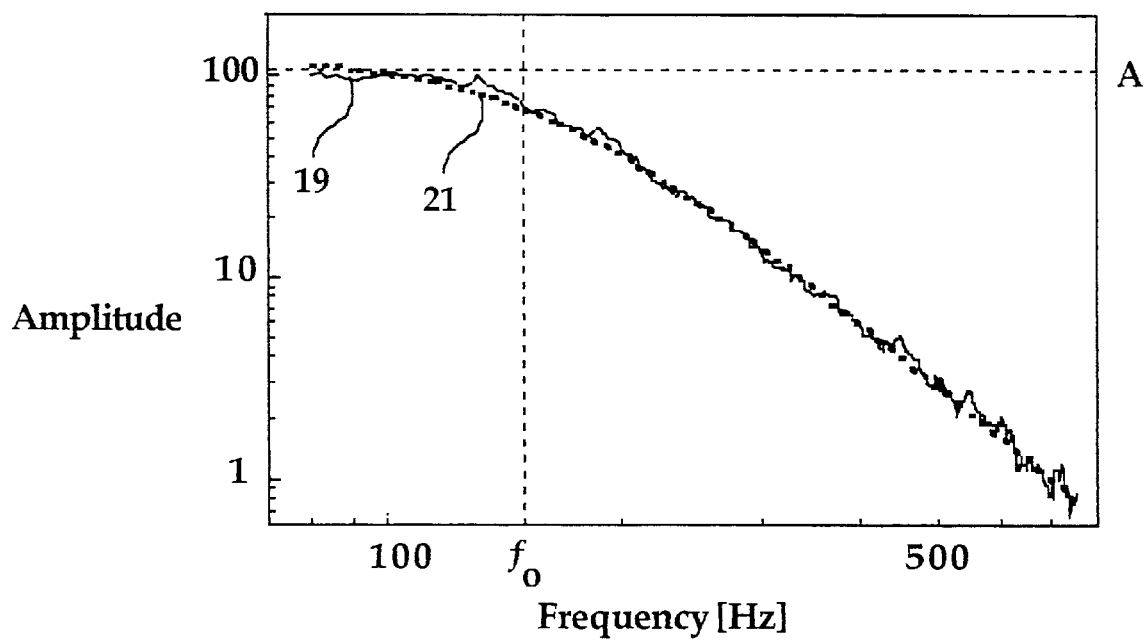
FIG. 11D is an exemplary graph illustrating the results of the curve fitting of the chest breath sound power spectrum in accordance with a preferred embodiment of the breath sounds analyzing method of the present invention.
Figure 11A:
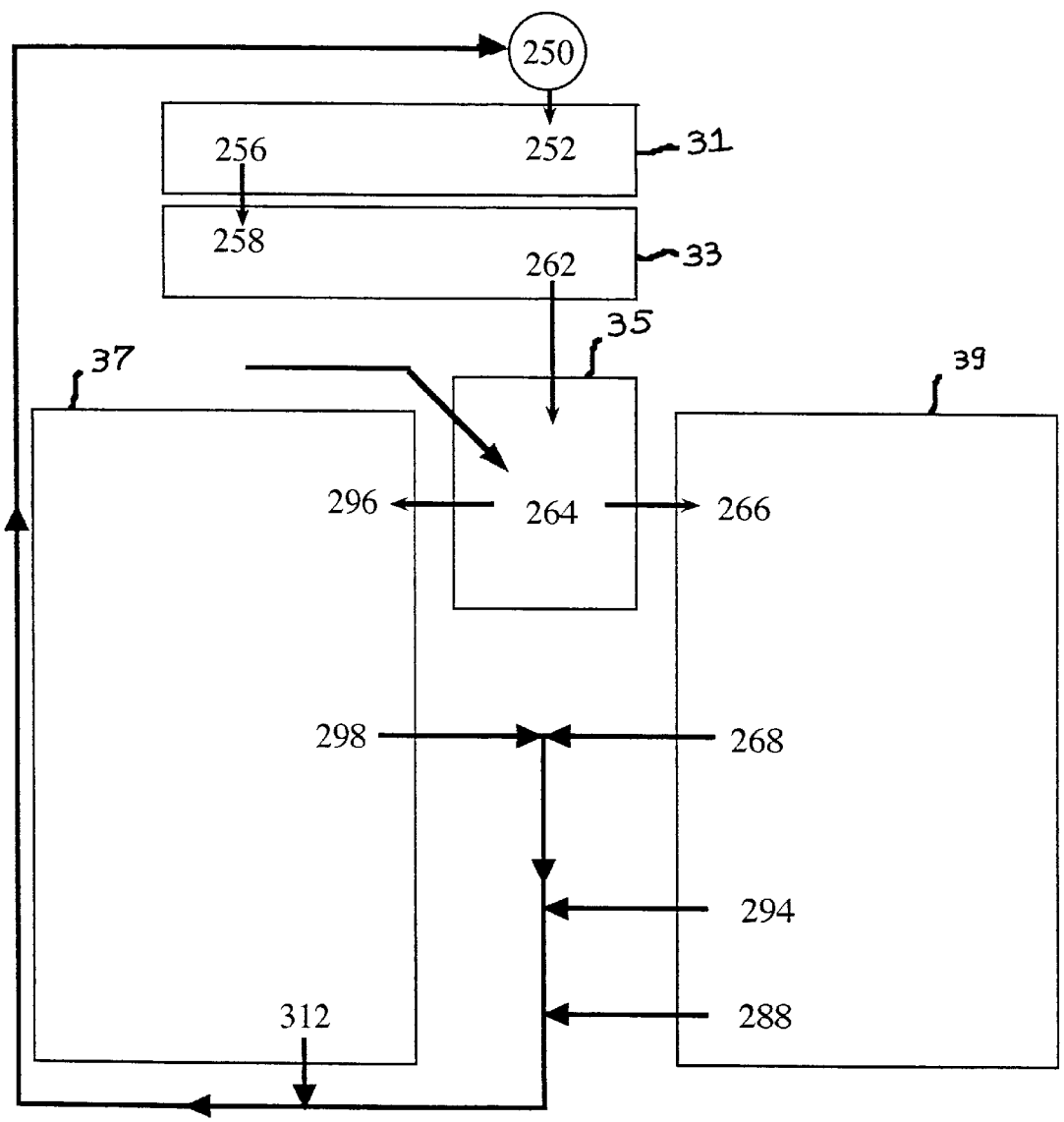
FIGS. 11A–11C comprise a flow chart illustrating in detail the steps of the breath sound analyzing method of the PPG system of FIGS. 1 and 2 in accordance with a preferred embodiment of the present invention.
Figure 11B:
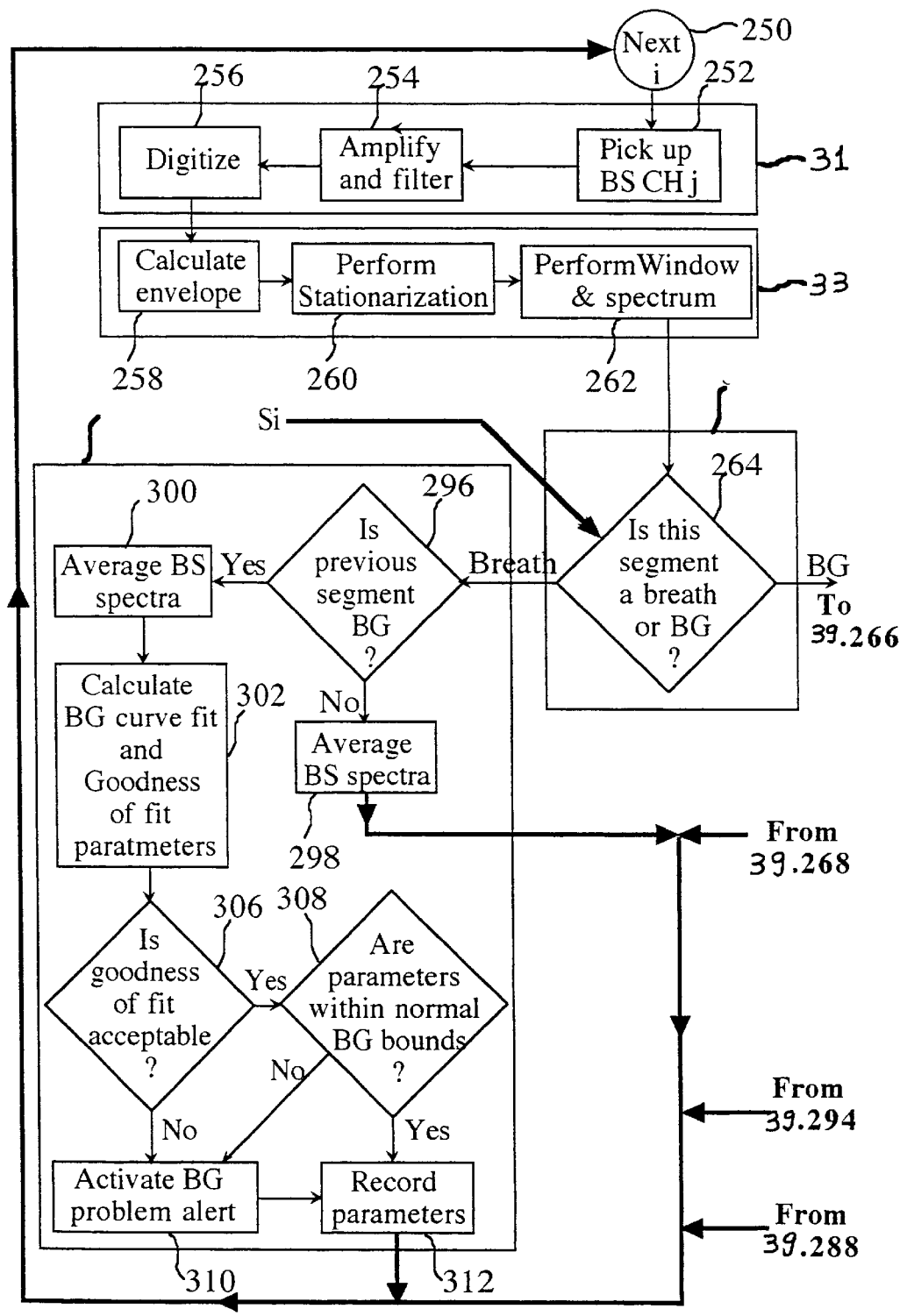
Figure 11C:
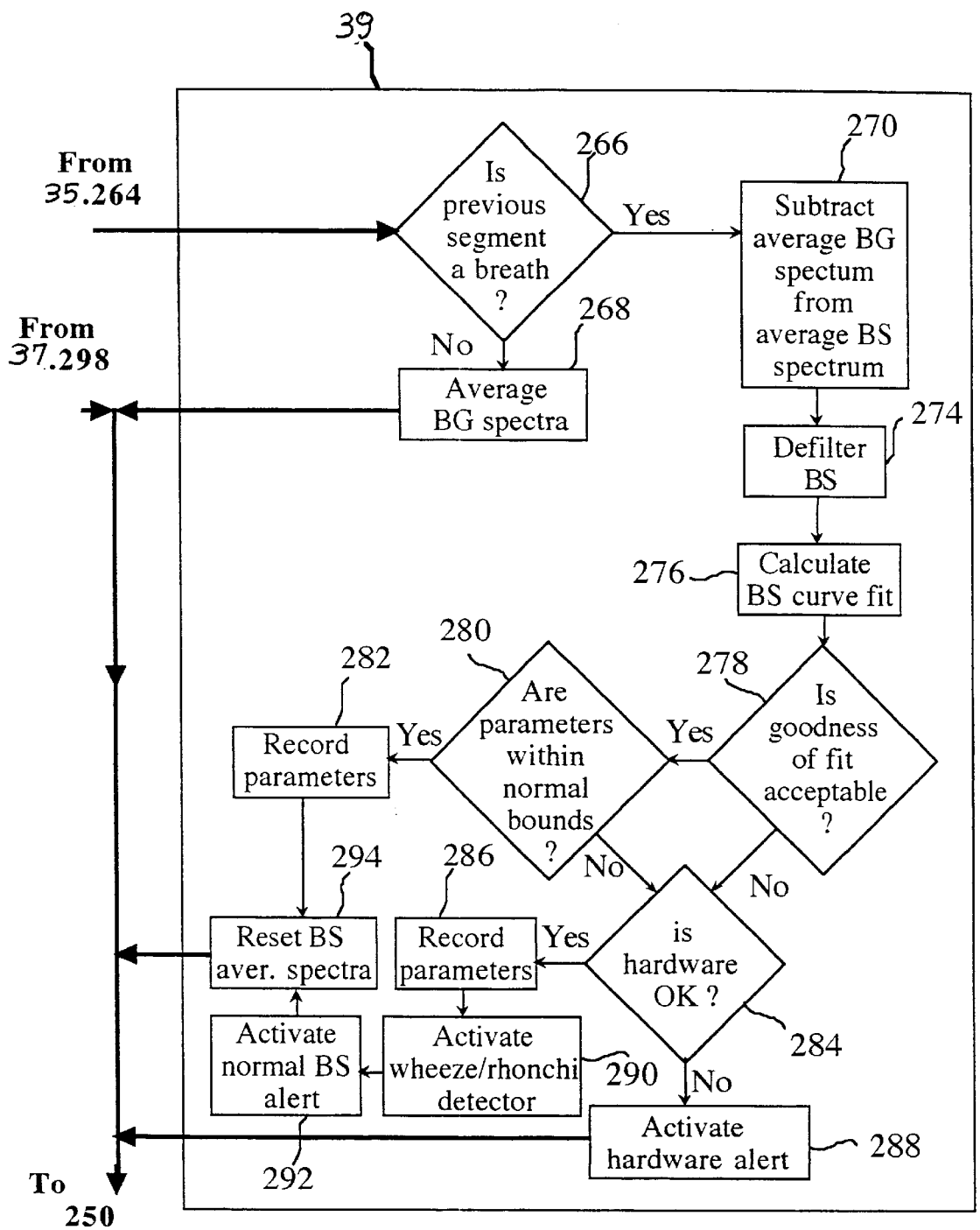

Reference is now made to FIGS. 11A–11C which illustrate the breath sound analyzer method in detail.

The breath sound analyzer includes blocks 31, 33, 35, 37 and 39. FIG. 11A shows the interrelation between these blocks, FIGS. 11B–11C show details of the blocks. Interconnections between the block are shown in FIG. 11A. Connection to other blocks, are shown in FIGS. 11B–11C using the code X_nm, where X is the block number and nm is the element number. The designation "FIG. 11A", when used hereinafter refers to the complex of FIGS. 11A–11C.

Block 31 receives the signals picked up by chest wall BS sensors (step 252), amplifies and filters the analog signal (step 254) and digitizes it, as described hereinabove, to yield a data segment (step 256).

Block 33 receives the digitized segment and calculates the magnitude of the spectrum by first calculating the envelope of the time domain signal (step 258). The system then performs a stationarization of the segment data by normalizing the signal to its envelope (step 260). The system normalizes the segment data by multiplying it by a window function, for example, a Hanning or Blackman window function and calculates the amplitude spectrum of the segment (step 262).

Block 35 checks whether the data segment is a breath or a background (breath hold) segment by checking the sign of the parameter $S_i$ which it receives from step 170 of block 9 of the breath detector method of FIG. 9 (step 264). If $S_i$ is negative, block 35 diverts control to block 39 for further processing. If $S_i$ is positive block 35 diverts control to block 37 for further processing. If the current segment is identified as a breath segment block 37 checks the previous segment (step 296). If the previous segment is not a background segment, this indicates that the current segment is not the beginning of a new breathing phase and the system averages the current BS segment's amplitude spectrum with the previous ones after denormalizing the data for the stationarization factor (step 298), and transfers control to step 250 for sampling the next segment. If the previous segment is a background segment, this indicates that the current segment is the beginning of a new breathing phase. The system stores the current BS spectrum for averaging (step 300) and proceeds to evaluate the preceding background (breath hold) phase by calculating the curve fit parameters of the averaged background amplitude spectrum of the preceding background phase segments (step 302) and checking the goodness of fit to a model equation which is empirically found to be a good representation of the amplitude spectrum of the background sound (step 306).

The model equation used to calculate the curve fit of the background data is equation 2:

$$y = \frac{A}{1+(f/f_o)^s} \quad (2)$$

wherein:

A=Spectrum's amplitude at the plateau $f_0$=Spectrum's curve deflection point

S=The spectrum's power. (S should be multiplied by 6.02 to get the slope in dB/oct, for example, slope=3.6× 6.02=21.6 dB/oct).

The system evaluates the fit parameters Chi$^2$, R and their ratio relative to a threshold. The threshold can be a preset threshold, for example the threshold value can be 10, or can be determined by the system during the "training" period. If the goodness of fit is acceptable, the system checks whether the values of A, $f_0$, and S are within a certain range of values which is empirically determined from average fit parameters of normal background data of patients (step 308), If the fit parameters are within the normal range, the system records the parameters A, $f_0$, S and Chi$^2$/R (step 312) and transfers control to step 250 for sampling the next segment. Typical values of the parameters for background sounds as obtained with a PPG system using a contact sensor as disclosed by the present inventor in U.S. patent application Ser. No. 08/654, 643 filed on May 29, 1996 and entitled "A Contact Sensor for Body Sounds", are: $f_0$=120 Hz and S≈25 dB/octave. The value of A depends on the gain of the PPG system.

If the goodness of fit is unacceptable or the parameters A, $f_0$, and S are not within the normal range, the system generates a background problem alert (step 310) and then records the parameters A, $f_0$, S and Chi$^2$/R (step 312) and transfers control to step 250 for sampling the next segment.

If block 35 identified the current segment as a background segment, block 39 checks if the previous segment was a breath or a background segment (step 266). If the previous segment was a background segment, this indicates that the breath hold phase is not yet ended and the system averages the current background segment's amplitude spectrum with the previous ones after denormalizing the data for the stationarization factor (step 268). The system transfers control to step 250 for sampling the next segment. If the previous segment was a breath segment, this indicates that a new breath hold phase has begun and the system proceeds to analyze the accumulated averaged BS spectra. The system initially subtracts the average background spectrum of the n previous segments from the BS spectrum (step 270). This step is done in the linear frequency domain by arithmetic subtraction. If the result of the subtraction is less than a specific value determined by the specifications of the A/D converter, for example 0.5·(amplitude resolution), the system eliminates the point. If more than a specific number of successive points, for example 3 points, are less than the threshold, the frequency of the first such point is designated $f_{max}$ and recorded.

The system then performs a defiltration operation to compensate for the effect of the high pass filter on the sound (step 274). The defiltration is done by dividing each data point by the frequency response of the filter or by the reconstructed response from the best-fit parameters of the filter. The best fit regression equation for this step is equation 3:

$$y = \frac{Gain}{1+(\text{``3dB}point\text{''}/f)^{Rolloff/6.02}} \quad (3)$$

where Gain is the amplification factor of the filter, 3 dB point is the deflection point of the filter and Rolloff is the slope of the filter in dB/octave.

The system then analyzes the spectral pattern of the averaged BS spectrum (step 276). The analysis is done by calculating the best fit of the BS signal to the equation 4:

$$y = \frac{A}{1+(f/f_o)^s} \quad (4)$$

wherein:

A=amplitude at the plateau $f_0$=deflection point

S=power (S should be multiplied by 6.02 to get the slope in dB/oct, for example 3.6×6.02=21.6 dB/oct).

Reference is now made to FIG. 11D illustrating a graph demonstrating the results of the curve fitting of equation 4 of the chest breath sound power spectrum. The vertical axis of the graph represents amplitude and the horizontal axis represents frequency. The curve 19 represents the power spectrum of the defiltered data picked up by a chest contact sensor of the PPG system of FIG. 1. The value of the spectrum's amplitude at the plateau is indicated by the horizontal dashed line, labelled A, and the value of the spectrum's curve deflection point (3 dB point) is indicated by the vertical dashed line, labelled $f_0$. The curve marked 21 represents the curve fitted to the data using the model equation 4.

The system evaluates the fit parameters Chi$^2$, R and their ratio Chi$^2$/R, relative to preset or adaptive thresholds (step 278). If the goodness of fit is acceptable, for example if (Chi$^2$/R)<10, the system checks whether the values of A, $f_0$, and S are within a certain range of values which is empirically determined from average fit parameters of normal breath sound data of patients (step 280), If the fit parameters are within the normal range, the system records the parameters A, $f_0$, S and Chi$^2$/R (step 282), resets the BS averaged spectrum (step 294) and transfers control to step 250 for sampling the next segment. If the goodness of fit is unacceptable or the parameters A, $f_0$, or S are not within the normal range, the system performs a hardware check (step 284). If the hardware is found to malfunction, the system generates a hardware alert (step 288) and transfers control to step 250. If no hardware malfunction found, the system records the parameters A, $f_0$, S and Chi$^2$/R (step 286), transfers control to the wheeze/rhonchi detection method (step 290), generates an abnormal BS alert (step 292), resets the BS average spectrum (step 294) and transfers control to step 250 for sampling the next segment.

It is noted that the typical values of the parameters $f_0$ and S vary for men, women and children and can also vary for different sensor locations. Additionally, the typical values of the parameters $f_0$ and S can be different for inspiratory and expiratory breath sounds. Exemplary ranges are $f_0$=175 Hz±25 Hz, with an average value of approximately 175 Hz for adult males, approximately 182 Hz for adult females and 235±35 Hz for children. An exemplary range for the slope is S=18±4.5 dB/Octave. A is a system specific parameter which depends on the gain of the system and on the loudness of the breath sounds.

It is noted that the method of fitting the BS power spectrum data to equation 4 yields better results (better fit)

than the prior art method of fitting the BS power spectrum data to two straight lines as disclosed by the present inventor in the book *Breath Sounds Methodology* by Noam Gavriely, CRC Press Inc, 1995.

It is also noted that, from equation 4 and the values of A, $f_0$ and S, it is possible to derive other descriptive parameters of BS such as median frequency, quartile frequencies, for example frequencies of 25%, 50% and 75% of power and percentile frequencies, for example 95% of power or 99% of power frequencies.

The Wheeze Detection Method

Figure 12:
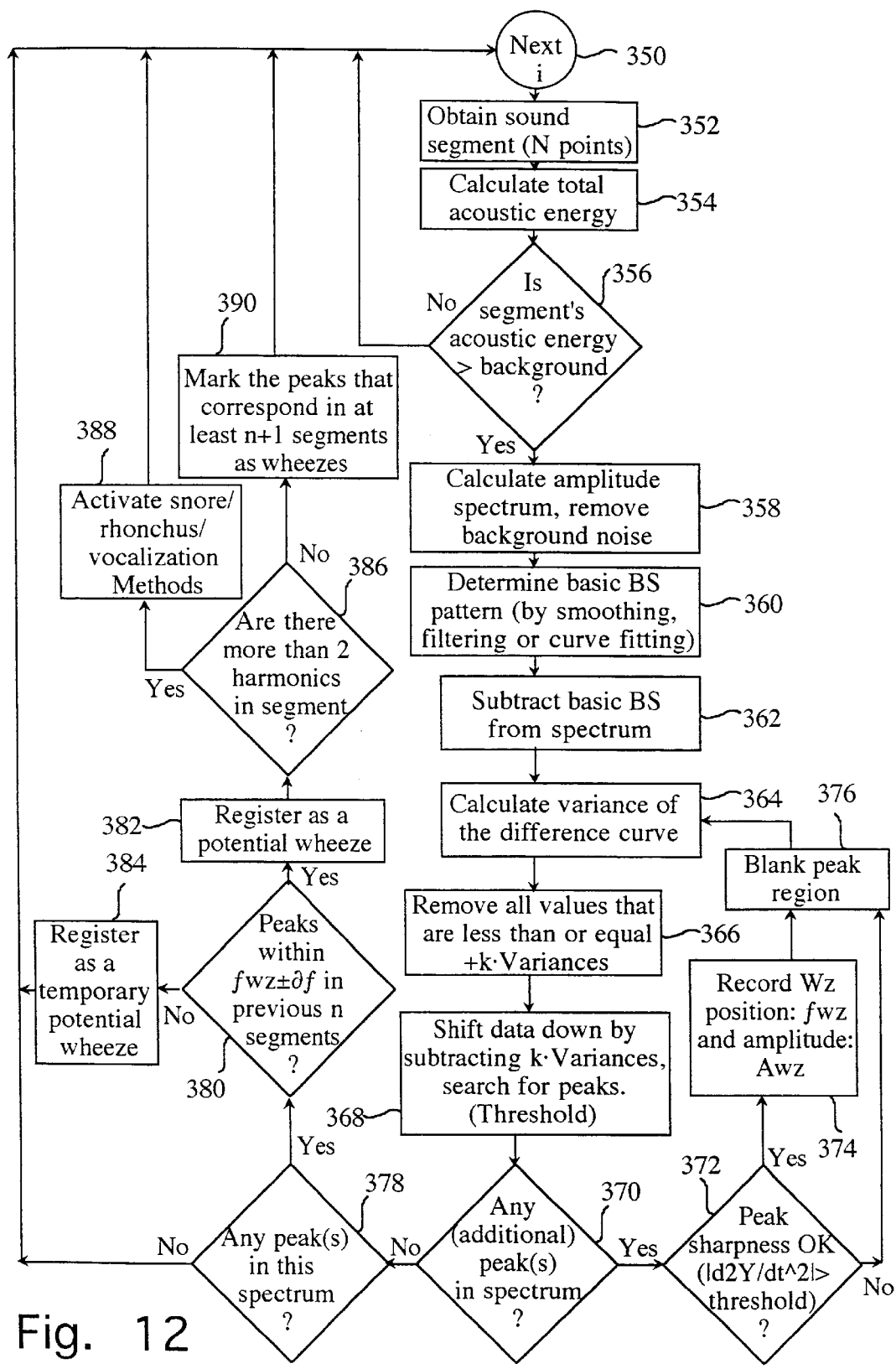
FIG. 12 is a flow chart illustrating in detail the steps of the wheeze detection method in accordance with a preferred embodiment of the present invention.

Reference is now made to FIG. 12 which illustrates the wheeze detection method in accordance with a preferred embodiment of the present invention.

Wheezes may be multiple ("polyphonic") or single ("mono-wheeze"), constant frequency or with varying frequency and may be localized or widely distributed over the chest. The time-domain characteristics of a single wheeze are usually similar to a pure sinusoidal wave. It may, however, contain a harmonic. The frequency domain (Amplitude spectrum) pattern of wheezes is therefore characterized by a single or multiple sharp and narrow peaks.

The wheeze detection method receives as input a sound segment (N data points) digitized from the amplified and conditioned signal of a tracheal or a chest BS sensor as described hereinabove (step 352). The system calculates the total acoustic energy within the segment (step 354) and evaluates the segment's acoustic energy (step 356). If the segment's total acoustic energy is less than or equal to the most recent value of the background's acoustic energy, the segment is identified as "below level" and the system returns control to step 350 for sampling the next segment. This "low-level" designation may be due to breath hold, "silent lung" (a condition with extreme bronchoconstriction where no breath sounds or even wheezes are heard), or due to equipment failure. The system uses the breath detection method of FIG. 9 to deal with these situations as described and illustrat ed hereinabove. If the segment's total acoustic energy is larger than the background, the system calculates the amplitude spectrum of the segment and subtracts the background noise amplitude spectrum from it (step 358).

The system then calculates the amplitude spectrum of the underlying basic breath sound pattern by curve fitting, as described hereinabove, low pass filtration of the spectrum, for example by a Hamming or a 10% FIR filter, or by smoothing (step 360), and subtracts it from the segment's amplitude spectrum (step 362). The system proceeds to look for narrow peaks in the current segment. The system calculates the variance of the array of differences (the residuals) (step 364). Significant peaks are always positive, so that, based on statistical considerations, when no peaks are present, the residuals are randomly distributed around zero and there will be no values that are greater than 4 variances within a segment or greater than 5 variances within an ensemble of segments.

The system then equates all the amplitudes within the segment whose values are less than k·(variance) to k·(variance) (step 366) and subtracts k·(variance) from all the amplitude values within the segment (step 368). An exemplary value that can be used for this procedure is k=5. Thus, the only peaks remaining in the segment have positive values whereas the values in between them are zeroed. The system then searches the spectrum for peaks by comparing the spectrum data to a threshold which has the value of m·(variance), for example, m=0.5. The system identifies a spectrum amplitude value in excess of m·(variance) as a peak (step 370).

It is noted that, as an alternative for comparing the spectrum's data to a threshold in step 370, the system can calculate the 4th moment of the residual array. If the 4th moment of the residual array is significantly greater than 3, for example if the 4th moment is 6, the system searches for peaks. If a peak is detected, its sharpness is evaluated using the absolute value of the first or second derivative of the residuals as an evaluation criterion (step 372). If the absolute value of the first or second derivative of the residuals is larger than a predetermined threshold value, the system registers the peak's frequency $f_{wz}$ and its spectral amplitude $A_{wz}$ (step 374) and blanks the peak region by equating to zero a range within the residual array that is centered at $f_{wz}$ and spans ±Δf around $f_{wz}$ (step 376), for example, Δf=32 Hz.

Δf is determined by N which is the number of data points in the segment and by the sampling rate of the analog to digital converter. If the absolute value of the first or second derivative of the residuals is not larger than a predetermined threshold value, the system blanks the peak region (step 376). The system then continues to search for additional (secondary) peaks within the spectrum by repeating the peak searching steps 364–376 until no more significant peaks are found.

Figure 13A:
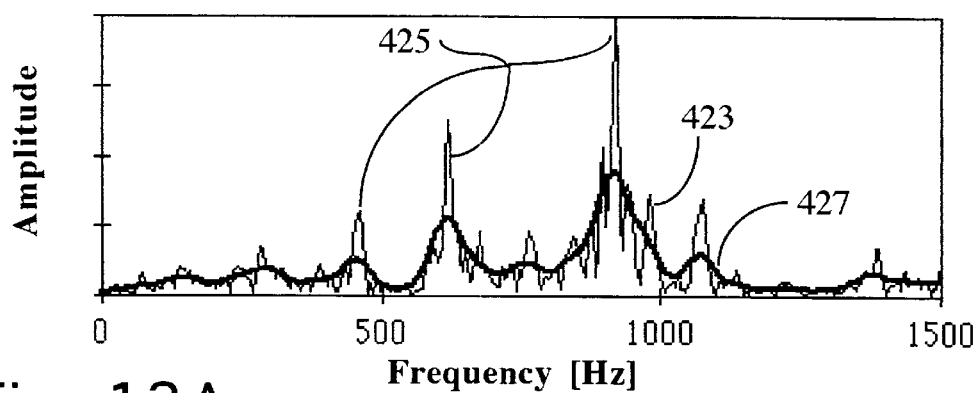
FIGS. 13A and 13B are exemplary graphs illustrating the amplitude spectra calculated by different steps of the wheeze detection method of FIG. 12 in accordance with a preferred embodiment of the present invention.
Figure 13B:
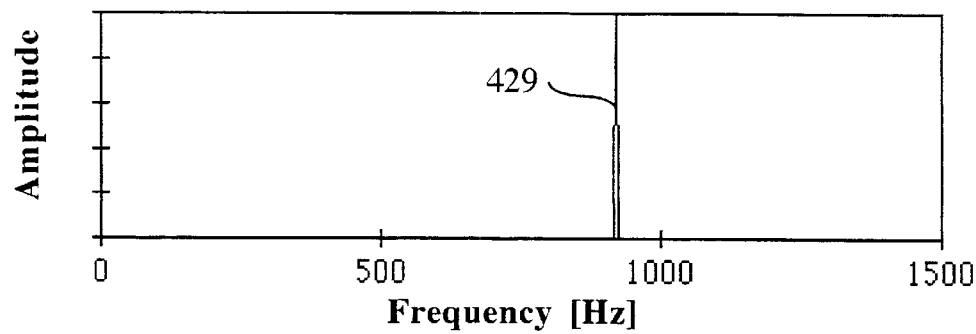

Reference is now made to FIGS. 13A and 13B which illustrate a graphic representation of the amplitude spectra calculated by different steps of the wheeze detection method. In FIGS. 13A and 13B the vertical axis represents the amplitude and the horizontal axis represents the frequency. FIG. 13A illustrates two superimposed curves. The first curve, labeled 423, represents the amplitude spectrum curve of the breath sound segment calculated by step 358 of FIG. 12. The second curve, labeled 423, represents the amplitude spectrum of the basic BS pattern calculated by step 360 of FIG. 12. The three largest peaks of curve 423 are labeled 425. FIG. 13B illustrates the output of step 376 of the wheeze detection method of FIG. 12 after the first pass through steps 364–376. The largest spectral peak which was detected is labeled 429. It is noted that the range around and including the first detected peak 429 is blanked on subsequent passes so that the secondary peaks may be detected (not shown).

Returning to FIG. 12, if no more peaks are found in the segment, the system transfers control to step 378. Step 378 is based upon experimental observations of the duration of actual wheezes and of their trends within a breath. The method evaluates each peak to assure that it is part of a group of peaks that appear at approximately the same frequency in preceding or subsequent segment's amplitude spectra. A peak is accepted as a wheeze only if it appears consecutively in three or more segments that span at least 150 ms but no more than 2500 ms (2.5 seconds). Thus, the system checks if there was any peak in the current segment's spectrum (step 378). If there is no peak in the current segment's spectrum, the system transfers control to step 350 for obtaining the next segment. If any peaks were detected in the current segment's spectrum, the method checks the record of the previous n segments for the presence of significant peaks at $f_{wz}±Δf^*$ (step 380), where Δf* may be set as a fraction of the Nyquist frequency (half the sampling rate) or as a constant, for example, Δf*=64 Hz. An exemplary value of n is n=2 where the total number of segments checked including the current segment is 3. Thus, for an exemplary segment duration of 50 ms, the total duration checked by the system for the presence of significant peaks is 150 ms.

If corresponding peaks appear in previous segments, the peak is registered as potential wheeze (step 382). If no matching peaks are found in the previous segments the registration is temporary (step 384), pending the findings in the next segments.

The final part of the method's wheeze verification procedure is the separation of true wheezes from other signals that generate sharp prominent peaks in the amplitude spectrum. The latter include speech (vocalization), snoring, and rhonchi. All three signals are periodic but non-sinusoidal in the time domain, displaying repetitive, relatively complex, sound structures. These signals are represented by a series of sharp peaks that are uniformly spaced in the amplitude spectrum. These peaks are distinguished from the peaks of true wheezes by the number of harmonics which is the number of peaks that are spaced exactly $\Delta f$ Hz apart While speech, snores and rhonchi always have more than three such peaks, wheezes usually have one peak with an occasional single harmonic that is substantially attenuated. The separation of non-wheeze "peaked" signals into the subgroups of rhonchi, snores, and speech is disclosed in detail hereinafter. Thus, after the system registered a potential wheeze (step 382), the system checks whether there are more than two harmonics in the segment (step 386). If there are more than two harmonics in the segment, the segment is not designated as belonging to a potential wheeze, the system activates the rhonchi/snore/vocalization detecting methods (step 388) and returns control to step 350 for obtaining the next segment. If there are not more than two harmonics in the segment, the segment is designated as belonging to a wheeze and the system registers the peaks that correspond in at least n+1 segments as wheezes (step 390), where $(n+1) \cdot (segment\ duration) \geq 150$ ms, and transfers control to step 350 for obtaining the next segment.

It is noted that since the rate of sound structures in rhonchi and snores is low, being in the approximate range of 40–120 sound structures per second, it is important to evaluate segments of larger duration than those used for detection of wheezes and other higher frequency sounds. An exemplary suitable segment duration is equal to or larger than 200 ms.

Once the evaluation and verification of a segment is completed, the system moves on to analyze the next sound segment. It is noted that, in accordance with a preferred embodiment of the present invention, the analysis of a segment is completed before the end of the acquisition of the data of the next consecutive segment, so that quasi real-time monitoring is accomplished. This feature, in particular, enables the continuous on-line monitoring of the results of the breath analysis performed by the preferred embodiments of the present invention.

The Rhonchi Detection Method

Rhonchi are continuous adventitious breath sounds that are heard over the chest and the trachea of patients with a variety of lung diseases. The sounds are different from wheezes in their lack of smooth musical tone which is replaced by a rough, grinding-like quality. Rhonchi may be inspiratory or expiratory. In the time domain, rhonchi consist of non-sinusoidal, periodic waves (repetitive sound structures) and in the frequency domain by multiple peaks of power.

Figure 14:
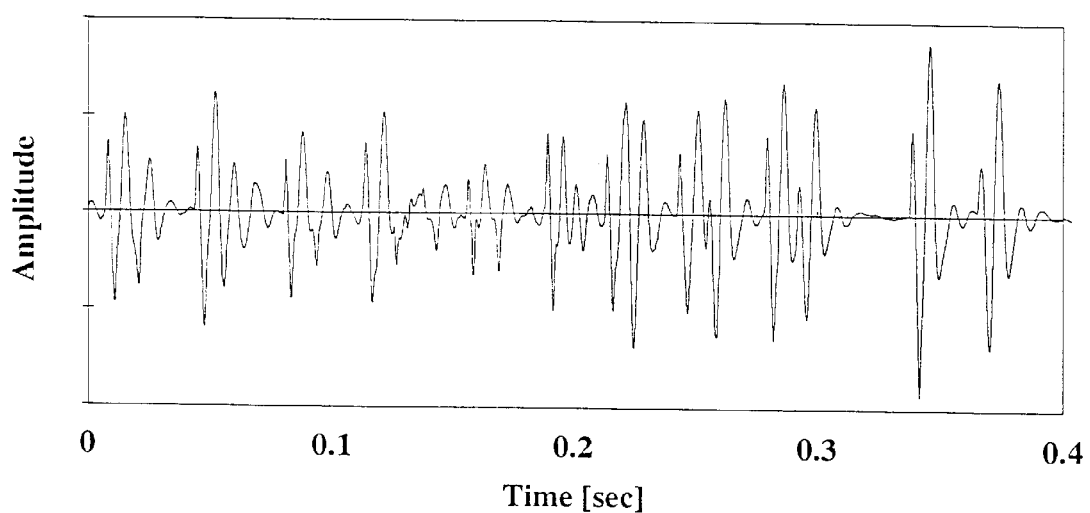
FIG. 14 is an exemplary graph illustrating part of a rhonchus sampled in a patient with pneumonia and lung cancer.

Reference is now made to FIG. 14 illustrating a graph of a section from a rhonchus (sampled in a patient with pneumonia and lung cancer). The graph's vertical axis represents amplitude and the horizontal axis represents time. It is noted that the amplitude trace contains a train of multiple repetitive sound structures.

These features are also characteristic of snores and vocalization (speech), so that rhonchi cannot be distinguished and identified solely based on these features. However, unlike both snores and vocalization, rhonchi are only detectable by contact sensors placed over the chest wall and cannot be picked up by an ambient microphone. In addition, rhonchi are often localized sounds picked up over a certain chest region, but not over other locations. Thus, a particular feature of the method of detection of rhonchi of the present the invention, is that the positive identification of rhonchi utilizes the signals picked up by the ambient noise microphone, in addition to the signals picked up by the chest-wall BS sensor.

Reference is now made to FIG. 15 which is a flow chart illustrating the steps of the rhonchi detection method in accordance with a preferred embodiment of the present invention.

The rhonchi detection method is designed to identify the presence of rhonchi in breath sounds. The method uses specific characteristics of the sounds to distinguish them from wheezes on the one hand and from snores and vocalization sounds on the other. When rhonchi are detected, the system performs specific actions which may include the activation of an alarm (in the PPG monitor embodiment), the recording of the rhonchi parameters (in the PPG recorder embodiment) or the generation of graphic and parametric information to be printed or displayed (in the PPG meter or monitor embodiments).

The rhonchi detection method is a second-line method. It is invoked only if called by the primary method—the wheeze detection method. The rhonchi detection method is activated by the wheeze detection method if three or more equally-spaced peaks are detected in the amplitude spectrum or by the crackle detection method if closely and equally spaced multiple crackles are detected. The system verifies that the presence of a train of sound structures actually represents a rhonchus by receiving the ambient noise data segment $A_i$ and the breath sound data segment $T_b$ of the tracheal BS sensor or a chest BS sensor (step 400) and calculating the transfer function between the breath sound data segment B and the sounds data segment $A_i$ picked up simultaneously by the ambient noise microphone (step 404). The system then calculates the coherence of the transfer function (step 406). The system compares the frequency ranges of peaks in the coherence data with the frequency ranges of peaks in the amplitude spectrum of Si (step 408). If the frequency ranges of high coherence, for example the frequency ranges for which the coherence>0.7, match within a 32 Hz range to the frequency ranges of the peaks in the amplitude spectrum of the chest wall sounds, the system rejects the hypothesis that these peaks represent rhonchi and transfers control to the snore and vocalization methods (step 410). This verification procedure becomes optional if the ambient sound level is low and less than a threshold value as shown and described for step 136 of FIG. 9.

Alternatively, the system performs a cross correlation between the chest wall sound data and the ambient noise data and searches for peaks at intervals that correspond to the reciprocal of the frequency interval between the peaks in the spectrum. When such correlation is found, the system rejects the hypothesis that the sounds represent rhonchi and transfers control to the snore/vocalization detection methods (step 410). If there is no correspondence between the frequency ranges of the coherence peaks and the amplitude spectrum peaks, the system identifies the segment as containing rhonchi and records the parameters of the rhonchus (step 412). The parameters recorded are the rhonchus duration and the relative positioning of the rhonchus within the respiratory cycle (expiratory or inspiratory rhonchus). It is noted that, at step 412, the system uses the breath phase and flow data calculated by the breath detection method of FIG. 9.

It is noted that if rhonchi are detected and verified, the system activates a "rhonchi alarm" in the Monitor configuration (step 414), otherwise, the system records or presents the rhonchi parameters (step 412).

The Snore Detection Method

Snores are continuous adventitious breath sounds that are generated during sleep due to oscillations of certain upper airway structures. These are loud sounds that are detectable by an ambient noise microphone as well as over the chest by a contact sensor.

Figure 16A:
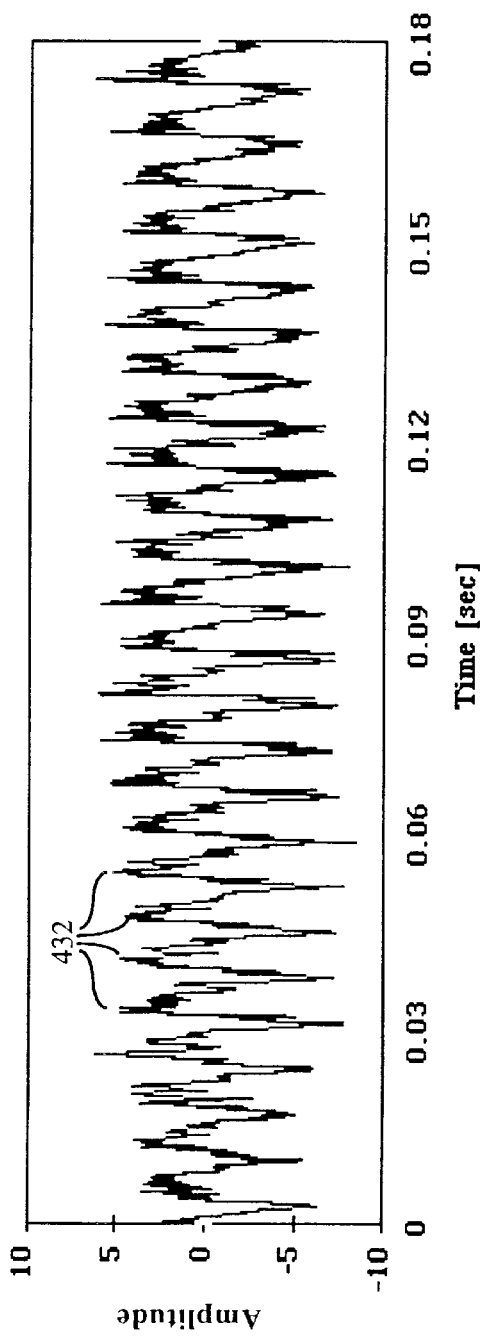
FIGS. 16A and 16B are exemplary graphs illustrating the curves of a "simple" snore in the time and frequency domains, respectively.
Figure 16B:
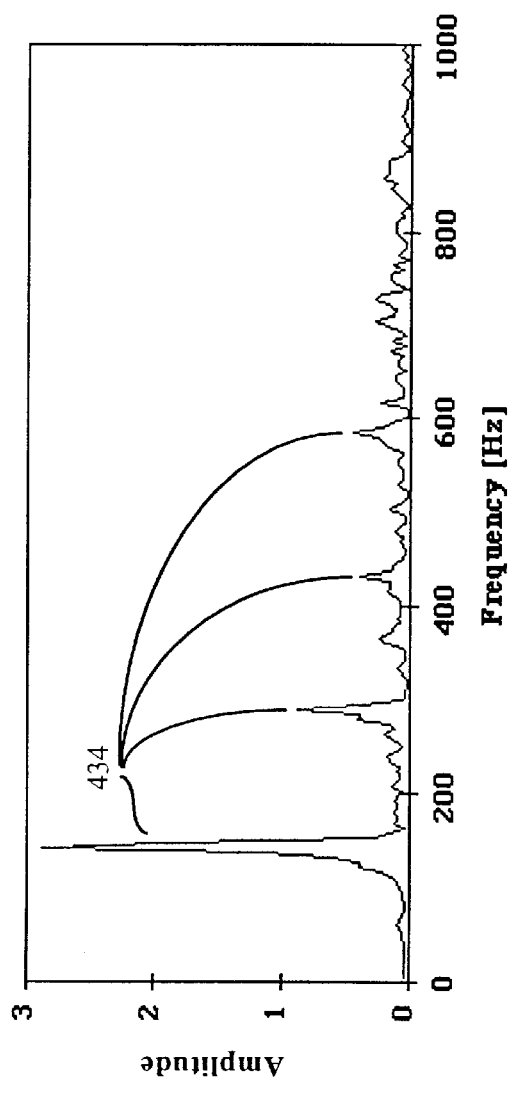
Figure 17A:
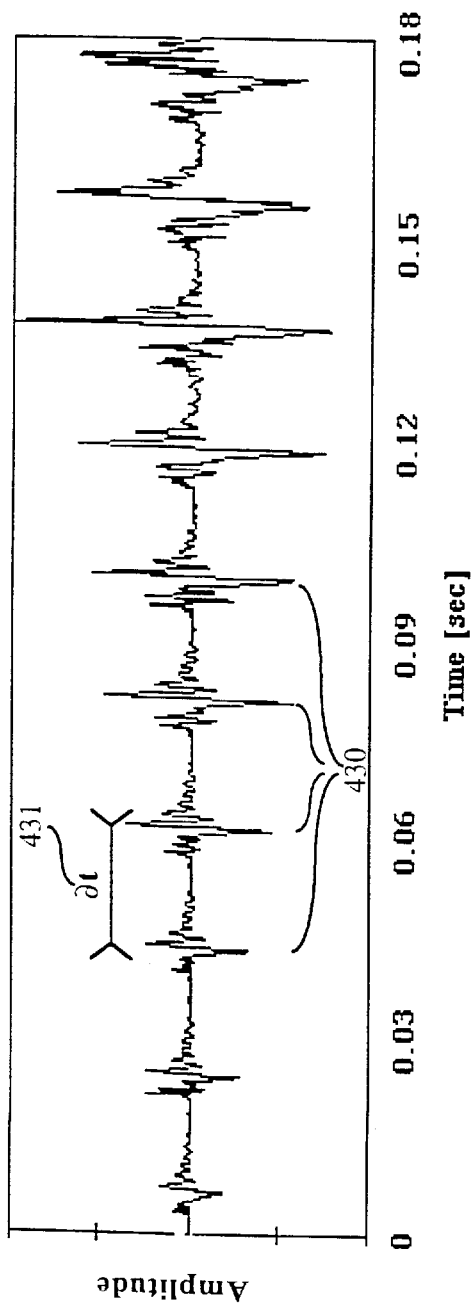
FIGS. 17A and 17B are exemplary graphs illustrating the curves of a "complex" snore in the time and frequency domains, respectively.
Figure 17B:
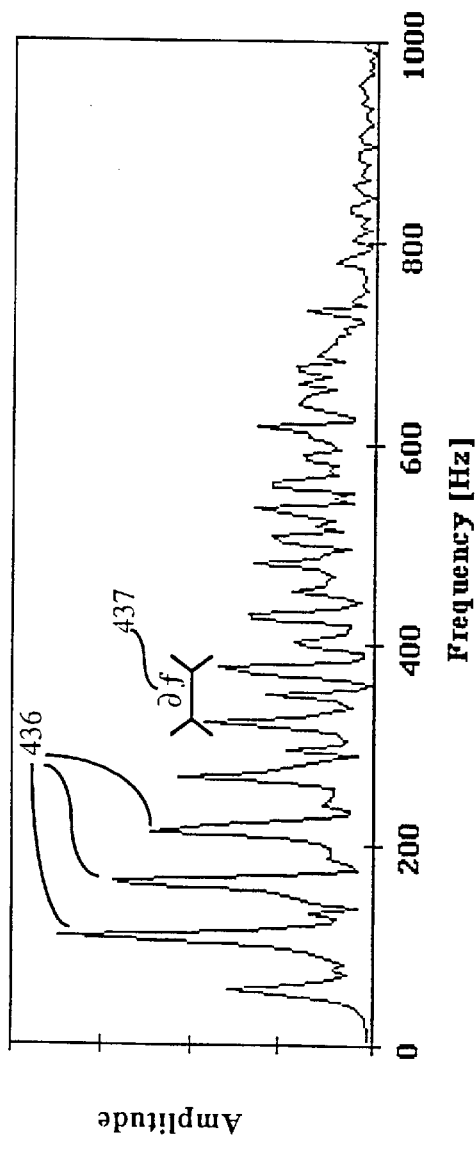

Reference is now made to FIGS. 16A and 16B, illustrating the curves of a "simple" snore in the time and frequency domains, respectively, and to FIGS. 17A and 17B, illustrating the curves of a "complex" snore in the time and frequency domains, respectively.

In the time domain, snores are characterized as a periodic wave consisting of simple or complex sound structures. FIG. 16A and 17A are graphs illustrating the time domain curves of a simple snore and a complex snore, respectively, where the vertical axis represents the snore amplitude and the horizontal axis represents time. Some of the simple sound structures occurring repetitively in FIG. 16A are labeled 432 while some of the repetitively occurring complex sound structures of FIG. 17A are labelled 430. The periodic sound structures of simple and complex snores have a period at, labelled 431, in FIG. 17A.

The snores may be superimposed on random noise, such as generated by the tracheal BS sensor, with varying relationships between the snore sound structures and the noise.

In the frequency domain, snores are represented by a series of equally spaced sharp and narrow peaks. The frequency interval between the peaks is equal to the reciprocal of the time interval between the sound structures in the time domain.

FIGS. 16B and 17B are graphs illustrating the frequency domain (power spectrum) curves of the simple snore of FIG. 16A and the complex snore of FIG. 17A, respectively, where the vertical axis represents the amplitude and the horizontal axis represents the frequency. FIG. 16B illustrates the four largest peaks, labeled 434, of the power spectrum of the simple snore. FIG. 17B illustrates the three largest of the multiple peaks, labeled 436, of the power spectrum of the complex snore. The highest peak is not always the first in the series as seen in FIG. 17B. The number of the peaks and their distribution is determined by the frequency content of each individual sound structure. The frequency interval $\partial f$ between adjacent peaks in the power spectrum is labelled 437 in FIG. 17B.

The snore detecting method is designed to identify the presence of snores during monitoring of breath sounds and to distinguish snores from other adventitious or environmental sounds. The method is used by the PPG Monitor and the PPG Recorder, but may also be used as a stand-alone snore detection device, or as part of a sleep disorders evaluation system. The output of the method includes the timing, duration, rate of sound structures per unit time, and the character of the snore (for example simple or complex).

The snore detection method is a second-line method. It is invoked only if called by a primary method such as the wheeze detection method, the crackle detection method, the rhonchus detection method or the breath detector method.

Figure 18:
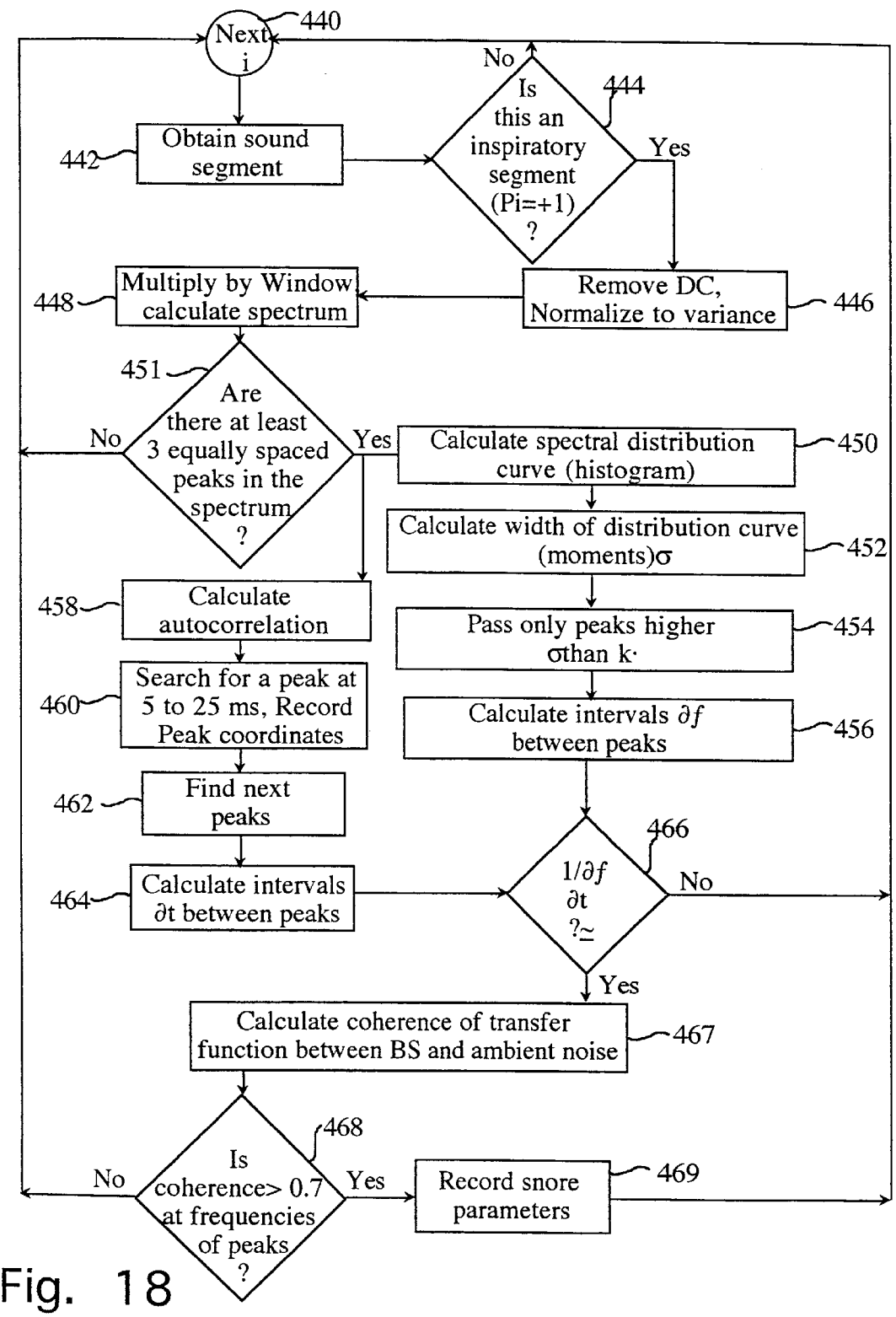
FIG. 18 is a flow chart illustrating the steps of a snore detection method in accordance with a preferred embodiment of the present invention.

Reference is now made to FIG. 18 which is a flow chart illustrating the steps of the snore detection method in detail. In accordance with a preferred embodiment of the present invention, the snore detection method is based on detection of segments in which uniformly spaced and similar sound structures are present.

It is noted that the method is limited to detection of inspiratory snores since expiratory snores cannot be effectively distinguished from vocalization.

The system obtains a sound segment of duration T (step 442). It is noted that, in order to function properly, the sound segment duration T should be approximately 200±50 ms. These limits are set in order to facilitate capture of a sufficient number of sound structures even in complex snores with a relatively low rate of sound structure generation and in order to limit the duration so that a train of equally spaced structures may be isolated. The system determines whether the segment is an inspiratory segment (step 444) by checking the parameter Pi which was calculated by block 3 of FIG. 9. If the segment is not an inspiratory segment, the system returns control to step 440 for obtaining the next segment.

If the segment is an inspiratory segment, the system removes the DC component of the segment and normalizes the segment's data by its variance (step 446), multiplies the normalized segment by a window, for example a Blackman window, and calculates the power spectrum of the normalized window multiplied segment (step 448). The system then checks the calculated power spectrum for the presence of equally spaced peaks (step 451). If the power spectrum does not contain at least three approximately equally spaced peaks, the system rejects the possibility that the current segment is a snore and returns control to step 440 to obtain the next segment. If the power spectrum contains at least three approximately equally spaced peaks, the system calculates the autocorrelation of the normalized, window multiplied signal (step 458).

The system can calculate the autocorrelation using values of time delay of 5 to 25 ms, or by calculating the inverse transform of the non-truncated power spectrum. The system checks for peaks in the calculated autocorrelation (step 460). If a significant peak is found within 5 to 25 ms from the beginning of the segment, the system searches for one or more subsequent equally spaced peaks (step 462) and calculates the time interval between them as $\partial t$ (step 464). In parallel to the checking of the autocorrelation for peaks (steps 458–464), the system evaluates the power spectrum calculated in step 448 in search of a train of sharp peaks. The system calculates the distribution curve (histogram) of the spectrum (step 450). The system calculates the width a of the distribution curve (step 452) from the zeroth, first and second moments $\mu_0$, $\mu_1$, & $\mu_2$, respectively, of the distribution curve, using equations 5 and 6.

$$\sigma = \sqrt{\frac{\mu_2}{\mu_o} - \left(\frac{\mu_1}{\mu_0}\right)^2} \tag{5}$$

$$\mu_0 = \frac{1}{n}\sum_{i=1}^{n} x_i; \mu_1 = \frac{1}{n}\sum_{i=1}^{n} i \cdot x_i; \mu_2 = \frac{1}{n}\sum_{i=1}^{n} i^2 \cdot x_i \tag{6}$$

where n is the number of elements in the distribution and $x_i$ are the values of the elements. The system accepts as peaks only peaks that are greater than k·σ where k is a constant, for example k=4 (step 454). The system then calculates the frequency intervals between the accepted peaks $\partial f$ (step 456). The system verifies the calculated intervals between the peaks by comparing between ∂t and (∂f)$^{-1}$ (step 466). If the values of ∂t and (∂f)$^{-1}$ are not within close proximity, the system does not identify the segment as a snore and returns control to step 440 to obtain the next segment.

If the two values ∂t and (∂f)$^{-1}$ are within close proximity, for example when |∂t−(∂f)$^{-1}$|<1 ms, the system calculates the coherence of the transfer function between the current BS segment and the current ambient noise segment (step 467). The system then checks the coherence value at the frequencies of the peaks (step 468). If the coherence at the frequencies of the peaks is not greater than 0.7, the system rejects the possibility that the current segment is a snore and returns control to step 440 to obtain the next segment. If the coherence at the frequencies of the peaks is greater than 0.7, the system accepts the segment as containing a snore, logs the snore parameters (step 469) and returns control to step 440 for obtaining the next segment. The logged snore parameters are the amplitude and duration of the snore, the snore type (complex or simple) and the respiratory phase. The system distinguishes between a complex and simple snore by using a peak count criterion. If the system detects 3–4 peaks in the power spectrum, the system registers the snore as a simple snore. If the number of peaks detected by the system is equal to or greater than 5, the system registers the snore as a complex snore.

The Cough Detection Method

The cough detection method disclosed hereinbelow as part of the PPG system of FIG. 2 is designed to detect cough sounds in patients and to determine their timing, number and parameters. The cough detection method can be used as part of the PPG Monitor of FIG. 4, the PPG Recorder of FIG. 5 and the PPG Meter of FIG. 3. The cough detection method can also be used as a part of a stand-alone device. The detection and count of coughs is important in the follow-up of asthma and other lung diseases and their treatment.

Figure 19A:
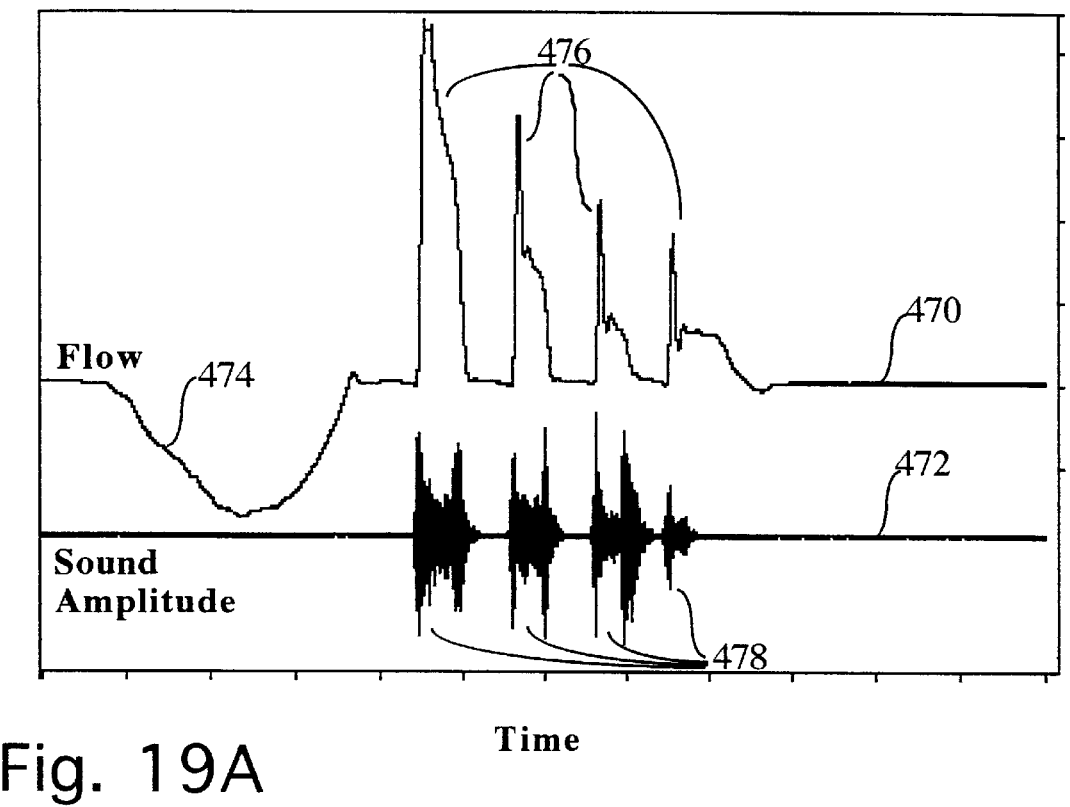
FIGS. 19A and 19B are exemplary graphs illustrating the temporal structure of the sound and air flow data of a recorded cough.
Figure 19B:
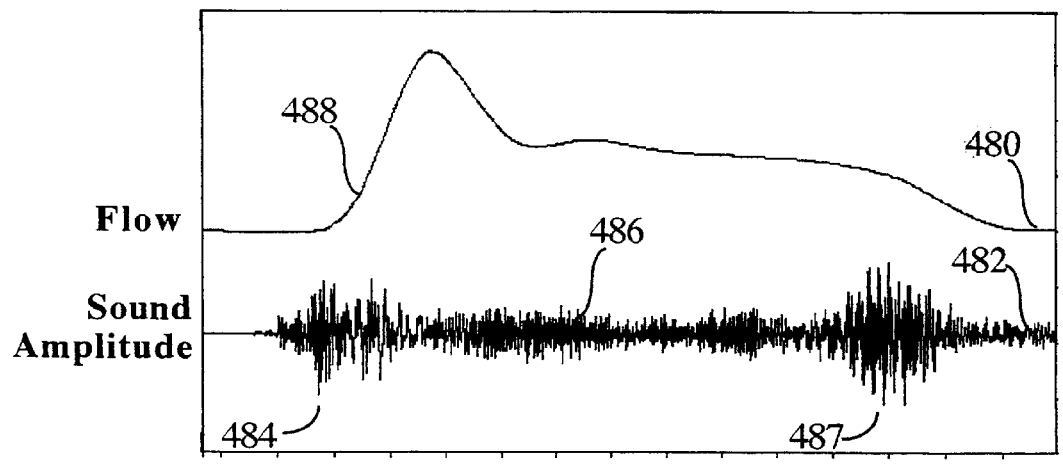

Reference is now made to FIGS. 19A and 19B illustrating the temporal structure of the sound and air flow data of a cough. A cough is an explosive exhalation associated with noise generated from the thorax and upper airways. It is usually preceded by an inspiration and has 1–4 sound components. Each component is accompanied by a rapid motion and change in chest volume. FIG. 19A is a graph illustrating the flow curve 470 recorded by a pneumotachograph and the sound curve 472 recorded by an ambient noise microphone. The horizontal axis represents time, the left vertical axis represents the sound amplitude of curve 472 and the right vertical axis represents the flow of curve 470. In the flow curve 470, an inspiration 474 precedes the cough which is composed of four components, labelled 476, and has an abrupt onset. In the sound curve 472, the cough includes four sound components 478, each having an initial and final louder parts and a less loud middle part. FIG. 19B illustrates a graph of a single component of a cough. The axes are similar to the axes of FIG. 19A except that the time axis is expanded relative to the time axis of FIG. 19A. The flow curve 480 illustrates the abrupt onset, labelled 488, of the cough component while the sound curve 482 illustrates the initial louder part, labelled 484, the final louder part, labelled 487, and the less loud middle part, labelled 486. Thus, the envelope of a cough sound can be said to have a characteristic "double hump" shape.

The cough detection method uses information from an ambient noise microphone and from one or more contact sensors placed on the subject's body. The system also uses data from a chest expansion sensor or flow detecting sensor, for example an impedance measurement, to verify that the signal actually represent a is cough. The ambient noise microphone is placed near the subject. If the noise detection method detects a loud environmental sound, it activates the cough detection method. The cough detection method positively identifies coughs and records their timing, duration, and number of components.

Figure 20:
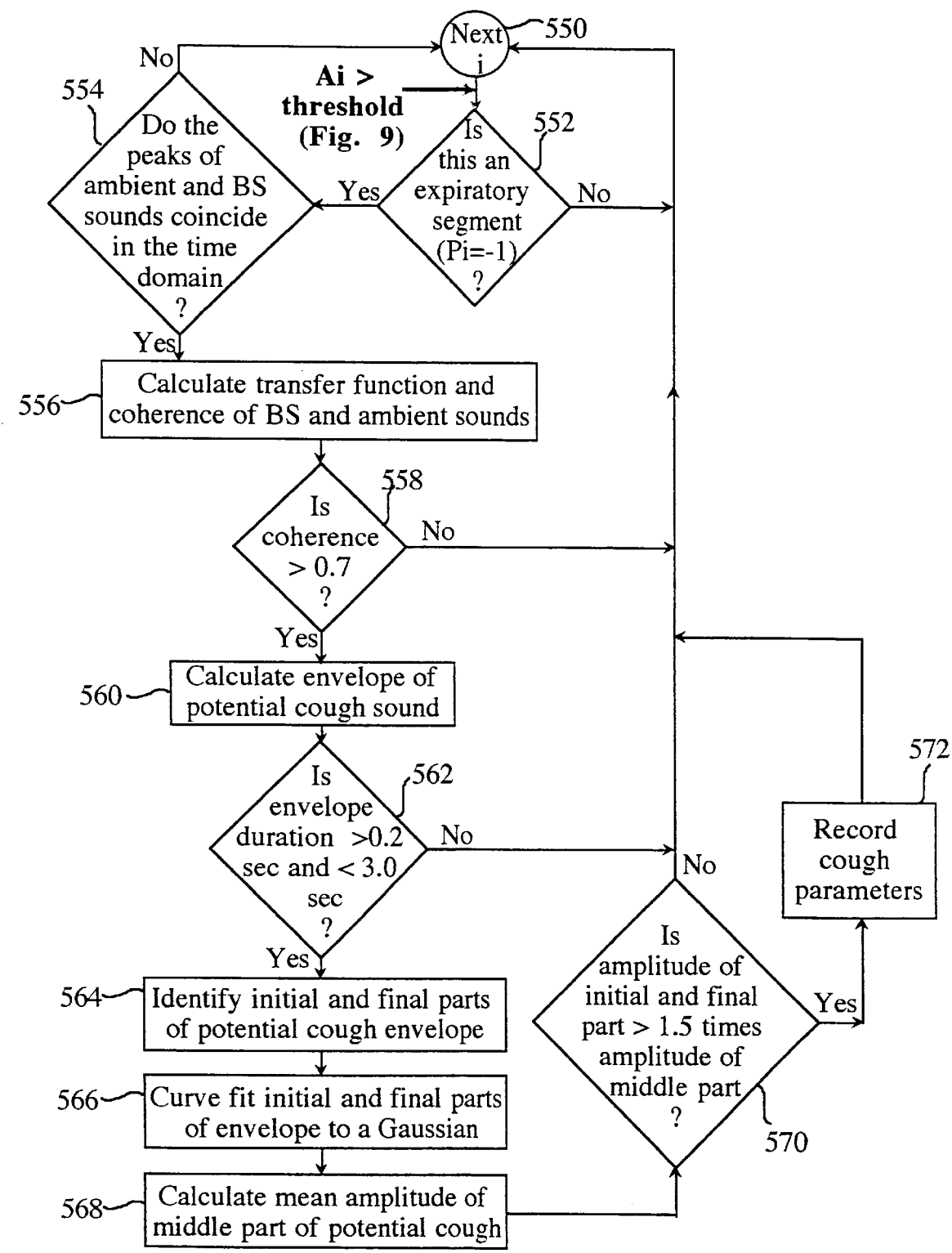
FIG. 20 is a flow chart illustrating the steps of a cough detection method in accordance with a preferred embodiment of the present invention.

Reference is now made to FIG. 20 which is a flow chart illustrating the flow control and the various steps of the cough detection method in detail.

When the cough detection method is activated by one of the primary methods, for example when the $A_i$ parameter of the step 136 of FIG. 9 is larger than threshold as described hereinabove, the system checks whether the current segment is an expiratory segment by checking the value of the parameter $P_i$ (step 552). If $P_i$ is not equal to −1, the system returns control to step 550 for obtaining the next segment. If $P_i$=−1, the system checks whether the peaks of the ambient sound and the breath sound coincide in the time domain (step 554). If the peaks of the ambient sounds and the breath sounds do not coincide within 50 ms in the time domain, the system transfers control to step 550 for obtaining the next segment. If the peaks of the ambient sounds and the breath sounds coincide within 50 ms in the time domain, the system calculates the transfer function and coherence of the breath sounds and the ambient sounds (step 556). The system then checks the coherence value of the transfer function (step 558). If the coherence is not larger than 0.7, the system transfers control to step 550 for obtaining the next segment. If the coherence is greater than 0.7, the system calculates the envelope of the potential cough sound (step 560). The system then checks the duration of the potential cough sound envelope (step 562). If the duration of the potential cough sound envelope is not greater than 0.2 seconds and not smaller than 3.0 seconds, the system transfers control to step 550 for obtaining the next segment. If the duration of the potential cough sound envelope is greater than 0.2 seconds and smaller than 3.0 seconds, the system identifies the initial and final parts of the potential cough envelope (step 564), curve fits the initial and final parts of the potential cough envelope to a gaussian (step 566) and calculates the mean amplitude of the middle part of the potential cough envelope (step 568). It is noted that the initial, middle and final parts of the calculated envelope of a cough (not shown) approximately coincide in the time domain with the initial, middle and final parts, respectively, of the cough sounds from which the envelope was calculated. The initial, middle and final parts are best seen in the exemplary cough sound of FIG. 19B and are labelled 484, 486 and 487, respectively. The envelope calculation of step 560 can be performed, for example, by rectifying and suitably filtering the breath sound data.

The system then checks the amplitudes of the initial, middle and final parts of the calculated envelope of the potential cough (step 570). If the amplitude of the initial and the final parts of the envelope are not greater than 1.5 times the middle part the of the envelope of the potential cough sound, the system transfers control to step 550 to obtain the next segment. If the amplitude of the initial and the final parts of the envelope are greater than 1.5 times the middle part the of the envelope of the potential cough sound, the system registers the segment as a cough segment, records the cough parameters (step 572) and transfers control to step 550 to obtain the next segment. It is noted that the recorded cough parameters are the cough duration and amplitude.

The Crackle Detection Method

Figure 21:
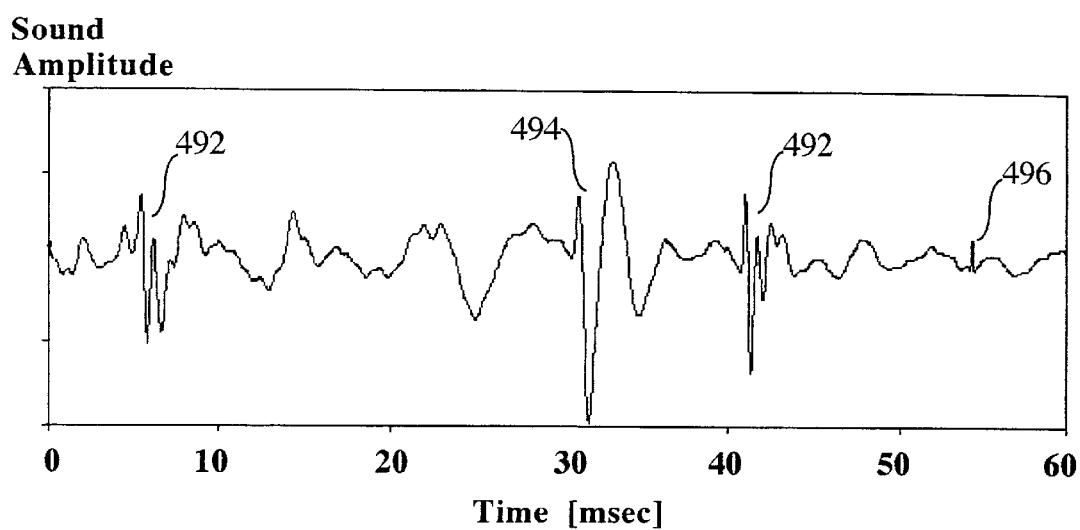
FIG. 21 is an exemplary graph illustrating fine and coarse crackles recorded from a patient with pulmonary fibrosis.

Crackles are discontinuous adventitious breath sounds with an abrupt onset and a short duration. They are heard over the chest wall of patients with cardiopulmonary diseases. The presence of crackles usually represents an abnormality. Reference is now made to FIG. 21 illustrating examples of typical crackles recorded from a patient with pulmonary fibrosis. In FIG. 21 the vertical axis represents the amplitude of the sound and the horizontal axis represents time. The sound curve contains two "fine" crackles labelled 492, one "coarse" crackle labelled 494 and an artifactual sound labelled 496 having an abrupt onset and a very short duration.

The crackle detection method described herein as part of the PPG system is designed to identify the presence of crackles in breath sounds, determine their timing within the respiratory cycle, count their number, and characterize their waveform. The crackle detection method is used by the PPG monitor, the PPG meter and the PPG recorder, and can also be used as a "stand-alone" module or in a "stand-alone" device. The crackle detection method can be used during examination of the chest at shifting body postures to detect gravity-dependent migration of crackles. It can be used in the monitoring of patients during general anesthesia to detect fluid overload from IV fluids or from other sources, for example from irrigation fluid during trans-urethral resection of prostate (TURP) procedure. The crackle detection method can also be used to monitor patients after myocardial infarction in the coronary care unit. Such patients often develop congestive heart failure.

The crackle detection method can also be used to monitor patients at home who complain of orthopnea or paroxysmal nocturnal dyspnoea (PND). The crackle detection method can further be used to monitor accumulation of secretions in the airways of intubated patients in the intensive care unit (ICU).

It is noted that the crackle detection method can be applied for monitoring and analyzing the breath sounds of multiple sensors positioned at different sites of the patient's body simultaneously, or of a single sensor positioned at a single site.

Figure 22:
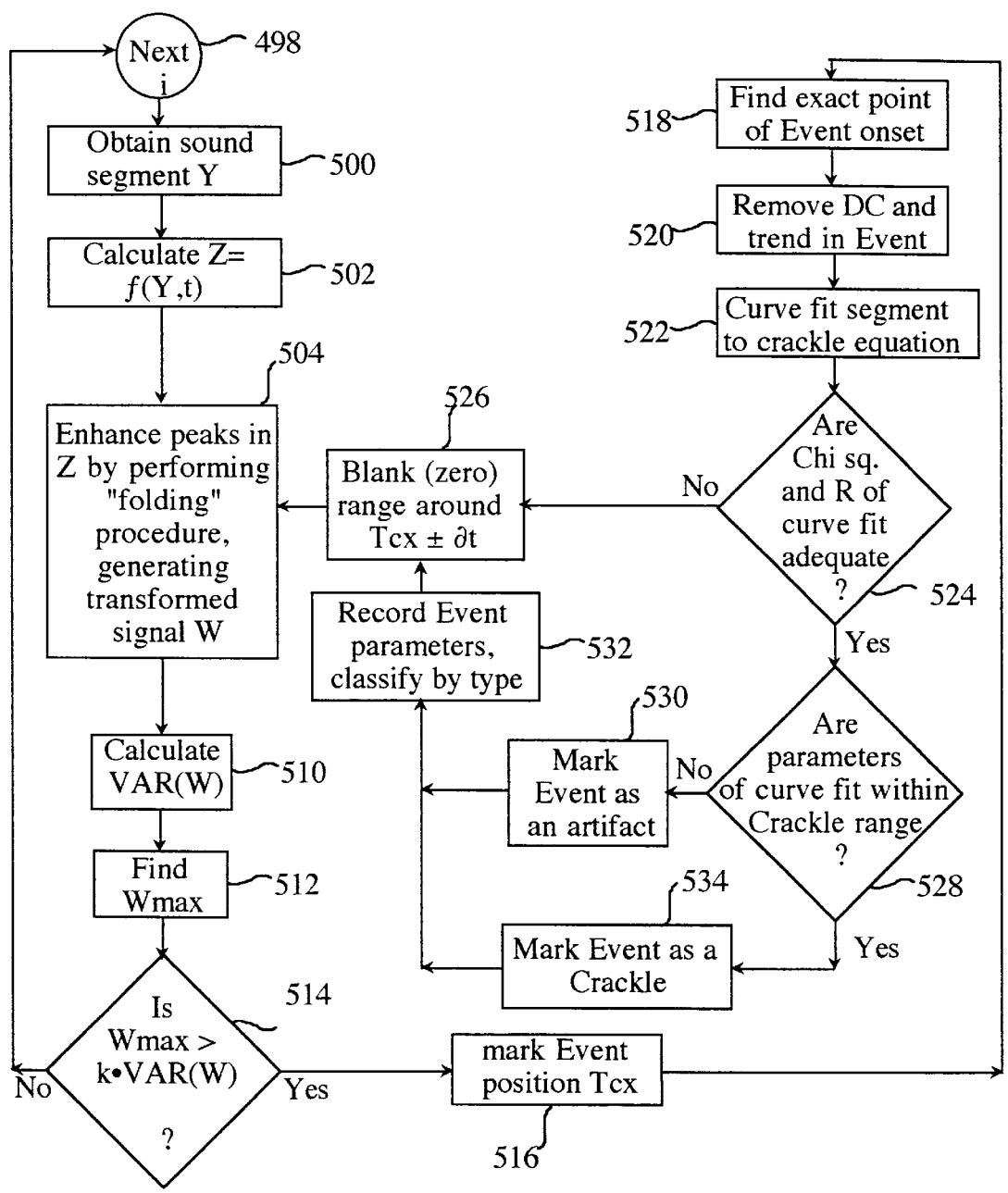
FIG. 22 is a flow chart illustrating the steps of a crackle detection method in accordance with a preferred embodiment of the present invention.

Reference is now made to FIG. 22 which is a schematic block diagram illustrating in detail the steps of the crackle detection method. The input signals for the method are digitized breath sounds from one or more sensors placed over the chest wall. Amplification, filtration and digitization of the analog signals are as described in detail hereinabove. The data is processed on-line or off-line to detect crackles. Selected segments may be archived for documentation or post-processing.

The system obtains a segment Y of N data points, for example N=1000 (step 500). The system first calculates Z which is a measure of an abrupt change in the signal. Z is defined by one of a family of equations 7:

$$Z = \left(\frac{d^m Y}{dt^m}\right)^n \left(\frac{d^k Y}{dt^k}\right)^l \quad (7)$$

where m, n, l, and k are parameters. Each of the parameters m, n, l, and k can have the values 0, 1 and 2.

The discrete form of the family of equations 7 is represented by the family of equations 8:

$$Z_{i+1} = \frac{1}{\Delta t^{(m \cdot n + k \cdot l)}} \cdot (Y_{i+m} - Y_i)^n \cdot (Y_{i+k} - Y_i)^l \quad (8)$$

where $Y_i$ are the data points, $\Delta t$ is the sampling interval, $Z_{i+1}$ are the derived values for the i+1 points in the segment and m, n, l, and k are the parameters of the family of equations 7 described hereinabove.

The decision as to which values of the parameters m, n, l, and k are to be used for calculating $Z_i$ of equation 8 depends on the balance between the desired accuracy, which represents the sensitivity and specificity of detection, and the desired speed of calculation. Preferably, the system calculates $Z_i$ which is the second power of the second derivative of the signal for each point i in the segment (step 502), by using equation 9:

$$Z_i = \frac{1}{\Delta t^4}(Y_{i+1} - Y_{i-1})^2 \quad i = 2 \to N - 1 \quad (9)$$

where m=2, n=2, k=0 and l=0.

The system then calculates $\sigma(Z)$, which is the variance of Z, using equation 10:

$$\sigma(Z) = \frac{1}{N-2} \cdot \left(\left[\sum_{i=2}^{N-1}(Z_i - \bar{Z})^2\right]\right)^{1/2} \quad (10)$$

where $Z^{(bar)}$ is the mean value of Z within the segment (step 504).

The system applies a "folding" procedure to Z (step 504) as follows: $\sigma(Z)$ which is the variance of Z is subtracted from each value of Z. The system calculates a new series of values Z using equation 11:

$$Z^* = |Z - \sigma(Z)| \quad (11)$$

This "folding" procedure is subsequently repeated m times on the resulting series of the previous step, where m varies between 2 to 4, for gradually diminishing the smaller fluctuations near the time axis while enhancing the peaks (if peaks are present in the segment). The final results of the repeated "folding" procedure is referred to hereinafter as W.

Figure 23:
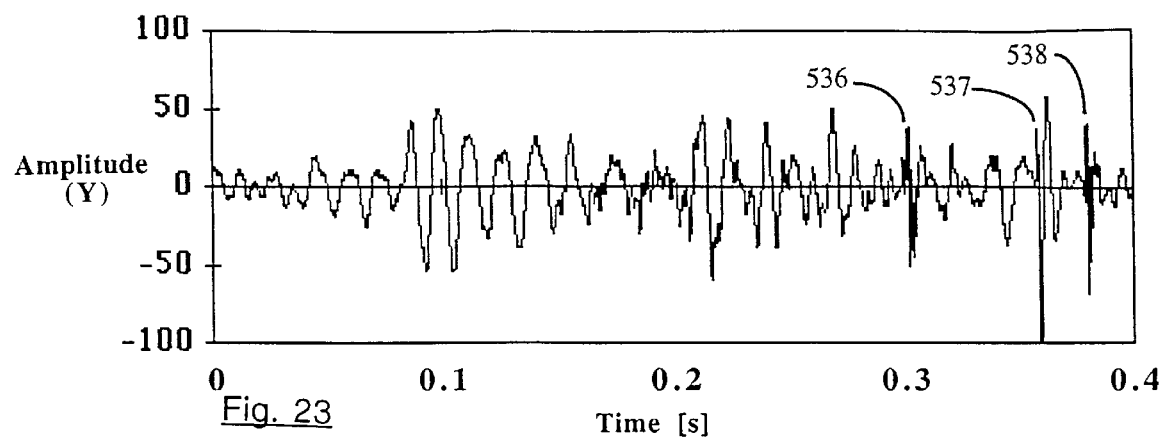
FIG. 23 is a graph illustrating raw data of a breath sounds segment prior to being processed by the crackle detection method of FIG. 22.
Figure 24:
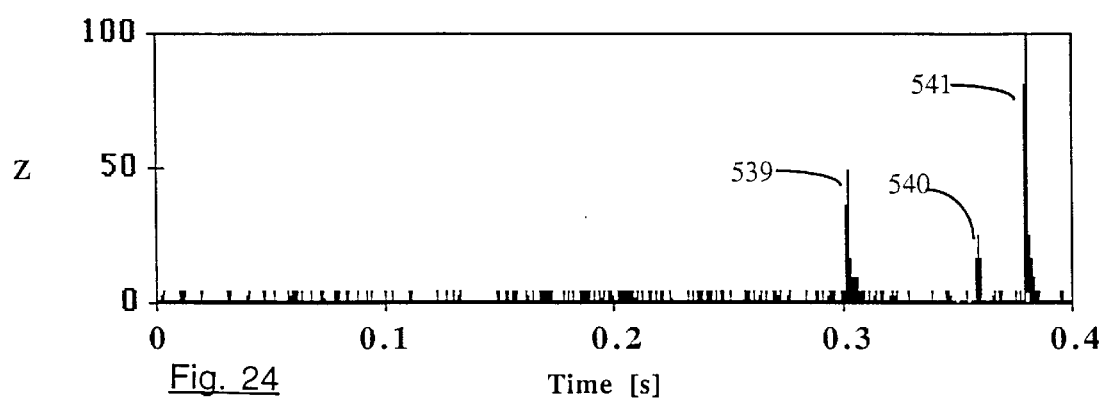
FIG. 24 is a graph illustrating the second power of the second derivative (Z) calculated from the raw data values of FIG. 23 by the crackle detection method of FIG. 22.

Reference is now made to FIGS. 23 and 24 illustrating the processed data resulting from some of the different steps of data processing performed by the crackle detection method of FIG. 22. FIG. 23 illustrates the "raw data" of a segment of breath sounds that is obtained by the system in step 500. The vertical axis represents the amplitude of the digitized sound data and the horizontal axis represents time. The sound data of FIG. 23 contains three crackles labelled 536, 537 and 538. FIG. 24 illustrates a graph of the values of the second power of the second derivative (Z) calculated by step 502 of the crackle detection method. The vertical axis represents Z and the horizontal axis represents time. The data of FIG. 24 includes three peaks, labelled 539, 540 and 541 which correspond to the crackles 536, 537 and 538 of FIG. 23, respectively. It is noted that, although the amplitude of the second crackle 537 in the raw data of FIG. 23 has the highest amplitude, the second, corresponding, peak 540 of FIG. 24, does not have the highest amplitude because the second crackle 537 is a coarse crackle and has a lower frequency content.

Going back to FIG. 22, the system calculates $\sigma(W)$ representing the variance of the folded data (step 510) which is used as a basis for finding peaks. The system then finds the maximal value $W_{max}$ of the segment (step 512). The system checks whether the value of $W_{max}$ is greater than $k \cdot \sigma(W)$ where k is a constant, for example k=3.8 (step 514).

Figure 25:
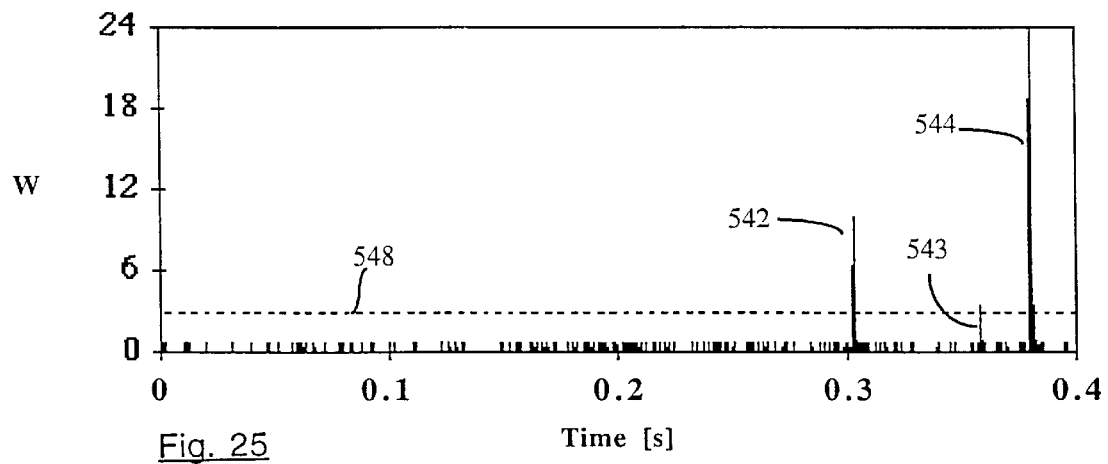
FIG. 25 is a graph illustrating the values W calculated by the crackle detection method of FIG. 22, by "folding" the values Z of FIG. 24.

Reference is now made to FIG. 25 illustrating a graph representing the values W of the folded second power of the second derivative which were calculated by step 508 of FIG. 22 from the Z values of FIG. 24. The vertical axis represents the calculated values of the parameter W and the horizontal axis represents time. The graph includes three peaks, labelled 542, 543 and 544, corresponding to the three crackles 536, 537 and 538, respectively, of FIG. 23. The dashed line 548 represents a threshold of 4-variance used for screening the peaks in step 514 of FIG. 22.

Going back to FIG. 22, if $W_{max}$ exceeds $k \cdot \sigma(W)$, the peak is registered as potentially representing a crackle and the position of the peak $T_{cx}$ is recorded (step 516). The system proceeds through steps 518–528 for evaluating the shape of the "potential" crackle by template matching.

The aim of this part of the method is to distinguish crackles from other signals that have abrupt onset, for example squawks, wheezes, snores and artifacts, but do not conform to the accepted waveform of crackles. In addition, the parameters of each potential crackle are determined, compared to a range of acceptable values obtained from an empirically determined data base of crackling breath sounds, and recorded for diagnostic or other uses.

The system first finds the exact point of onset of the crackle (step 518). This is done by searching for the first value of W that is greater than $\mu \cdot k \cdot \sigma(W)$, within the t milliseconds preceding the point of maximal value $W_{max}$ used as the index point for this crackle. $\mu$ is a predetermined onset factor, for example $\mu$=0.7, and t is a predetermined time interval, for example, in accordance with a preferred embodiment of the present invention, t=5 ms.

The system removes the DC level and trends that may exist in the crackle containing portion of the signal segment (step 520). This is done by subtracting the mean value within the segment from all its elements, by determining the linear regression of the segment and subtracting a value that is equal to the regression line amplitude from all the elements of the segment. The system subjects the "cleaned up" signal segment to a curve fitting routine (step 522) which fits a curve, generally defined by equation 12 hereinbelow, to the crackle in the segment.

$$Y = A \cdot B(t) \cdot C(t) \quad (12)$$

wherein the first element A of equation 12, defines the crackle amplitude, the second element B(t) of the equation defines its envelope characteristics, and the third element C(t) of the equation defines the oscillatory component of the crackle.

Preferably, the system performs the curve fit by using a form of the general equation 12 which is defined by equation 13:

$$y = A \cdot \frac{t^n}{1 + (m \cdot t)^k} \cdot \sin\left(\frac{2\pi f_0 t}{1 + C \cdot t}\right) \quad (13)$$

where A is an amplitude parameter, t is the time in seconds within the segment (starting with the crackle onset), $f_0$ is the initial crackle frequency in Hz, C determines the rate of increase or decrease of the crackle's internal frequency. Larger values of C cause faster diminution of frequency if C is positive and faster increase of frequency if C is negative. When C=0, the frequency remains constant at $f_0$. n determines the acuteness at which the crackle amplitude rises (small values of n are associated with faster rise, since t<<1). k determines the rate of crackle decay where increasing k speeds up the rate of crackle envelope amplitude reduction beyond its peak. m influences the position of the peak of the crackle envelope (smaller values of m move the peak to later times). It is noted that k and m interact and have mutual effects on the rate of crackle decay.

The system determines the goodness of fit of the potential crackle by checking the calculated values of $Chi^2$ and R of the fit (step 524). If $Chi^2$ and R are not adequate, for example if R<0.85, $Chi^2$>20,000, the system blanks the Z values within the range of values $T_{cx}+\Delta t$ of the currently recorded maximal peak by equating them to zero (step 526) and transfers control to step 504. The system then repeats the peak searching steps for locating the subsequent maximal peak of Z thereby searching for additional crackles within the segment.

This process is repeated until there are no more maxima that are greater than $k \cdot \sigma(W)$, or until more than a certain predetermined portion of the segment, for example half of the segment, has been blanked.

If the goodness of fit is adequate, for example if R>0.85, $Chi^2$<20,000, the system checks whether the calculated parameters k, A, m, n, C and $f_0$ are within the empirically determined range for crackles individually, and performs a scoring procedure (step 528).

The scoring procedure calculates a score by using equation 14:

$$SCORE = \frac{1}{n}\sum_{i=1}^{n}\left|\frac{P_i - \overline{P}_i}{\overline{P}_i}\right| \cdot D_i \quad (14)$$

where $P_i$ designates the following parameters $P_1$=k, $P_2$=m, $P_3$=n, $P_4$=c and $P_5$=$f_0$, $D_i$ designates the corresponding weighing factors representing the relative importance of each of the parameters $P_i$ as determined empirically and $P_i^{(bar)}$ are the corresponding empirically determined values of the parameters of respiratory crackles.

If the values of the parameters $P_i$ or of the score are not within the empirically determined crackle range, the system marks the current potential crackle as an artifact (step 530), records the artifact's parameters (step 532) and transfers control to step 526.

If the values of the parameters $P_i$ or of the score are within the empirically determined crackle range, the system marks the potential crackle as a verified crackle, records the crackle's parameters (step 532), blanks the range of values around the current peak as described hereinabove (step 526) and transfers control to step 504 for detecting additional potential crackles. The values of the parameters are then used to distinguish between fine and coarse crackles. In particular, the value of $f_0$ is used, where crackles having values of $f_0$ that are greater than a specific threshold, for example crackles for which $f_0$>500 Hz, are designated as fine crackles, while crackles having values of $f_0$ that are smaller than the specific threshold, for example crackles for which $f_0$<500 Hz, are designated as coarse crackles.

The Hardware Verification Method

It will be appreciated that the contact sensors 4, 6, 64 and 66 of the present invention can move during the course of use, particularly when the use is extended, such as in the case of the monitor or recorder. Shifts of position or contact with the body may cause a substantial change in the amplitude or frequency response of the breath sounds. The present invention includes a hardware verification system and method which determines that all of the sensors are operating properly. The hardware verification can be performed at any time and is useful for verifying that a possible alarm is justified and was not generated by a problem with the equipment.

In accordance with a preferred embodiment of the present invention, the piezoelectric contact sensors 4 and 6 are individually utilized, during hardware verification, as sound emitters through switching of the input and output of the contact sensors and providing thereto a voltage waveform. In response, the sound emitting "sensor" produces a sound which is transmitted through the body tissues and is detected by the remaining sensors. Features of the emitted sound are relatively constant as long as the system is stable. However, if the position of either the emitting sensor or one or more of the receiving sensors has changed, the received waveforms will be altered from baseline waveforms produced during a setup period. It will be appreciated that the emitting sensor can produce multiple sounds to increase the signal-to-noise ratio of the received waveforms and that all of the sensors can sequentially act as an emitting sensor for the other sensors.

The received waveforms are compared to the baseline waveforms using any suitable comparison method. For example, a cross-correlation can be performed between each received waveform and its corresponding baseline waveform, using the timing of the emitted sound as a trigger. Other methods can be utilized to determine the degree of similarity between the old and new signals. For example, each new waveform can be subtracted from its corresponding baseline waveform, followed by integration of the squares of the residuals, etc. If the difference between the old and new waveforms is greater than a predetermined threshold, there is a malfunction and the system generates an alert.

It will be appreciated by persons skilled in the art that the present invention is not limited to what has been particularly shown and described hereinabove. Rather the scope of the present invention is defined only by the claims which follow:

I claim:

1. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said breath sounds signal and matches said signal or data derived from said signal to at least one breath sounds template, at least one of said templates parametrizing regular chest wall breath sounds, wherein the template for regular chest wall breath sounds is a frequency domain curve of a low pass filter, wherein the parameters are an amplitude, cutoff frequency and slope of the low pass filter.

2. A system according to claim 1 wherein said breath sounds analyzer analyzes said breath sounds only if said breath sound data is not significantly correlated with ambient noise.

3. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said breath sounds signal and matches said signal or data derived from said signal to at least one breath sounds template, at least one of said templates parametrizing regular tracheal breath sounds, wherein the template for regular tracheal breath sound is a frequency domain curve of an ensemble of second order systems wherein the parameters are a set of amplitude coefficients, a set of damping coefficients and a set of resonance frequencies.

4. A system according to claim 3 wherein said breath sounds analyzer analyzes said breath sounds only if said breath sound data is not significantly correlated with ambient noise.

5. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said breath sounds signal and matches said signal or data derived from said signal to at least one breath sounds template, at least one of said templates parametrizing a wheeze;

wherein the template for a wheeze is a narrow frequency domain peak whose width at half height spreads less than 32 Hz to either side of a center frequency of said narrow peak and has less than three harmonics, said narrow peak occurring within at least three time segments spanning between 150 and 2500 ms wherein said frequency of said narrow peak varies less than a predetermined amount within said three segments.

6. A system according to claim 5, wherein said breath sounds analyzer analyzes said breath sounds only if said breath sound data is not significantly correlated with ambient noise.

7. A system according to claim 5, wherein each said segment extend for 50 msec and wherein said predetermined amount is 10%.

8. A system according to claim 7 wherein said breath sounds analyzer analyzes said breath sounds only if said breath sound data is not significantly correlated with ambient noise.

9. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said breath sounds signals and matches said signals or data derived from said signals to at least one breath sounds template, at least one of said templates parametrizing a rhonchus;

wherein the template for a rhonchus is a repetitive sound in said breath sound data having a series of generally evenly spaced time and frequency domain peaks wherein the sound has a significant lack of time and frequency correlation with ambient noise.

10. A system according to claim 9 wherein said breath sounds analyzer analyzes said breath sounds only if said breath sound data is not sigificantly correlated with ambient noise.

11. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said breath sounds signal and matches said signal or data derived from said signal to at least one breath sounds template, at least one of said templates parametrizing a snore;

wherein the template for a snore is a repetitive sound, that is significantly correlated with ambient noise, and has generally evenly spaced time domain sound structures and evenly spaced frequency domain peaks, wherein an average time spacing between sound structures is generally equal to one divided by an average of the spacing between frequency peaks.

12. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said breath sounds signal and matches said signal or data derived from said signal to at least one breath sounds template, at least one of said templates parametrizing a cough;

wherein the template for a cough is a sound occurring during expiration that has a significant correlation with ambient noise and which endures 0.2–3 seconds and has a double hump time domain envelope and a relatively flat frequency spectrum.

13. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said breath sounds signals and matches said signals or data derived from said signals to at least one breath sounds template, at least one of said templates parametrizing a crackle;

wherein the template for a crackle is a curve, whose onset point begins as an abrupt change in said breath sound data, which generally matches:

$$y = A * B(t) * C(t)$$

where y is a breath sound signal beginning at said onset point, t begins at said onset point, A is an amplitude parameter, B(t) is an envelope function and C(t) is an oscillatory function.

14. A system according to claim 13 and wherein:

$$B(t) = \frac{t^n}{1 + (mt)^k} \quad (16)$$

$$C(t) = \sin\left(\frac{2\pi f_0 t}{1 + Ct}\right)$$

where $f_0$, C, n, m and k are template fitting parameters.

15. A system according to claim 14 wherein said breath sounds analyzer analyzes said breath sounds only if said breath sound data is not significantly correlated with ambient noise.

16. A system according to claim 9 wherein said breath sounds analyzer analyzes said breath sounds only if said breath sound data is not significantly correlated with ambient noise.

17. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a ambient noise microphone, adapted to produce an ambient noise signal responsive to ambient noise;

an ambient noise level detector that quantifies the ambient noise signal as representing loud ambient noise or a low level of ambient noise;

a loud noise analyzer that analyzes the breath sound signal to determine whether at least one of snores and coughs are present when said ambient noise is quantified as loud ambient noise; and a breath analyzer that analyzes the breath sound signal to determine breathing activity and to detect adventitious breath sounds in said breath sound signals when said ambient noise is quantified as low level noise.

18. A system according to claim 17 and additionally including a stethoscope converter, comprising at least a channel selector and at least one speaker, which converter receives and is adapted to provide said data to the ears of an operator.

19. A system according to claim 17 and wherein said adventitious breath sounds are at least one of the following adventitious breath sounds: a wheeze, a rhonchus, and a crackle.

20. A system according to claim 17 and also comprising a timing analyzer for determining timing of breathing activity and relative timing and duration of said regular and adventitious breath sounds.

21. A phonopneumograph according claim 17 and including a display which indicates regular breathing and which indicates when in the respiratory cycle an adventitious breath sound has occurred.

22. A phonopneumograph according to claim 17 wherein said adventitious breath sounds include at least a wheeze.

23. A phonopneumograph according to claim 17 wherein said adventitious breath sounds include at least a cough.

24. A phonopneumograph according to claim 17 wherein said adventitious breath sounds include at least a rhonchus.

25. A phonopneumograph according to claim 17 wherein said adventitious breath sounds include at least a snore.

26. A phonopneumograph according to claim 17 wherein said adventitious breath sounds include at least a crackle.

27. A breath sounds for monitoring breath sounds produced by a respiratory system within a patient's body, the system comprising:

at least one breath sounds sensor adapted to receive breath sounds conducted through a patient's body and produce at least one breath sounds signal responsive to the breath sounds; and a breath sounds analyzer which receives said at least one breath sounds signal and matches the breath sound signal or data produced from the breath sound signal to a plurality of breath sound templates each of which parametrizes one type of breath sound and the presence of regular or adventitious breath sounds only when said breath sound data or signal matches, within predetermined goodness of fit criteria, one or more of said breath sound templates; and a log unit which logs template parameters of at least said detected adventitious sounds.

28. A monitor according to claim 27, and wherein said log unit comprises a report unit for reporting said template parameters and for analyzing and presenting trends of said detected adventitious sounds.

29. A monitor according to claim 27, and including a raw data recorder that records said breath sound signals whenever adventitious sounds are detected.

30. A monitor according to claim 25 and wherein said plurality of breath sound templates parametrize at least one of the following sounds: regular breathing, a wheeze, a cough, a rhonchus, a snore and a crackle.

31. A breath sounds meter for measuring cyclic breath sounds produced by a respiratory system within a patient's body, the system comprising;
   at least one breath sounds sensor adapted to receive breath sounds conducted through a patient's body and produce at least one breath sounds signal responsive to the breath sounds; and
   a breath sounds analyzer that receives said breath sounds signal and determines, responsive to the signal or data derived from the signal, regular breath sounds or adventitious breath sounds; and
   a display that indicates at least regular breathing and when in the respiratory cycle each of said adventitious sounds occurs and which displays at least a parametric description of said breath sounds.

32. A meter according to claim 31 wherein said breath sounds analyzer comprises a template matcher that receives the breath sound signal and matches the breath sound signal or data produced from the breath sound signal to a plurality of breath sound templates each of which parametrize one type of breath sound and determines that regular or adventitious breath sounds are present only when said breath sound data or signal matches, within predetermined goodness of fit criteria, one or more of said breath sound templates.

33. A meter according to claim 32 and wherein said display includes means for displaying graphical, and textual descriptions of regular breathing and adventitious breath sounds.

34. A meter according to claim 32 and also comprising a communication unit for transmitting breath information to an external physician unit.

35. A meter according to claim 34 and wherein said breath information comprises at least one of the following: raw breath sound data, parameters of said regular breathing, said detected adventitious breath sounds and a report of breathing over a predetermined period of time.

36. A system according to claim 31 and additionally including a stethoscope converter, comprising at least a channel selector and at least one speaker, which converter receives and is adapted to provide said data to the ears of an operator.

37. A monitor according to claim 31, and including a raw data recorder that records said breath sound signals whenever adventitious sounds are detected.

38. A breath sounds monitor according to claim 27 comprising:
   a storing unit which stores at least times at which said adventitious sounds occurred.

39. A monitor according to claim 25 and wherein said storage unit also stores a small portion of said breath sound signals.

40. A monitor according to claim 39 and wherein said breath sound signals are selected for recording whenever adventitious breath sounds are detected.

41. A monitor according to claim 25 and wherein said breath sounds analyzer comprises a trends analyzer for analyzing trends in said breath sound signals over said relatively long period.

42. A monitor according to claim 25 and also comprising:
   an ambient noise microphone placed near said patient for measuring ambient noise data;
   an ambient noise level detector utilizing said ambient noise data to quantify the level of noise; and
   a loud noise analyzer for detecting the presence of snores and coughs in said breath sound signals when said ambient noise level detector detects loud noise in said ambient noise data,
   wherein said breath sounds analyzer operates when said ambient noise level detector detects a low level of noise.

43. A monitor according to claim 25 and also comprising a communication unit for transmitting breath information to an external physician unit.

44. A phonopneumographic system comprising:
   a plurality of piezoelectric sensors adapted to be placed around a patient's respiratory system for measuring breath related activity; and
   a verification unit connected to said sensors for individually activating each sensor to produce a sound and for each sound produced, measuring said sound with the non-activated ones of said sensors and, in a verification mode, comparing the measured sounds with those received during a training mode.

45. A system according to claim 44 wherein the verification unit individually activates the sensors to produce multiple sounds to improve a signal to noise of the sounds used in said comparison.

46. A hardware verification method for a system having a plurality of piezoelectric transducers placed around an object, the method comprising:
   in a training mode:
      individually activating at least some of said transducers to produce at least one sound; and
      for each sound produced, measuring said sound with non-activated ones of said transducers;
   in a verification mode:
      individually activating at least some of said transducers to produce a at least one sound;
      for each sound produced, measuring said sound with non-activated ones of said transducers; and
      identifying malfunctioning sensors by comparing the measured sounds with those received during said training mode.

47. A method according to claim 46 wherein the at least one sound comprises a plurality of sounds.

48. A method for detecting a wheeze in breath sound data, the method comprising:
   segmenting said breath sound data into segments;
   per segment:
      generating the spectrum of said breath sound segment;
      removing noise and regular breath sound spectrum patterns from said breath sound spectrum, thereby to produce a non-regular breath sound spectrum;
      detecting narrow peaks within said non-regular breath sound spectrum;
   per a small group of segments:
      defining a potential wheeze if narrow peaks exist in consecutive segments and if said narrow peaks are located within a predetermined small frequency range across said consecutive segments;
      defining a wheeze if the narrow peaks of said potential wheeze have less than three harmonics each.

49. A method according to claim 48 and wherein said small group of segments spans at least 150 ms of breath data.

50. A method according to claim 48 and wherein said small frequency range is not greater then 64 Hz around the frequency of said narrow peak at half height of said narrow peak.

51. A method of detecting a rhonchus in breath sound data, the method comprising:
   segmenting said breath sound data into segments;
   per segment, detecting narrow peaks within a spectrum of said segment;
   per a small group of segments:
      defining a potential rhonchus if narrow peaks exist in consecutive segments and if said narrow peaks are located within a predetermined small frequency range across said consecutive segments;
      if there are more than two harmonics in each segment, generating a frequency transfer function between said breath sound data and measured ambient noise of a space where said breath sound data was gathered;
      determining a coherence graph of the transfer function; and
      defining each narrow peak as a ronchus if the frequency range of high coherence of said coherence graph does not correspond to the frequency range of said narrow peaks.

52. A method of detecting a cough in breath sound data, the method comprising:
   generating an amplitude spectrum of breath sound data and of ambient noise data;
   generating a transfer function between said amplitude spectra of said breath sound and ambient noise data;
   determining a coherence graph of said transfer function;
   finding peaks in said breath sound and ambient noise data;
   generating an envelope of said breath sound data, having a duration and determining the duration of said envelope;
   reviewing said breath sound and ambient noise data and identifying a cough if said breath sound and ambient noise fulfill all of the following conditions:
      a) the breath sound is an expiration sound;
      b) said peaks of said breath sound data generally coincide with said peaks of said ambient noise data;
      c) said coherence graph has a significant portion which has a high coherence level;
      d) said envelope of said breath sound data has a double hump shape; and
      e) the duration of said envelope is a predetermined length of time.

53. A method according to claim 52 and wherein said predetermined length of time is 0.2–3.0 seconds.

54. A method according to claim 52 and wherein said high coherence level is 0.7 or greater.

55. A method of detecting crackles in breath sound data, the method comprising the steps of:
   finding locations of abrupt changes in said breath sound data;
   for each abrupt change,
      finding a beginning point of said abrupt change;
      attempting to match said breath sound data following said beginning point to:

$$y = A * B(t) * C(t) \quad (17)$$

where y is said breath sound data from said beginning point, t begins at said beginning point, A is an amplitude parameter, B(t) is an envelope function and C(t) is an oscillatory function; and
   identifying a crackle if said breath sound data matches said curve.

56. A method according to claim 55 and wherein:

$$B(t) = \frac{t^n}{1 + (mt)^k} \quad (18)$$

$$C(t) = \sin\left(\frac{2\pi f_0 t}{1 + Ct}\right)$$

where $f_0$, C, n, m and k are template fitting parameters.

57. A method according to claim 55 and additionally comprising identifying a type of crackle from values of said parameters.

58. A method of determining a breathing state of a patient, the method comprising:

determining an inspiration/expiration phase of a breath from chest movement data and defining a breath variable therefrom;
   acquiring tracheal breath sound data from a subject;
   if the tracheal breath sound data are significant and if external noise is low:
      determining if the tracheal breath sound data has a generally normal shape; and
      if so, generating breath flow data from said tracheal breath sound data and from said breath phase variable;
   otherwise:
      determining if the lack of flow indicates apnea and, if so, setting an apnea alarm.

59. A method according to claim 58, and including generating a loud noise indication if a) ambient noise is high or c) the tracheal sound is too high.

60. A method according to claim 58, wherein said breath flow data has an amplitude defined by raising the tracheal breath sound data to a power between 0.45 to 0.67 and a direction of flow defined by said breath phase variable.

61. A method according to claim 58 wherein said apnea alarm is set if no tracheal sounds are recorded for a predetermined period.

62. A method according to claim 58 wherein said breath flow data is defined as the tracheal sound data to a power in the range of 0.45–0.67 and the direction of the flow is defined by said breath phase variable.

63. A method according to claim 62 wherein the power is about 0.5.

64. A method according to claim 62 wherein the apnea alarm is set if the integrated breath flow is below a predetermined value.

65. A method according to claim 58 and including determining a relationship between the breath sounds and the breath flow by simultaneously measuring the breath sounds and the breath flow and correlating them.

66. A method according to claim 58 and including segmenting said breath sound data into segments and wherein determining if the breath sound has a normal shape is based on breath sounds in segments of said breath sound data.

67. A method according to claim 66 wherein the presence of a normal tracheal breath sound is determined by fitting the spectrum of the breath sounds data to:

$$y = \sum_{i=1}^{n} \frac{m_{1i} \cdot f}{\sqrt{m_{2i} \cdot f^2 + (m_{3i}^2 - f^2)^2}} \quad n = 3 \pm 1$$

wherein $m_{1i}$ is a set of amplitude coefficients, f is the frequency, $m_{2i}$ is a set of damping coefficients, $m_{3i}$ is the set of resonance frequencies, i is the serial number of the resonance frequencies and n is the total number of resonance frequencies (n=3±1) and determining if the fit meets a predetermined goodness of fit criteria.

68. A method according to claim 58 wherein the presence of a normal tracheal breath sound is determined by fitting the spectrum of the breath sounds data to:

$$y = \sum_{i=1}^{n} \frac{m_{1i} \cdot f}{\sqrt{m_{2i} \cdot f^2 + (m_{3i}^2 - f^2)^2}} \quad n = 3 \pm 1$$

wherein $m_{1i}$ is a set of amplitude coefficients, f is the frequency, $m_{2i}$ is a set of damping coefficients, $m_{3i}$ is the set of resonance frequencies, i is the serial number of the resonance frequencies and n is the total number of resonance frequencies (n=3±1) and determining if the fit meets a predetermined goodness of fit criteria.

69. A method according to claim 58 and including recording breath sounds during a training period to determine normal values for breathing parameters.

70. A method for analyzing breath data, the method comprising:

generating a spectrum of a current segment;

determining if the current segment of data is a background segment, representing background noise, or a breath segment representing breath sounds;

averaging spectra of a plurality of segments of each type to produce an average background spectrum and an average breath sound spectrum;

for said average breath sound spectrum, subtracting said average background spectrum therefrom to produce a relatively noiseless breath spectrum;

fitting said relatively noiseless breath spectrum to a predetermined normal curve and determining a quality of fit;

activating an irregular breath sounds detector if said quality of fit is poor.

71. A method according to claim 70, and including selecting said predetermined normal curve from a plurality of predetermined normal spectra depending on whether a patient generating said breath data is a male, a female or a child.

72. A method according to claim 62 wherein the normal curve is of the form:

$$y = \frac{A}{1 + (f/f_0)^S},$$

wherein:

A is an amplitude of a low frequency plateau; f is a frequency and $f_o$ and S are fitting parameters of the curve.

73. A method according to claim 70 wherein the normal curve is of the form:

$$y = \sum_{i=1}^{n} \frac{m_{1i} \cdot f}{\sqrt{m_{2i} \cdot f^2 + (m_{3i}^2 - f^2)^2}} \quad n = 3 \pm 1$$

wherein $m_{1i}$ is a set of amplitude coefficients, f is the frequency, $m_{2i}$ is a set of damping coefficients, $m_{3i}$ is the set of resonance frequencies, i is the serial number of the resonance frequencies and n is the total number of resonance frequencies (n=3±1) and determining if the fit meets a predetermined goodness of fit criteria.

74. A method according to claim 70 and including recording breath sounds during a training period to determine normal values for said fit.

75. A method of detecting a snore in segments of breath sound data, said segments having a beginning and an end, the method comprising:

determining that a current segment is an inspiratory segment;

identifying amplitude peaks in said inspiratory segment and determining an average peak-to-peak time delta__t;

identifying at least three frequency peaks within a range of frequencies in a power spectrum of said breath sound data which are significantly large and determining an average peak-to-peak frequency delta__f;

generating a frequency transfer function between said breath sound data and measured ambient noise where said breath sound data was gathered;

determining a coherence graph of said transfer function; and identifying a snore if delta__t multiplied by delta__f is close to 1 and if a frequency range of high coherence of said coherence graph includes said frequency peaks.

76. A method according to claim 75 and wherein identifying amplitude peaks comprises:

calculating an inverse Fourier transform of said power spectrum and generating thereby cleaned data;

searching for a first peak in said cleaned data beginning between 5 to 25 ms from said segment's start; and searching for peaks following said first peak.

77. A method according to claim 75 and wherein identifying frequency peaks comprises:

calculating a histogram of said power spectrum;

determining a variance of said histogram; and defining as peaks those points having values which are at k variance or higher, where k is at least 3.

78. A phonopneumograph system for analyzing breath sounds produced by a respiratory system within a patient's body, the system comprising:

at least one breath sounds sensor adapted to receive breath sounds conducted through a patient's body and produce at least one breath sounds signal responsive to the breath sounds; and a ambient noise microphone, adapted to produce an ambient noise signal responsive to ambient noise when placed near said patient;

an ambient noise level detector that quantifies the ambient noise signal as representing loud ambient noise or low level ambient noise; and a breath analyzer that analyzes the breath sound signal to determine the presence of regular breathing activity or adventitious breath sounds including one or more of a wheeze, a rhonchus or a cackle in said breath sound signals only when said ambient noise is quantified as low level noise.

79. A system according to claim 78, wherein the adventitious breath sounds whose presence is determined includes at least a wheeze.

80. A system according to claim 78, wherein the adventitious breath sounds whose presence is determined includes at least a rhonchus.

81. A system according to claim 78, wherein the adventitious breath sounds whose presence is determined includes at least a crackle.

82. A phonopneumograph for analyzing breath sounds, produced by a respiratory system the phonopneumograph comprising:

at least one breath related sensor adapted to be placed adjacent the respiratory system of a patient, the sensor measuring breath related activity, said at least one sensor producing breath sound data;

a breath analyzer which matches said breath sound data to a plurality of breath sound templates each of which is characteristic of and parametrizes one type of breath sound and which produces a signal indicative of the presence of a particular regular or adventitious breath sounds only when said breath sound data matches, within predetermined goodness of fit criteria, one or more of said breath sound templates;

wherein the sound templates comprise particular standard time or frequency domain patterns characteristic of a particular breath sound and wherein the parameters define particular variations in said pattern.

83. A phonopneumograph according to claim 82 wherein the at least one template comprises a template for regular chest wall breath sound, said template for regular chest wall breath sound comprising a curve in the frequency domain of said breath sound data having the shape of a low pass filter, wherein the parameters are the amplitude, cutoff frequency and slope of the low pass filter.

84. A phonopneumograph according to claim 82 wherein the at least one template comprises a template for regular tracheal breath sound, said template for regular tracheal breath sound comprising a curve in the frequency domain of said breath sound data of an ensemble of second order resonant systems wherein the parameters stored are a set of amplitude coefficients, a set of damping coefficients and a set of resonance frequencies.

85. A phonopneumograph according to claim 82, wherein the at least one template comprises a template for a wheeze, said template for a wheeze comprising a narrow peak in the frequency domain of said breath sound data whose width at half height spreads less than a predetermined frequency width, which has fewer than three harmonics, said narrow peak occurring within at least three time segments comprising a predetermined time period, the frequency of said narrow peaks varying less than 1.5 Hz per msec within said at least three said occurrences.

86. A phonopneumograph according to claim 82, wherein the at least one template comprises a template for a rhonchus, said template for a rhonchus comprising a repetitive sound in said breath sound data having generally evenly spaced peaks in the time and frequency domains that has a significant lack of correlation in the time and frequency domains with ambient noise.

87. A phonopneumograph according to claim 82, wherein the at least one template comprises a template for a snore, said template for a snore comprising a repetitive sound in said breath sound data having generally evenly spaced sound structures in the time domain and evenly spaced peaks in the frequency domain, whose average spacing between sound structures in the time domain is generally equivalent to the inverse of the average spacing between peaks in the frequency domain and wherein said breath sound data is significantly correlated with ambient noise.

88. A phonopneumograph according to claims 82, wherein the at least one template comprises a template for a cough, said template for a cough comprising a sound occurring during a sudden expiratory chest motion which endures 0.2–3 seconds, has a double hump envelope in the time domain, has a relatively flat spectrum and which has a significant correlation with ambient noise.

89. A phonopneumograph according to claim 82, wherein the at least one template comprises a template for a crackle, said template for a crackle comprising a curve, whose onset point begins as an abrupt change in said breath sound data, and which generally matches the function:

$$y = A * B(t) * C(t)$$

where y is said breath sound data beginning at said onset point, t is the time measured from said onset point, A is an amplitude parameter, B(t) is an envelope function and C(t) is an oscillatory function.

90. A phonopneumograph according to claim 89 wherein:

$$B(t) = \frac{t^n}{j + (mt)^k} \text{ and } C(t) = \sin\left(\frac{2\pi f_o t}{1 + Ct}\right),$$

where $f_o$, C, n, m and k are parameters.

* * * * *